United States Patent
Shorr et al.

(10) Patent No.: US 11,497,761 B2
(45) Date of Patent: Nov. 15, 2022

(54) COMPOSITIONS FOR THE TREATMENT OF METASTATIC CANCER

(71) Applicant: BioDev, LLC, Edison, NJ (US)

(72) Inventors: Robert Shorr, Edison, NJ (US); Jeffrey Schwartz, Edison, NJ (US)

(73) Assignee: BioDev, LLC, Edison, NJ (US)

( * ) Notice: Subject to any disclaimer, the term of this patent is extended or adjusted under 35 U.S.C. 154(b) by 0 days.

(21) Appl. No.: 16/920,558

(22) Filed: Jul. 3, 2020

(65) Prior Publication Data

US 2021/0000850 A1    Jan. 7, 2021

Related U.S. Application Data

(60) Provisional application No. 62/870,387, filed on Jul. 3, 2019.

(51) Int. Cl.
| | |
|---|---|
| *A61K 31/708* | (2006.01) |
| *A61P 35/04* | (2006.01) |
| *A61K 31/25* | (2006.01) |
| *A61K 31/716* | (2006.01) |

(52) U.S. Cl.
CPC ............ *A61K 31/708* (2013.01); *A61K 31/25* (2013.01); *A61K 31/716* (2013.01); *A61P 35/04* (2018.01)

(58) Field of Classification Search
CPC ...... A61K 31/708; A61K 31/25; A61K 31/716
See application file for complete search history.

(56) References Cited

U.S. PATENT DOCUMENTS

| | | | |
|---|---|---|---|
| 10,736,913 B1 * | 8/2020 | Yuan ................. | A61K 39/39541 |
| 2019/0046557 A1 * | 2/2019 | Zhang ................. | A61K 31/716 |

OTHER PUBLICATIONS

Haqq, J. et al., Mol. Nutr. Food Res., "Targeting pancreatic cancer using a combination of gemcitabine with the omega-3 polyunsaturated fatty acid emulsion, Lipidem", 2016, vol. 60, pp. 1437-1447 (Year: 2016).*
Lappano, R. et al., Cell Death Discovery, "The lauric acid-activated signaling prompts apoptosis in cancer cells", 2017, vol. 3, 9 pages (Year: 2017).*
Philippoussis, F. et al., Cell Death and Differentiation, "Derivatives of monoglycerides as apoptotic agents in T-cells", 2001, vol. 8, pp. 1103-1112 (Year: 2001).*
"Prevent", WordNet Search 3.1, available at http://wordnetweb.princeton.edu/perl/webwn, last accessed Jan. 2021 (Year: 2021).*
Zips, D. et al., In Vivo, "New Anticancer Agents: In Vitro and In Vivo Evaluation", 2005, vol. 19, pp. 1-8 (Year: 2005).*
Wishart DS, Feunang YD, Guo AC, Lo EJ, Marcu A, Grant JR, et al. DrugBank 5.0: a major update to the DrugBank database for 2018. Nucleic Acids Res 2018;46(D1):D1074-D82 doi 10.1093/nar/gkx1037.
Volman JJ, Ramakers JD, Plat J. Immune modulation by dietary glucans from oat and mushrooms: results from in vitro, animal and human studies. Physiol Behav 2008;94(2):276-84 doi 10.1016/j.physbeh.2007.11.045.
Li Q, Estes JD, Schlievert PM, Duan L, Brosnahan AJ, Southern PJ, et al. Glycerol monolaurate prevents mucosal SIV transmission. Nature 2009;458(7241):1034-8 doi 10.1038/nature07831.
Lieberman S, Enig MG, Preuss HG. A Review of Monolaurin and Lauric Acid: Natural Virucidal and Bactericidal Agents. Alternative and Complementary Therapies 2006;12(6):310-4 doi 10.1089/act.2006.12.310.
Schlievert PM, Kilgore SH, Seo KS, Leung DYM. Glycerol Monolaurate Contributes to the Antimicrobial and Anti-Inflammatory Activity of Human Milk. Sci Rep 2019;9(1):14550 doi 10.1038/s41598-019-51130-y.
Zhang MS, Tran PM, Wolff AJ, Tremblay MM, Fosdick MG, Houtman JCD. Glycerol Monolaurate (GML) induces filopodia formation by disrupting the association between LAT and SLP-76 microclusters. Science Signaling 2018;11(528) doi 10.1126/scisignal.aam9095.
Mo Q, Fu A, Deng L, Zhao M, Li Y, Zhang H, et al. High-dose Glycerol Monolaurate Up-Regulated Beneficial Indigenous Microbiota without Inducing Metabolic Dysfunction and Systemic Inflammation: New Insights into Its Antimicrobial Potential. Nutrients 2019;11(9) doi 10.3390/nu11091981.
Crunkhom S, Dearie F, Mantzoros C, Gami H, da Silva WS, Espinoza D, et al. Peroxisome proliferator activator receptor gamma coactivator-1 expression is reduced in obesity: potential pathogenic role of saturated fatty acids and p38 mitogen-activated protein kinase activation. J Biol Chem 2007;282(21):15439-50 doi 10.1074/jbc.M611214200.
Fauser JK, Matthews GM, Cummins AG, Howarth GS. Induction of Apoptosis by the Medium-Chain Length Fatty Acid Lauric Acid in Colon Cancer Cells due to Induction of Oxidative Stress. Chemotherapy 2013;59(3):214-24 doi 10.1159/000356067.

(Continued)

*Primary Examiner* — Bahar Craigo
(74) *Attorney, Agent, or Firm* — Morgan, Lewis & Bockius LLP

(57) ABSTRACT

Compositions for the treatment, prevention of, proliferation of, or killing of cells associated with metastatic progression of cancer in a cancer patient are disclosed. More specifically, compositions containing a single type of glyceride, fatty acid, or fatty acid derivative, mixtures thereof, or glycerides and/or fatty acids/fatty acid derivatives in combination with cancer metabolism disruptors, chemotherapeutics and modulators of immune response, are disclosed. Compositions disclosed herein include formulations of monolaurin, and formulations including monolaurin and additional components. Also, methods of treating metastatic cancer and/or preventing cancer relapse in a cancer patient by administering compositions containing a single type of glyceride, fatty acid, or fatty acid derivative, mixtures thereof, or glycerides and/or fatty acids/fatty acid derivatives in combination with cancer metabolism disruptors, chemotherapeutics and modulators of immune response, are disclosed. The compositions and methods disclosed herein are useful for killing circulating cancer cells that cause metastasis and cancer relapse.

6 Claims, 27 Drawing Sheets

(56) References Cited

OTHER PUBLICATIONS

Weng WH, Leung WH, Pang YJ, Hsu HH. Lauric acid can improve the sensitization of Cetuximab in KRAS/BRAF mutated colorectal cancer cells by retrievable microRNA-378 expression. Oncol Rep 2016;35(1):107-16 doi 10.3892/or.2015.4336.

Lappano R, Sebastiani A, Cirillo F, Rigiracciolo DC, Galli GR, Curcio R, et al. The lauric acid-activated signaling prompts apoptosis in cancer cells. Cell Death Discov 2017;3:17063 doi 10.1038/cddiscovery.2017.63.

Birnie GD. The HL60 cell line: A model system for studying human myeloid cell differentiation. British Journal of Cancer 1988;58(Suppl IX):41-5.

Wang Z, Ma B, Ji X, Deng Y, Zhang T, Zhang X, et al. MicroRNA-378-5p suppresses cell proliferation and induces apoptosis in colorectal cancer cells by targeting BRAF. Cancer Cell Int 2015;15:40 doi 10.1186/s12935-015-0192-2.

Chen L-t, Xu S-d, Xu H, Zhang J-f, Ning J-f, Wang S-f. MicroRNA-378 is associated with non-small cell lung cancer brain metastasis by promoting cell migration, invasion and tumor angiogenesis. Medical Oncology 2012;29(3):1673-80.

Qian J, Lin J, Qian W, Ma JC, Qian SX, Li Y, et al. Overexpression of miR-378 is frequent and may affect treatment outcomes in patients with acute myeloid leukemia. Leuk Res 2013;37(7):765-8 doi 10.1016/j.leukres.2013.03.014.

Lieber M, Smith B, Szakal A, Nelson-Rees W, Todaro G. A continuous tumor-cell line from a human lung carcinoma with properties of type II alveolar epithelial cells. Int J Cancer 1976;17(1):62-70 doi 10.1002/ijc.2910170110.

Zhang MS, Sandouk A, Houtman JC. Glycerol Monolaurate (GML) inhibits human T cell signaling and function by disrupting lipid dynamics. Sci Rep 2016;6:30225 doi 10.1038/srep30225.

De Matteis V, Cascione M, De Giorgi ML, Leporatti S, Rinaldi R. Encapsulation of Thermo-Sensitive Lauric Acid in Silica Shell: A Green Derivate for Chemo-Thermal Therapy in Breast Cancer Cell. Molecules 2019;24(11) doi 10.3390/molecules24112034.

Goc A, Niedzwiecki A, Rath M. In vitro evaluation of antibacterial activity of phytochemicals and micronutrients against Borrelia burgdorferi and Borrelia garinii. J Appl Microbiol 2015;119(6):1561-72 doi 10.1111/jam.12970.

* cited by examiner

COMPOSITIONS FOR THE TREATMENT OF METASTATIC CANCER

RELATED APPLICATIONS

This application claims the benefit of U.S. Provisional Application No. 62/870,387, filed on Jul. 3, 2019. The entire teachings of the above application are incorporated herein by reference.

BACKGROUND OF THE INVENTION

The present invention generally relates to compositions and methods for treating, preventing proliferation of, or killing cells associated with metastatic cancer progression (including various cancers suffered by cancer patients), and, more particularly, to compositions and methods of killing circulating and other cancer cells that may contribute to metastasis, recurrent, refractory disease and overall disease progression.

BRIEF SUMMARY OF THE INVENTION

In one embodiment of the invention there is a composition for treating, killing, or inhibiting proliferation of populations of cells associated with cancer progression and metastasis in a cancer patient (human or animal) in need thereof. Cells associated with cancer progression and metastasis include any cells that promote metastasis of a cancer, including tumor progenitor cells, circulating tumor cells, invasive circulating tumor cells, and primary and metastatic tumor cells. The compositions can be used to kill circulating and other metastatic cancer cells.

The composition comprises an effective amount or concentration of one or more bioactive fatty acids and fatty acid derivatives in saturated or unsaturated forms without limitation. The fatty acid derivatives may include glycerides, fatty acid salts, hydroxy fatty acids, and fatty acid esters and amides of sugars and amino acids in powdered crystalline form, as oils, liquid crystals, or emulsions. The fatty acids may be naturally occurring. The fatty acid derivatives may be synthetic.

In a further embodiment, the composition includes glycerides, and more particularly, monoglycerides (e.g., monolaurin without limitation) as isomeric substituents. In another embodiment, the composition includes one or more of fatty acids and fatty acid derivatives having carbon chain lengths from 4 to 20 carbons.

In another embodiment, the composition further comprises one or more nucleosides and/or nucleoside precursors (e.g., inosine and analogs thereof).

In another embodiment, the composition further comprises one or more anti-cancer agents, such as metabolism disruptors, targeted therapeutics, chemotherapeutics, in combination with modulators of immune response. The modulators of immune response include stimulatory signal transduction modulators and activators of immune response as well as agents intended to disrupt mechanisms of cancer avoidance of immune response.

In yet a further embodiment, the composition further comprises one or more modulators of immune response. These modulators of immune response may include nucleosides and/or nucleoside precursors (e.g., inosine and analogs thereof) and/or one or more fibrous carbohydrates/fibers (e.g., β-glucan) without limitation. The inventive composition according to certain embodiments comprises an effective amount or concentration of one or more one or more nucleosides and/or nucleoside precursors (e.g., inosine and analogs thereof). In accordance with certain embodiments, the inventive composition comprises an effective amount or concentration of one or more bioactive fibrous carbohydrates/fibers (e.g., β-glucan).

In yet a further embodiment, the composition is effective to kill a therapeutically significant number of cells related to metastatic cancer progression (e.g., invasive circulating tumor cells (iCTC)) within the cancer patient, or during in vitro laboratory protocols. A therapeutically significant decrease of cells related to metastatic cancer progression (e.g., metastatic cancer cells, circulating tumor cells (CTCs), invasive circulating tumor cells (iCTCs)) as measured by a variety of liquid biopsy techniques is preferably greater than 20%, more preferably 50% or greater, and most preferably 70% or greater.

In one embodiment, there is a method for treating metastatic cancer in a cancer patient by inhibiting proliferation of or reducing the population of, or killing cells related to disease progression of cancer (e.g., circulating cancer cells). The method comprises administering to the cancer patient in need thereof an effective amount or concentration of one or more fatty acids and fatty acid derivatives to achieve a suitable cancer cell killing plasma level (e.g., about 10 μM to about 300 μM). Thus, a therapeutically effective amount or concentration of the one or more fatty acids and fatty acid derivatives may be an amount or concentration sufficient to reach a patient plasma level of between about 10 μM and about 300 μM of the one or more fatty acids and fatty acid derivatives. The fatty acid derivatives include glycerides, acceptable fatty acid salts, hydroxy fatty acids, and fatty acid sugar esters and amides of amino acids. The fatty acids may be naturally occurring. The fatty acid derivatives may be synthetic. The effective amount or concentration is selected to disrupt and/or eliminate the cancer progression-related cells in a cancer patient (human or animal) based upon liquid biopsy screening of test article drugs and formulations as above. Achievement of the desired concentration in the blood of patients according to a selected dosing protocol can be determined using bioanalytical assay of active ingredients, pharmacokinetics and drug metabolism, and of metabolites.

Administration pathways for the inventive compositions include parenteral or non-parenteral administration (e.g., intravenously, intraperitoneal, subcutaneous, intramuscular, intranasal, oral). A preferred administration pathway is oral administration. Compositions according to embodiments herein may include pharmaceutically acceptable carriers or excipients along with bioactive ingredients.

Compositions according to embodiments herein may be administered a single time, daily on a chronic basis, or multiple times per week depending on patient needs, rates of drug clearance from the body, and on safety. In a preferred embodiment, compositions in accordance with the present inventions can be administered multiple times per day to a patient.

Dosage level and frequency of administration protocols, compositions, as well as potential use of additional therapeutic agents in combination can be optimized during the course of disease by obtaining patient biopsies (e.g., bodily fluids such as blood, other biopsies) and physical assays, analyzing the results, and adjusting treatment and dosing protocols accordingly. These biopsies and assays may determine changes in numbers, of metastatic cancer-related cell types, and/or degree of sensitivity to bioactive components of the compositions according to the present invention via measurement of cells related to the metastatic progression of cancer (e.g., cumulative invasive circulating tumor cells (iCTCs)) from patient blood samples—such measures of these cells are likely to correlate with overall patient response to the drug protocols and overall patient survival. Such biopsies and assays can also determine the cancer cell types not responsive to prior therapies.

In a further embodiment, the method includes administering an effective amount or concentration of one or more bioactive fatty acids and fatty acid derivatives in saturated or unsaturated forms without limitation. In a particular embodiment, the method includes administering an effective amount or concentration of isomers and metabolites of glycerides, such as but not limited to monoglycerides (e.g, 1, 2-monolaurin) and/or analogs prepared from lauric acid, to a patient.

In another embodiment, the method further includes administering an effective amount or concentration of bioactive anti-cancer cell agents, such as metabolism disruptors, targeted therapeutics, chemotherapeutics, in combination with modulators of immune response. Suitable modulators of immune response may include nucleosides, nucleoside precursors, and/or one or more fibrous carbohydrates/fibers.

In particular embodiments of the method, an effective amount or concentration of one or more nucleosides and/or nucleoside precursors (e.g., inosine and/or analogs thereof) is administered. In yet a further embodiment, the method further comprises administration of an effective amount or concentration of one or more fibrous carbohydrates/fibers (e.g., β-glucan) without limitation.

In certain embodiments, the method comprises administering an effective amount of fatty acids and/or fatty acid derivatives, administering an effective amount of one or more nucleosides and/or nucleoside precursors (e.g., inosine and/or analogs thereof), and administering an effective amount of one or more fibrous carbohydrates/fibers (e.g., β-glucan). In a particular embodiment, the method comprises administering monolaurin, inosine, and β-glucan.

In one embodiment there is a method for treating or preventing relapse of a cancer in a cancer patient by killings cells related to the progression of metastatic disease, wherein the method includes administering an effective amount or concentration of fatty acids and/or fatty acid derivatives to a patient (human or animal) in need thereof. Without being limited by theory, it is believed that the inventive compositions and methods herein kill these metastatic cancer-related cells by disrupting cell metabolism. Such disruption may be effected by preventing the production of ATP in cells related to the progression of metastatic disease. The fatty acid derivatives include glycerides, acceptable fatty acid salts, hydroxy fatty acids, fatty acid amides, esters and suitable linkers for sugars, and amino acids.

Dosing protocols may be chronic and used to maintain a best response or to prevent or delay the appearance of relapsed, recurrent, or refractory disease. Dosing may occur once, or only a weekly or monthly basis. Dosing may occur daily on a chronic basis, and in preferred embodiments, dosing with inventive compositions according to embodiments herein may occur multiple times daily on a chronic basis. The administered concentration and specifics of formulation sufficient to achieve this may be altered during the course of therapy.

In another embodiment there is a method for treating or preventing relapse of a cancer in a cancer patient by killing cells associated with metastatic cancer progression, wherein the method includes administering an effective amount of fatty acids and/or fatty acid derivatives and administering an effective amount of one or more cancer metabolism disruptors, targeted therapies, chemotherapeutics, and modulators of immune response. The one or more cancer metabolism disruptors, targeted therapies, chemotherapeutics, and modulators of immune response may include one or more nucleosides and/or nucleoside precursors (e.g., inosine and/or analogs thereof) and one or more sugars/fibrous carbohydrates/fibers (e.g., β-glucan). In a particular embodiment, the method comprises administering to a patient in need thereof (human or animal) an effective amount or concentration of one or more fatty acids and fatty acid derivatives (e.g., monolaurin), an effective amount or concentration of one or more nucleosides and/or nucleoside precursors (e.g., inosine and/or analogs thereof), and an effective amount or concentration of one or more sugars/fibrous carbohydrates/fibers (e.g., β-glucan). Dosing protocols may be chronic and used to maintain a best response or to prevent or delay the appearance of relapsed, recurrent, or refractory disease. The administered concentration and specifics of formulation sufficient to achieve this may be altered during the course of therapy.

In one embodiment, the cancer is metastatic cancer. In some embodiments, the metastatic cancer is characterized by invasive circulating tumor cells (iCTC). The metastatic cancer may be of any cancer type.

In some embodiments, a metastatic cancer is characterized by formation of solid tumors. Examples of metastatic cancer without intent to limit are colorectal cancer (e.g., colon carcinoma), lung cancer (e.g., alveolar lung adenocarcinoma), hematological cancer (e.g., acute myeloid leukemia, B-cell acute lymphoblastic leukemia), pancreatic cancer (e.g., pancreatic ductal adenocarcinoma, pancreatic adenocarcinoma), or brain/nervous system cancer (e.g., astrocytoma/glioma/glioblastoma).

In a further embodiment, the method includes administering glycerides, such as but not limited to C12-sucrose, C14-propylene glycol ester, fungal monoglycerides, C12 monoglycerides, C10 sucrose, C12 methyl ester, C18 monoglyceride and methyl ester isomers. Additional fatty acid analogs as examples without intent to limit are lauric sucrose ester, palmitic sucrose ester, oleic sucrose ester, linoleic sucrose ester, elaidic sucrose ester, propylene glycol myristate, and those analogs referenced in Kato et al https://cancerres.aacrjournals.org/content/canres/31/5/501.full.pdf and incorporated herein by reference. A preferred glyceride is monolaurin.

BRIEF DESCRIPTION OF THE SEVERAL VIEWS OF THE DRAWINGS

The foregoing summary, as well as the following detailed description of embodiments of the compositions and methods disclosed herein, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Figure 1:
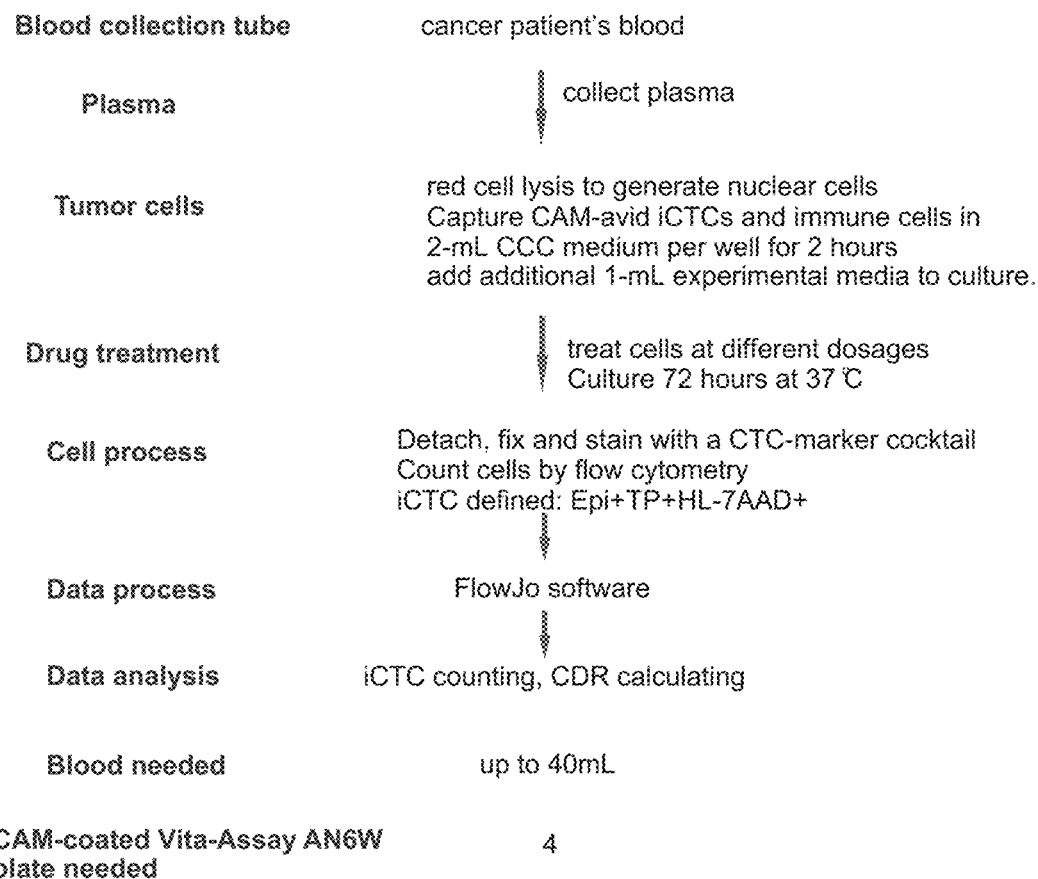
FIG. 1 is a depiction of a generalized experimental scheme for testing efficacy of a composition in accordance with an exemplary embodiment of the present invention against iCTC from the blood of pancreatic cancer patients.

While some progress has been made in the treatment of certain cancers, others remain difficult to treat even as patient numbers worldwide increase. Rahib, Lola, et al. "Projecting Cancer Incidence and Deaths to 2030: the Unexpected Burden of Thyroid, Liver, and Pancreas Cancers in the United States." *Cancer Research*, U.S. National Library of Medicine, 1 Jun. 2014, www.ncbi.nlm.nih.gov/pubmed/ 24840647. Cancer incidence and deaths in the United States are projected to increase for the years 2020 and 2030 based on changing demographics and the average annual percentage changes in incidence and death rates. Breast, prostate, and lung cancers are expected to remain the top cancer diagnoses throughout this time, but thyroid cancer will replace colorectal cancer as the fourth leading cancer diagnosis by 2030, and melanoma and uterine cancer will become the fifth and sixth most common cancers, respectively. Lung cancer is projected to remain the top cancer killer throughout this time period. However, pancreas and liver cancers are projected to surpass breast, prostate, and colorectal cancers to become the second and third leading causes of cancer-related death by 2030, respectively. The World Health Organization reports that in 2008, 7.6 million people died from cancer accounting for 13% of all deaths worldwide. Global cancer deaths have been projected to increase by 45% from 2008 to 2030. "Key Statistics." World Health Organization, World Health Organization, 3 Feb. 2012, www.who.int/cancer/resources/keyfacts/en/.

Heterogeneity of disease, even among patients with the same diagnosis and among multiple tumors in the same patient, are significant hurdles to managing tumor burden and overall survival. Cancer cell heterogeneity is believed to be driven by several factors. Both clonal and sub-clonal driver mutations have been identified and associated with evolution of disease. Jamal-Hanjani, Mariam, et al. "Translational Implications of Tumor Heterogeneity." *Clinical Cancer Research*, American Association for Cancer Research, 15 Mar. 2015, clincancerres.aacrjournals.org/content/21/6/1258. Surprisingly however, sub-clonal drivers have also been identified as an independent risk factor for disease progression.

Additionally, cytotoxic chemotherapy treatments administered to cancer patients may even play a role in cancer cell heterogeneity-patients treated with cytotoxic chemotherapy were reported to be more likely to undergo clonal evolution. This suggests that the extent of cancer cell heterogeneity may be increased during treatment. This suggests that (i) evaluation of tumor heterogeneity during treatment as a factor in response to therapy, (ii) selecting anti-cancer agents, and (iii) predicting outcomes, rather than reliance on characterizing a dominant clone thought to dictate tumor growth, may be more relevant in determining malignant potential and patient outcome. This is thought to be especially true for the evaluation of heterogeneity of responsiveness to treatment among circulating cell populations linked to metastasis and progression of disease in solid tumors.

There are several types of genetic heterogeneity in cancer biology. The most well-known is interpatient tumor heterogeneity, wherein no two patients with the same subtype of tumor behave the same clinically, with or without treatment. This may be related to host factors, such as tumor microenvironment and germline variants influencing treatment response, together with the unique somatic mutations that can occur within the tumor of each individual patient. Intratumor heterogeneity describes the existence of distinct cellular populations with specific genetic, epigenetic, and phenotypic features within tumors and has long been recognized. It has been described in several tumor types, including lung, breast, ovarian, pancreatic, kidney, colorectal, brain, and prostate cancers, as well as hematologic malignancies, such as chronic lymphoblastic leukemia and acute lymphoblastic leukemia. Metastatic lesions at different secondary sites can arise from different cellular populations within a primary tumor, resulting in heterogeneity among metastases, known as intermetastatic heterogeneity. In addition, since metastatic lesions can acquire new mutations and evolve independently with each cell division, heterogeneity within a metastasis can also exist, known as intrametastatic heterogeneity. Both can be associated with multiple mechanisms of acquired drug resistance in the same patient with metastatic disease. *Jamal-Hanjani*, refs. 6, 7, and 14-40.

Changes in the metabolism of glucose and amino acids have been shown to be associated with multiple forms of cancer and subpopulation types of cancer cells. The relationship between genetic changes and changes in metabolism continues to be intensely investigated and is not fully understood. It has been reported that cancer cells must rewire cellular metabolism to satisfy the demands of growth and proliferation. While many of the metabolic alterations are largely similar to those in normal proliferating cells, they are aberrantly driven in cancer by a combination of genetic lesions and non-genetic factors such as the tumor microenvironment. However, a single model of altered tumor metabolism does not describe the sum of metabolic changes that can support cell growth. Instead, the diversity of such changes within the metabolic program of a cancer cell can dictate by what means proliferative rewiring is driven, and can also impart heterogeneity in the metabolic dependencies of the cell. Cantor, Jason R. and David M. Sabatini, "Cancer Cell Metabolism: One Hallmark, Many Faces." Cancer Discovery, American Association for Cancer Research, 1 Oct. 2012, cancerdiscovery.aacrjournals.org/content/2/10/ 881.long.

The role of fatty acid metabolism, including both anabolic and catabolic reactions in the appearance and progression of disease through metastatic lesions, has been gaining increasing attention. Kuo, Ching-Ying, and David K Ann. "When Fats Commit Crimes: Fatty Acid Metabolism, Cancer Stemness and Therapeutic Resistance." Cancer Communications (London, England), BioMed Central, 11 Jul. 2018, www.ncbi.nlm.nih.gov/pubmed/29996946. Aberrant expression of genes involved in fatty acid synthesis or fatty acid oxidation have been shown to correlate with cancer, including metastasis, resistance to therapy and refractory progression as well as relapse and recurrent disease. There is debate as to the extent such phenotypes are strongly associated with the presence of a small percentage of unique cells among the total tumor cell population, or more representative of the total solid tumor burden with the ability to take on the metabolic functions required for metastasis if released into the circulation. In either event, the metastasizing cells that have entered the circulation have the ability to self-renew and propagate as well as invade sites distal to the primary tumor, which may lead to the appearance of new tumor lesions that may also develop resistance to cancer therapies independent of genetic alterations. Even so there is heterogeneity among circulating tumor cells for example ("Heterogeneity of circulating tumor cells (CTCs) in patients with recurrent small cell lung cancer (SCLC) treated with pazopanib," Messaritakis, I. et al. Lung Cancer, Volume 104, 16-23.

In addition to competition for survival among genetic subclones with differing degrees of proliferative potential and tumor growth, cancer cell heterogeneity may be further induced, not only by use of modes of therapy and treatment agents, but also by tumor heterogeneity promoting changes in the microenvironment. *Jamal-Hanjani*, ref. 42. In particular, heterogeneity driven by tumor microenvironment changes, interactions with stromal cells, hypoxia, acidity, the presence of inflammatory cell infiltrates and changes in extracellular matrix lead to increased pressures for phenotypic heterogeneity independent of common genetic markers. Observations in which minority subclones influence progression of the tumor mass present challenges for predictive and prognostic biomarker discovery efforts. These difficulties especially confound those focused on identifying genomic alterations in the dominant clone and subclones based on characterization of solid tumor biopsy and identifying behavior in ex vivo conditions of cell culture or in animal models. Moreover, designing singular targets for drugs based on specific genetic alterations may limit drug activity to a subpopulation of cells possessing the defined characteristics.

Lipids, free fatty acids and their metabolic byproducts have more recently garnered attention for study in understanding the changes from healthy to cancerous cells (Kuo C Y, Ann D K. When fats commit crimes: fatty acid metabolism, cancer stemness and therapeutic resistance. *Cancer Commun (Lond)*. 2018; 38(1):47. Published 2018 Jul. 11. doi:10.1186/s40880-018-0317-9 and Carracedo A, Cantley L C, Pandolfi P P. Cancer metabolism: fatty acid oxidation in the limelight. *Nat Rev Cancer.* 2013; 13(4):227-232. doi:10.1038/nrc3483) Fatty acid esters as anti-cancer agents have recently been reported (Design, Synthesis and In Vitro Anticancer Evaluation of a Stearic Acid-based Ester Conjugate A Khan et al. Anticancer Research June 2013 vol. 33 no. 62517-2524 and tested in laboratory models). Fatty acid synthesis and its metabolic links to cancer have also attracted attention as possible drug targets (CDK9 Inhibition Induces a Metabolic Switch that Renders Prostate Cancer Cells Dependent on Fatty Acid Oxidation. Itkonen H M, Poulose N, Walker S, Mills I G. and Neoplasia. 2019 July; 21(7):713-720 and Inhibition of FASN suppresses the malignant biological behavior of non-small cell lung cancer cells via deregulating glucose metabolism and AKT/ERK pathway. Chang L, Fang S, Chen Y, Yang Z, Yuan Y, Zhang J, Ye L, Gu W. Lipids Health Dis. 2019 May 24; 18(1):118).

It is believed that relating tumor cellular populations and other contributing factors to metastatic disease and screening cellular responses to test articles intended for therapy are likely to identify compounds more selective against and directed to those cells considered to be the greatest contributors to disease progression—metastasis. The use of liquid biopsy methods are rapidly gaining acceptance for the screening of new chemical entities against the heterogeneous mixture of cancer cells taken from the circulation as well as for more detailed studies of cancer cell behaviors.

Invasive circulating tumor cells (iCTC) also called cancer stem cells (CSC) are cancer cells derived from a cancer tumor or lesion within the body of a patient that are circulated throughout the patient's body in the bloodstream. These iCTCs are capable of invading new tissues and forming new cancer lesions, and they are believed to play a principal role in disease progression, recurrent and resistant disease, and poor patient outcomes. Of the various cell populations those circulating in the blood are the easiest to obtain from patients and most likely to be contributors to metastatic disease.

Descriptions of these cells as cancer-causing stem cells, tumor-initiating or tumor-promoting cells, cancer-causing clusters, drug-tolerant cells, "resisters," or side populations are all reflections of the difficulties in targeting such populations for cancer treatment. In particular, inter-conversion between cancer cells and iCTC may occur and be highly variable depending on tumor microenvironment, and treatment difficulty increases with the formation of tumor promoting clusters and the ability of such cells to achieve metabolic adaptation. In addition to characterizing the circulating cancer cell types and response to potential treatment agents, investigation of synergistic and antagonistic relationships between tumor and non-tumor cells, circulating as clusters, to disease and how these relationships may promote or impede disease progression and treatment failure will need to be better understood. *Jamal-Hanjani*, ref. 12. It is precisely the heterogeneity of the cancer-causing stem cell populations among disease indications and even individual patients that makes the screening of novel anticancer agents for activity more likely to predict results than looking at more homogeneous cell populations in culture. Even further, the monitoring of drug effectiveness and changes in the heterogeneity of the circulating cancer cells allowing for changes in treatment earlier than might be made using imaging methods alone.

It has been recognized that metabolic reprogramming of cancer cells is an essential aspect of disease origination, survival, and metastasis. Independent of cancer type, uncontrolled proliferation is accompanied by required changes in metabolic phenotype to meet needs for ATP, bio-intermediates and biomass. Many aspects of metabolic reprogramming are shared by diverse cancer cell types. The metabolic reprogramming creates the need for essential nutrients, with such need not being associated with healthy cells, and the expression of receptors and transporters to deliver these essential nutrients to the required intracellular site and the enzymes required for the cancer essential process. Depending on the cancer type and patient sub-population characteristics, nutrient scarcity or plenty, the nature of specific oncogenic events can drive specific survival and growth dependent nutrient needs and metabolic pathways. Glucose, glutamine, asparagine, and arginine are the most well-known examples of essential nutrients. Fatty acids and lipids are less well-studied, although glycerides, fatty acids and other lipids can take on signal transduction roles with translocation pathways between stromal-cancer adipocyte and other cells offering potential targets for therapeutic intervention.

Recently, multiple methods and markers for measuring levels of CTC and characterizing their subtypes have emerged. These methods provide an ability to monitor levels of and subtype distribution of CTC in patients. Multiple studies have shown that the level of circulating tumor cells can predict overall survival in a number of cancers, independently of other tests. "Circulating Tumor Cells, Disease Progression, and Survival in Metastatic Breast Cancer NEJM." New England Journal of Medicine, www.nejm.org/doi/full/10.1056/nejmoa040766. Levels of circulating tumor cells have also been proposed as a surrogate marker for survival probability. Thus, therapies that target, destroy, or disable CTC circulating in the blood of cancer patients, without causing dangerous toxicity, are of great importance in treating metastatic cancer, preventing recurrent or relapsed cancer within a patient, preventing progression of cancer, and improving overall survival of patients.

Some fatty acids, monoglycerides, and sucrose esters of fatty acids have been known to possess some level of activity against animal cancer cells in vitro, presumably through membrane interactions. Kato, Akiko, et al. Effects of Some Fatty Acid Esters on the Viability and Transplantability of Ehrlich Ascites Tumor Cells. 1971, cancerres.aacrjournals.org/content/canres/31/5/501.full.pdf. Anticancer activity investigated was found to be dependent on carbon chain length and the position of an unsaturation. Hexadecanoic, octadeconoic, octadecenoic, and octadecadienoic acids were most active, though poorly soluble. Ester linkages to lysine, arginine, and sucrose were investigated, as well as to lauric sucrose ester and monolaurin—only weak activity was observed and at concentrations suggesting non-specific possibly detergent-like effects. In general, the methyl esters evaluated were inactive in the models studied. Further, hemolytic activity of the preparations which did not correlate with anticancer activity complicated interpretation of results and further development due to potential toxicity.

As metastasizing cells and events are at the very core of disease progression and limitations of survival, the enrichment of circulating tumor cells and other cells related to metastatic progression of cancer, their identification through invasive assay activity, identification of markers for the evaluation of novel therapeutics, and the identification of new chemical entities intended for the treatment of metastasizing diseased cells using available blood tests and methods is vital. More specifically, the evaluation of test articles for the ability to kill circulating cancer cell types and any cells associated with metastatic progression of cancer with minimal effects on healthy cells and subsequent toxicity will be of utmost importance. For comparative efficiencies in achieving desired levels of cell kill of CTCs, comparisons have been made below to standard chemotherapeutic drugs assayed at typical therapeutic levels achieved in patient plasma.

"Cells associated with metastatic progression of cancer" is defined as any cell that promotes metastasis of a cancer, including tumor progenitor cells, circulating tumor cells, invasive circulating tumor cells, and primary and metastatic tumor cells.

I. Compositions

In one embodiment, the inventive composition for treating, reducing, preventing, or inhibiting proliferation of populations of cells associated with metastatic progression of cancer in a cancer patient includes single agents and combinations of naturally occurring fatty acid and their derivatives/analogs (which may be synthetic) as anti-cancer agents in co-therapeutic use, formulated as ion paired salts or chemical conjugations. That is, the inventive composition comprises a therapeutically effective amount or concentration of one or more fatty acids and fatty acid derivatives. Without being bound by theory, the inventive composition is believed to inhibit the ATP production of cells related to metastatic disease, which disrupts cancer cell metabolism and leads to cell death. The inventive compositions according to certain embodiments may be present in a suitable dosage form, and may be administered independently or administered in combination (e.g., co-formulated) with other anti-cancer cell chemical entities according to a preferred protocol with most preferred concentration levels and/or amounts according to a particular dosing schedule. The inventive compositions may be nutraceutical compositions.

The one or more fatty acids and fatty acid derivatives may be cancer metabolism disruptors. Cancer metabolism disruptors according to the invention may include, without limitations, disruptors of adenosine tri-phosphate (ATP) pathways and disruptors of bio-intermediate metabolic/catabolic pathways. According to certain embodiments, one or more atoms of the one or more fatty acids and fatty acid derivatives may be isotopic (e.g., radioactive isotopes for radiotherapy, or non-radioactive isotopes having an effect on drug metabolism, etc.).

A cancer metabolism disruptor according to embodiments of the inventive composition include, without limitation, at least one or more straight chain, branched chain, cycloalkanes, alkenyl chains, and alkyl chains; as well as alkenyl/alkyl alkanes or otherwise substituted carbon chains of 4-20 carbon units. Carbon chains may be saturated or unsaturated. Carbon chains may be in a cis- or trans-confirmation. Carbon substitutions with S, Si, or O within the chain length may also be present. Pendant substitutions may be included in certain embodiments of the inventive formulations, including but not limited to chiral substitutions such that the fatty acids/fatty acid derivatives are present as single stereoisomers or a combination thereof.

The fatty acid derivatives may include glycerides, fatty acid salts, hydroxy fatty acids, fatty acid amides of amino acids, and other fatty acid conjugates of amino acids. The fatty acid derivatives may be saturated or unsaturated, may have cis- or trans-configurations, and may also include modifications to the "end-cap" carboxyl of the fatty acid. The composition may include, without limitation, one or more of: oleic acid monoglycerides, palmitoleic acid monoglycerides, palmitic acid monoglycerides, lauric acid monoglycerides, myristate, linoleate, hexadecanoic acid, octanoic acid, and octadeconoic acid; moreover, the composition may include free fatty acid forms of these monoglycerides, pharmaceutically acceptable salts thereof, hydroxy fatty acids forms thereof, amides of amino acids of these fatty acids (such as, but without intent to limit, lysine, asparagine and arginine), amides of these fatty acids linked to various sugars via various linkages, and fatty acid esters of sucrose and other fatty acid sugar methyl esters. The fatty acids may be naturally occurring. Fatty acid derivatives/analogs may be naturally occurring or synthetic.

In preferred embodiments, the composition includes natural fatty acid and/or fatty acid analogs in a combination, without intent to limit, of one or more of: oleic acid monoglycerides, palmitoleic acid monoglycerides, palmitic acid monoglycerides, lauric acid monoglycerides, myristate, linoleate, hexadeconoic acid, octanoic acid and octadeconoic acid. Preferred embodiments may include combinations of free fatty acid forms of these monoglycerides, pharmaceutically acceptable salts thereof, hydroxy fatty acids forms thereof, amides of amino acids of these fatty acids (such as but without intent to limit lysine, asparagine and arginine), and fatty acid esters of sucrose and other fatty acid sugar methyl esters. The fatty acid derivative may be monolaurin (a glycerol mono-ester of the 12-chain saturated fatty acid C12:0 lauric acid).

Fatty acid derivatives according to embodiments herein may include fatty acids conjugated to sugars, amino acids, and/or peptides, either directly or via a glycerol moiety. The conjugation bonds may include ester linkages, amide linkages, methyl amide linkages, urethane linkages, triazole linkages, etc. without limitation.

In one embodiment, the one or more fatty acids and fatty acid derivatives are present in crystal, polymorph, co-crystal, and/or liquid crystal structures with a desired particle size, dissolution rate and bioavailability within the inventive composition. The choice of structure used is envisioned to be associated with dose response, pharmacokinetics, drug metabolism, and/or kinetics of offending cell death, which will require characterization by cell type and disease indication. Variability among indications, patients, and cell types, will also be considered as part of an overall personalized medicine approach to treatment as alluded to above.

In another embodiment, the composition comprises one or more glycerides. The glycerides may be mono-substituted, di-substituted, or tri-substituted. The glycerides may include monoglycerides. Hetero substitutions and linkage chemistries are envisaged in one embodiment of the invention.

In a preferred embodiment, carbon chains of the one or more fatty acids and fatty acid derivatives have from 4 to 20 carbons. In another embodiment, the composition may include one or more fatty acids conjugated to a glycerol via a first ester linkage, wherein the glycerol is further conjugated to at least one of a sugar or an amino acid via a second ester linkage. Alternatively, linkages may be hetero functional.

In another preferred embodiment, the composition further comprises one or more nucleosides and/or nucleoside precursors. For example, inosine is a nucleoside precursor in purine metabolism with putative neuroprotective/neuroregenerative and antiviral properties (DrugBank DB04335 v. 5.1.5 (1)). Studies of inosine and its analogs as anti-cancer agents and immunomodulators have led to paradoxical results depending on the conditions of study and cells used. In mono-layer cell culture conditions, the addition to media of adenosine or inosine has been shown to result in more rapid proliferation of cancer cells. However, cancer is a heterogeneous disease where agents may be multimodal with drug activity dependent on the site of delivery. Without being bound by theory, it is believed that inosine and its analogs can act as effective inhibitors of cancer cell proliferation when used in particular quantities and in a quantitative and stereochemically selective manner (e.g., wherein a stereo-selective method is applied to deaminating adenine analogs) (https://www.ncbi.nlm.nih.gov/pmc/articles/PMC5406388/).

Inosine and its analogs are alternative carbon supplies that support effector T-cell proliferation and antitumor function under glucose restriction, an effect which is noted to occur amongst many tumor types. A robust adaptive immune system requires effector T-cells to respond and adapt to fluctuations in environmental nutrient levels imposed in different tissues by disease. Such responsiveness and adaptation reflect metabolic plasticity, allowing T-cells to elicit immune functions using a wide range of nutrient substitutes. It is believed that inosine and its analogs may effectively enhance the antitumor efficacy of immune checkpoint blockade or adoptive T-cell transfer (https://www.biorxiv.org/content/10.1101/766642v1).

In yet a further preferred embodiment, the composition further comprises one or more sugars, fibrous carbohydrates, and/or fibers. For example, β-glucan is a source of soluble dietary fiber commonly used in nutraceuticals with immunomodulating properties.

β-glucans do not occur in the body (i.e., human or animal), but are naturally occurring polysaccharides present as constituent in cereal grains, mushrooms, fungi, and yeast. Preparations of β-glucans may be made for dietary or medical use from barley fiber, oats and whole grains, reishi, maitake and shiitake mushrooms, seaweed, and algae. Preparations of β-glucans may have a purity of 75% or greater. Sources of β-glucans include, but are not limited to, *Lentinula edodes, Lactobacillus plantarum, Lactobacillus acidophilus, Lactobacillus paracasei, Leuconostoc mesenteroides, Lactobacillus bulgaricus, Lactobacillus sasei, Lactobacillus salivarius, Pediococcus pentosaceus, Streptococcus thermophiles, Bacillus subtilis, Bacillus coagulans, Enteroccous faecium, Bifidobacterium bifidum, Bifidobacterium lactis (B. lactis), Bifidobacterium longum, Lactobacillus rhamnosus, Lactobacillus reuteri*, and *Bifidobacterium infantis*.

β-glucans may be present in biologically active extracts, including extracts derived from fungi. For example, bioactive fungal extracts (e.g., derived from one or more strains of *Lentinula edodes*) may include about 60-90% by weight carbohydrates. Such carbohydrates include polysaccharides in the form of α (1-4) glucans and β (1-3) glucans.

It is now well-established in the literature that β-glucans can confer to the immune system relative to cancer treatment, infection and immunity, and restoration of damaged bone marrow. It is believed that β-glucans help to activate immune cells and the triggering of a coordinated defense response against cancer cells, which may slow the growth of tumors and prevent metastatic lesions. Importantly, there is a biological role for beta glucan's in anti-metastatic activity that depending upon patient conditions a limited role or of more substantial activity. The latter situation, activating innate immune cells such as macrophages, dendritic cells, granulocytes, and natural killer cells, triggering the response of adaptive immune cells such as CD4, CD8, T cells and B cells leading to marked inhibition of tumor growth and metastases. Here too, mechanisms are likely to be multi modal and complex, even varying with the chemical structure, molecular weight, and source of the beta glucan (https://pubmed.ncbi.nlm.nih.gov/23140352/).

According to certain embodiments of the inventive composition, the compositions are formulated such that they demonstrate anti-cancer activity against cancer cells (e.g., cells that promote, cause, or support progression of disease cells), including the disruption of clusters of cancer and immune cells derived from the blood or other tissues of cancer patients. Anti-cancer activity may be measured by degrees of cell killing, cell cycle arrest, signaling disruption, and metabolic disruption using assays accepted in the art. In an embodiment of the composition, the cancer to be treated, prevented, or ameliorated by reducing, killing, or inhibiting proliferation of populations of cells associated with the metastatic progression of cancer in a cancer patient may be metastatic cancer.

In a further embodiment, the composition includes a concentration or amount of the one or more fatty acids and fatty acid derivatives that is therapeutically effective to kill a therapeutically significant number of invasive circulating tumor cells (iCTC) within the cancer patient. In a further embodiment, the composition includes one or more nucleosides and/or nucleoside precursors (e.g., inosine). In still a further embodiment, the composition includes one or more sugars, fibrous carbohydrates, and/or fibers (e.g., β-glucan). The β-glucan may be yeast β-glucan.

In a preferred embodiment of the composition, the composition includes monolaurin (also referred to as glycerol monolaurate) as the fatty acid derivative. Monolaurin possesses well-demonstrated antimicrobial properties in vitro. At concentrations equivalent to 36-73 μM, monolaurin also inhibits primary human T-cell signaling in vitro by destabilizing T-cell lipid dynamics and disrupting actin cytoskeletal arrangement to reduce activated T-cell adhesion. Further, when administered ad libitum between 400 and 1600 mg per kg mouse chow to 4-5 week-old male C57BL/6 mice, monolaurin enhanced the presence of beneficial gut microbes with only modest weight gain (an increase of 8-13% from 4-17 weeks) and without inflammation or dysregulated glucose and lipid metabolism. Consistent with this, unlike longer chain saturated fatty acids such as palmitate (C16:0) and stearate (C18:0), the monolaurin derivative lauric acid (dodecanoic acid) did not alter expression of PGC-1α (PPARγ coactivator 1α, a putative regulator of obesity and cholesterol homeostasis) in cultured C2C12 myotubes. Lauric acid has also been shown to inhibit proliferation, enhance apoptosis and/or synergize with cancer therapies directed against cancers from various tissue origins, including breast and colon cancers.

"Therapeutic/clinical significance" or "therapeutic/clinical effectiveness" is defined for amounts and concentrations of test articles as being able to kill about 20% or greater of the total cells associated with metastatic progression that are present prior to patient treatment (e.g., in ex vivo assays of iCTCs). Of greater "therapeutic significance" is greater than about 50% of the total cells present prior to treatment being killed. Of greatest "therapeutic significance" is greater than approximately 70% of the total cells present prior to patient treatment being eliminated—this "therapeutic significance" is most preferred. A "therapeutically/clinically effective" amount or concentration herein is sufficient to reduce/kill at least 20%, at least 25%, at least 30%, at least 35%, at least 40%, at least 45%, at least 50%, at least 55%, at least 60%, at least 65%, or at least 70% of the total cells associated with metastatic progression of cancer.

Post patient treatment resulting in a reduction in metastatic cancer-related cells (e.g., iCTCs) measured coincidentally with other measures of response, such as imaging or biomarkers, of greater than approximately 30% is most likely to be associated with a lesser but still therapeutically significant treatment response (i.e., the concentration(s) of bioactive ingredient(s) in compositions according to embodiments of the present invention are significant concentration(s) such that greater than about 30% of metastatic cancer-related cells (e.g., iCTC) are killed). Correlation with complete response, partial response or stable disease and progression will require retrospective analysis post clinical trial. Responses may be dependent on heterogeneity of cancer tumor cells and their sensitivity to drugs and compositions according to embodiments of the invention herein.

Clinically and/or therapeutically effective concentrations, or concentrations sufficient to kill cells associated with progression of metastatic cancer, of the one or more fatty acids and fatty acid derivatives according to embodiments herein may range from sub-micromolar to 100 μM, or greater. Clinically and/or therapeutically effective concentrations of the one or more fatty acids and fatty acid derivatives according to embodiments herein may range from sub-micromolar to 200 μM, or greater. Clinically and/or therapeutically effective concentrations of the one or more fatty acids and fatty acid derivatives according to embodiments herein may range from sub-micromolar to 300 μM, or greater.

In other embodiments, a clinically and/or therapeutically effective concentration, or a concentration sufficient to kill cells associated with progression of metastatic cancer, of the one or more fatty acids/fatty acid derivatives (e.g., monolaurin) is provided. In some embodiments, this effective concentration of the one or more fatty acids/fatty acid derivatives as measured in cell culture or liquid biopsy has an EC50 of <1 μM to about 250 μM, with a preferred embodiment have an EC50 of less than 100 μM. Effective concentrations of the one or more fatty acids/fatty acid derivatives may also include: about 0.0001 μM, about 0.001 μM, about 0.01 μM, about 0.1 μM, about 0.0002 μM, about 0.002 μM, about 0.02 μM, about 0.2 μM, about 0.0003 μM, about 0.003 μM, about 0.03 μM, about 0.3 μM, about 0.0004 μM, about 0.004 μM, about 0.04 μM, about 0.4 μM, about 0.0005 μM, about 0.005 μM, about 0.05 μM, about 0.5 μM, about 0.0006 μM, about 0.006 μM, about 0.06 μM, about 0.6 μM, about 0.0007 μM, about 0.007 μM, about 0.07 μM, about 0.7 μM, about 0.0008 μM, about 0.008 μM, about 0.08 μM, about 0.8 μM, about 0.0009 μM, about 0.009 μM, about 0.09 μM, about 0.9 μM, <1 μM, about 1 μM, about 10 μM, about 20 μM, about 30 μM, about 40 μM, about 50 μM, about 60 μM, about 70 μM, about 75 μM, about 80 μM, about 90 μM, about 100 μM, about 110 μM, about 120 μM, about 125 μM, about 130 μM, about 140 μM, about 150 μM, about 160 μM, about 170 μM, about 175 μM, about 180 μM, about 190 μM, about 200 μM, about 210 μM, about 220 μM, about 225 μM, about 230 μM, about 240 μM, about 250 μM, about 260 μM, about 270 μM, about 275 μM, about 280 μM, about 290 μM, about 300 μM, about 310 μM, about 320 μM, about 325 μM, about 330 μM, about 340 μM, about 350 μM, about 360 μM, about 370 μM, or about 375 μM.

A clinically or therapeutically effective concentration, or a concentration sufficient to kill cells associated with progression of metastatic cancer, of the one or more fatty acids (e.g., monolaurin) according to embodiments herein is in the range from about 0.0001 μM to about 375 μM, about 0.0002 μM to about 370 μM, about 0.0003 μM to about 360 μM, about 0.0004 μM to about 350 μM, about 0.0005 μM to about 340 μM, about 0.0006 μM to about 330 μM, about 0.0007 μM to about 325 μM, about 0.0008 μM to about 320 μM, about 0.0009 μM to about 310 μM, about 0.001 μM to about 300 μM, about 0.002 μM to about 290 μM, about 0.003 μM to about 280 μM, about 0.004 μM to about 275 μM, about 0.005 μM to about 270 μM, about 0.006 μM to about 260 μM, about 0.007 μM to about 250 μM, about 0.008 μM to about 240 μM, about 0.009 μM to about 230 μM, about 0.01 μM to about 225 μM, about 0.02 μM to about 220 μM, about 0.03 μM to about 210 μM, about 0.04 μM to about 200 μM, about 0.05 μM to about 190 μM, about 0.06 μM to about 180 μM, about 0.07 μM to about 175 μM, about 0.08 μM to about 170 μM, about 0.09 μM to about 160 μM, about 0.1 μM to about 150 μM, about 0.2 μM to about 140 μM, about 0.3 μM to about 130 μM, about 0.4 μM to about 125 μM, about 0.5 μM to about 120 μM, about 0.6 μM to about 110 μM, about 0.7 μM to about 100 μM, about 0.8 μM to about 90 μM, about 0.9 μM to about 80 μM, about 1 μM to about 75 μM, about 10 μM to about 70 μM, about 20 μM to about 60 μM, about 25 μM to about 50 μM, or about 30 μM to about 40 μM.

In yet another embodiment, a clinically or therapeutically effective concentration, or a concentration sufficient to kill cells associated with progression of metastatic cancer, of one or more fatty acids and/or fatty acid derivatives is present as a pharmaceutically acceptable isomeric mixture. The isomeric mixture may be a mixture of 1-, 3-, and the 2-isomers of monolaurin. The isomeric mixture of monolaurin may be in crystalline, liquid, or liquid crystal forms. The isomeric mixture may be an equal mixture of the 1-, 3- and the 2-isomers of monolaurin. The effective concentration of one or more fatty acids and fatty acid derivatives may include both monolaurin and additional glycerides, fatty acids, and/or fatty acid derivatives.

In certain embodiments of the composition, clinically or therapeutically effective concentrations, or concentrations sufficient to kill cells associated with progression of metastatic cancer, of one or more fatty acids and fatty acid derivatives in embodiments of the inventive formulations may be co-used or co-formulated with modulators of immune responsiveness, chemotherapeutics, other cancer metabolism disruptors, or inhibitors of cancer immune system avoidance. The one or more cancer metabolism disruptors, chemotherapeutics, and modulators of immune response, may be present in a concentration from less than 1 μM to about 200 μM in the inventive composition(s). Modulators of immune response may include stimulatory signal transduction modulators and activators of immune response. Modulators of immune response according to certain embodiments include, for example without intent to limit, 1-3 β-glucan, 1-6 β-glucan, analogs of β-glucan, selective stimulators of immune-cell associated phospholipase A2/phospholipase activators, chemokines, biological signal regulators, and neo-antigens. The one or more other cancer metabolism disruptors, chemotherapeutics, and modulators of immune response may comprise one or more naturally occurring or modified carbohydrates, amino acids, peptides, lipopolysaccharides, and analogs thereof (e.g., inosine). Modulators of immune response in the form of carbohydrates/modified carbohydrates may include β-glucan and analogs of β-glucan.

Embodiments of the inventive composition include one or more fatty acids/fatty acid derivatives (e.g., monolaurin), one or more nucleosides and/or nucleoside precursors (e.g., inosine), and one or more fibrous carbohydrates/fibers (e.g., β-glucan). In a preferred embodiment of the inventive composition, fatty acid derivative monolaurin, nucleoside precursor inosine, and soluble fiber yeast β-glucan are combined. The components may be combined at a w/w/w ratio of 1000:15:340 of monolaurin:inosine:β-glucan. The combination may be a suspension of monolaurin, inosine, and β-glucan.

Clinically or therapeutically effective concentrations, or concentrations sufficient to kill cells associated with progression of metastatic cancer, of the one or more fatty acids/fatty acid derivatives (e.g., monolaurin) in compositions according to the invention herein include the range from about 0.0001 µM to about 375 µM about 1 µM to about 350 µM, from about 10 µM to about 325 µM, from about 50 µM to about 300 µM, from about 1 µM to about 300 µM, from about 75 µM to about 275 µM, from about 100 µM to about 300 µM, from about 100 µM to about 250 µM, from about 150 µM to about 300 µM, from about 100 µM to about 200 µM, or from about 150 µM to about 200 µM.

In other embodiments of the inventive composition, a clinically or therapeutically effective concentration, or a concentration sufficient to kill cells associated with progression of metastatic cancer, of the one or more fatty acids/fatty acid derivatives (e.g., monolaurin) is 0.0001 µM, 0.001 µM, 0.01 µM, 0.1 µM, 0.0002 µM, 0.002 µM, 0.02 µM, 0.2 µM, 0.0003 µM, 0.003 µM, 0.03 µM, 0.3 µM, 0.0004 µM, 0.004 µM, 0.04 µM, 0.4 µM, 0.0005 µM, 0.005 µM, 0.05 µM, 0.5 µM, 0.0006 µM, 0.006 µM, 0.06 µM, 0.6 µM, 0.0007 µM, 0.007 µM, 0.07 µM, 0.7 µM, 0.0008 µM, 0.008 µM, 0.08 µM, 0.8 µM, 0.0009 µM, 0.009 µM, 0.09 µM, 0.9 µM, <1 µM, 1 µM, 10 µM, 20 µM, 30 µM, 40 µM, 50 µM, 60 µM, 70 µM, 75 µM, 80 µM, 90 µM, 100 µM, 110 µM, 120 µM, 125 µM, 130 µM, 140 µM, 150 µM, 160 µM, 170 µM, 175 µM, 180 µM, 190 µM, 200 µM, 210 µM, 220 µM, 225 µM, 230 µM, 240 µM, 250 µM, 260 µM, 270 µM, 275 µM, 280 µM, 290 µM, 300 µM, 310 µM, 320 µM, 325 µM, 330 µM, 340 µM, 350 µM, 360 µM, 370 µM, or 375 µM.

A clinically or therapeutically effective concentration, or a concentration sufficient to kill cells associated with progression of metastatic cancer, of the one or more fatty acids/fatty acid derivatives (e.g., monolaurin) according to embodiments of the composition herein is in the range from 0.0001 µM to 375 µM, 0.0002 µM to 370 µM, 0.0003 µM to 360 µM, 0.0004 µM to 350 µM, 0.0005 µM to 340 µM, 0.0006 µM to 330 µM, 0.0007 µM to 325 µM, 0.0008 µM to 320 µM, 0.0009 µM to 310 µM, 0.001 µM to 300 µM, 0.002 µM to 290 µM, 0.003 µM to 280 µM, 0.004 µM to 275 µM, 0.005 µM to 270 µM, 0.006 µM to 260 µM, 0.007 µM to 250 µM, 0.008 µM to 240 µM, 0.009 µM to 230 µM, 0.01 µM to 225 µM, 0.02 µM to 220 µM, 0.03 µM to 210 µM, 0.04 µM to 200 µM, 0.05 µM to 190 µM, 0.06 µM to 180 µM, 0.07 µM to 175 µM, 0.08 µM to 170 µM, 0.09 µM to 160 µM, 0.1 µM to 150 µM, 0.2 µM to 140 µM, 0.3 µM to 130 µM, 0.4 µM to 125 µM, 0.5 µM to 120 µM, 0.6 µM to 110 µM, 0.7 µM to 100 µM, 0.8 µM to 90 µM, 0.9 µM to 80 µM, 1 µM to 75 µM, 10 µM to 70 µM, 20 µM to 60 µM, 25 µM to 50 µM, or 30 µM to 40 µM.

Another clinically or therapeutically effective concentration, or a concentration sufficient to kill cells associated with progression of metastatic cancer, of the one or more fatty acids/fatty acid derivatives according to embodiments of the inventive composition herein is in the range from 0.0001 µM to 375 µM, 0.0001 µM to 375 µM 1 µM to 350 µM, from 10 µM to 325 µM, from 50 µM to 300 µM, from 1 µM to 300 µM, from 75 µM to 275 µM, from 100 µM to 300 µM, from 100 µM to 250 µM, from 150 µM to 300 µM, from 100 µM to 200 µM, or from 150 µM to 200 µM.

Clinically or therapeutically effective concentrations, or concentrations sufficient to kill cells associated with progression of metastatic cancer, of the cancer metabolism disruptors, chemotherapeutics, and/or modulators of immune response may be included in compositions according to the invention herein. For example, one or more naturally occurring or modified carbohydrates, amino acids, peptides, lipopolysaccharides, and analogs thereof (e.g., inosine), and/or modulators of immune response in the form of carbohydrates/modified carbohydrates (e.g., β-glucan and analogs of β-glucan) may be included in compositions according to the invention herein in the range from less than about 1 µM to about 200 µM, about 1 µM to about 200 µM, from about 10 µM to about 190 µM, from about 25 µM to about 175 µM, from about 50 µM to about 150 µM, from about 75 µM to about 125 µM, from about 1 µM to about 100 µM, from about 80 µM to about 120 µM, from about 25 µM to about 50 µM, from about 100 µM to about 200 µM, from about 150 µM to about 200 µM; about 0.1 µM to 150 µM, 0.2 µM to 140 µM, 0.3 µM to 130 µM, 0.4 µM to 125 µM, 0.5 µM to 120 µM, 0.6 µM to 110 µM, 0.7 µM to 100 µM, 0.8 µM to 90 µM, 0.9 µM to 80 µM, 1 µM to 75 µM, 10 µM to 70 µM, 20 µM to 60 µM, 25 µM to 50 µM, or 30 µM to 40 µM, about 1 µM, about 10 µM, about 25 µM, about 50 µM, about 75 µM, about 100 µM, about 125 µM, about 150 µM, about 175 µM, or about 200 µM.

Clinically or therapeutically effective amounts, or amounts sufficient to kill cells associated with progression of metastatic cancer, of the one or more fatty acids/fatty acid derivatives (e.g., monolaurin) in compositions according to the invention herein include from about 1 g to about 20 g per daily total dose, from about 1 g to about 15 g per daily total dose, from about 1 g to about 10 g per daily total dose, from about 1 g to about 5 g per daily total dose, about 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, about 15 g daily total dose, about 16 g daily total dose, about 17 g daily total dose, about 18 g daily total dose, about 19 g daily total dose, or about 20 g daily total dose.

In some embodiments of the composition, a clinically or therapeutically effective amount, or an amount sufficient to kill cells associated with progression of metastatic cancer, of monolaurin is included. The clinically or therapeutically effective amounts of monolaurin in compositions according to the invention herein include from about 1 g to about 20 g per daily total dose, from about 1 g to about 15 g per daily total dose, from about 1 g to about 10 g per daily total dose, from about 1 g to about 5 g per daily total dose, about 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, about 15 g daily total dose, about 16 g daily total dose, about 17 g daily total dose, about 18 g daily total dose, about 19 g daily total dose, or about 20 g daily total dose.

Clinically or therapeutically effective amounts, or amounts sufficient to kill cells associated with progression of metastatic cancer, of the cancer metabolism disruptors, chemotherapeutics, and/or modulators of immune response may be included in compositions according to the invention herein. For example, one or more naturally occurring or modified carbohydrates, amino acids, peptides, lipopolysaccharides, and analogs thereof (e.g., inosine), and/or modulators of immune response in the form of carbohydrates/modified carbohydrates (e.g., β-glucan and analogs of β-glucan) may be included in compositions according to the invention herein in the range from about 0.0001 g to about 15 g per daily total dose, from about 0.001 g to about 10 g per daily total dose, from about 0.01 g to about 5 g per daily total dose, from about 0.1 g to about 2.5 g per daily total dose, from about 1 g to about 1.5 g per daily total dose about 0.0001 g daily total dose, about 0.001 g daily total dose, about 0.01 g daily total dose, about 0.1 g daily total dose, 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, or about 15 g daily total dose.

Clinically or therapeutically effective amounts, or amounts sufficient to kill cells associated with progression of metastatic cancer, of modulators of immune response may be included in compositions according to the invention herein. For example, modulators of immune response in the form of one or more nucleosides and/or nucleoside precursors (e.g., inosine and analogs thereof) and/or one or more fibers/fibrous carbohydrates/modified carbohydrates (e.g., β-glucan and analogs of β-glucan) may be included in compositions according to the invention herein in the range from about 0.0001 g to about 15 g per daily total dose, from about 0.001 g to about 10 g per daily total dose, from about 0.01 g to about 5 g per daily total dose, from about 0.1 g to about 2.5 g per daily total dose, from about 1 g to about 1.5 g per daily total dose about 0.0001 g daily total dose, about 0.001 g daily total dose, about 0.01 g daily total dose, about 0.1 g daily total dose, 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, or about 15 g daily total dose.

Clinically or therapeutically effective amounts, or amounts sufficient to kill cells associated with progression of metastatic cancer, of inosine and analogs thereof may be included in compositions according to the invention herein. For example, inosine and/or analogs thereof may be included in inventive compositions according to embodiments herein in the range from about 0.0001 g to about 15 g per daily total dose, from about 0.001 g to about 10 g per daily total dose, from about 0.01 g to about 5 g per daily total dose, from about 0.1 g to about 2.5 g per daily total dose, from about 1 g to about 1.5 g per daily total dose about 0.0001 g daily total dose, about 0.001 g daily total dose, about 0.01 g daily total dose, about 0.1 g daily total dose, 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, or about 15 g daily total dose.

In some embodiments of the composition, a clinically or therapeutically effective amount, or an amount sufficient to kill cells associated with progression of metastatic cancer, of inosine is included. The clinically or therapeutically effective amounts of inosine in compositions according to the invention herein include from about 1 g to about 15 g per daily total dose, from about 0.0001 g to about 15 g per daily total dose, from about 0.001 g to about 10 g per daily total dose, from about 0.01 g to about 5 g per daily total dose, from about 0.1 g to about 2.5 g per daily total dose, from about 1 g to about 1.5 g per daily total dose about 0.0001 g daily total dose, about 0.001 g daily total dose, about 0.01 g daily total dose, about 0.1 g daily total dose, 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, or about 15 g daily total dose.

Clinically or therapeutically effective amounts, or amounts sufficient to kill cells associated with progression of metastatic cancer, of β-glucan and analogs of β-glucan may be included in compositions according to the invention herein. For example, β-glucan and/or analogs of β-glucan may be included in inventive compositions according to embodiments herein in the range from about 0.0001 g to about 15 g per daily total dose, from about 0.001 g to about 10 g per daily total dose, from about 0.01 g to about 5 g per daily total dose, from about 0.1 g to about 2.5 g per daily total dose, from about 1 g to about 1.5 g per daily total dose about 0.0001 g daily total dose, about 0.001 g daily total dose, about 0.01 g daily total dose, about 0.1 g daily total dose, 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, or about 15 g daily total dose.

In some embodiments of the composition, a clinically or therapeutically effective amount, or an amount sufficient to kill cells associated with progression of metastatic cancer, of β-glucan is included. The clinically or therapeutically effective amounts of β-glucan in compositions according to the invention herein include from about 1 g to about 15 g per daily total dose, from about 0.0001 g to about 15 g per daily total dose, from about 0.001 g to about 10 g per daily total dose, from about 0.01 g to about 5 g per daily total dose, from about 0.1 g to about 2.5 g per daily total dose, from about 1 g to about 1.5 g per daily total dose about 0.0001 g daily total dose, about 0.001 g daily total dose, about 0.01 g daily total dose, about 0.1 g daily total dose, 1 g daily total dose, about 2 g daily total dose, about 3 g daily total dose, about 4 g daily total dose, about 5 g daily total dose, about 6 g daily total dose, about 7 g daily total dose, about 8 g daily total dose, about 9 g daily total dose, about 10 g daily total dose, about 11 g daily total dose, about 12 g daily total dose, about 13 g daily total dose, about 14 g daily total dose, or about 15 g daily total dose.

Compositions according to embodiments of the invention may include combinations of components each in clinically or therapeutically effective amounts. For example, in some compositional embodiments, each of one or more fatty acids/fatty acid derivatives, one or more modulators of immune response in the form of one or more nucleosides and/or nucleoside precursors (e.g., inosine and analogs thereof), and modulators of immune response in the form of one or more fibers/fibrous carbohydrates/modified carbohydrates (e.g., β-glucan and analogs of β-glucan) may be included in therapeutically effective amounts in composition.

In a preferred embodiment, a composition for treating, preventing proliferation of, and/or killing cells associated with metastatic cancer progression in a cancer patient in need thereof, the composition comprises an amount of one or more of fatty acids and fatty acid derivatives, the fatty acid derivatives comprising glycerides, fatty acid salts, hydroxy fatty acids, and fatty acid amides of amino acids, that is effective to treat, prevent proliferation of, and/or kill cells associated with metastatic cancer progression; and further comprises an amount of one or more cancer metabolism disruptors, chemotherapeutics, and modulators of immune response, the modulators of immune response including stimulatory signal transduction modulators and activators of immune response, that is effective to treat, prevent proliferation of, and/or kill cells associated with metastatic cancer progression.

In particular embodiments, components of the inventive compositions may be combined at a w/w/w ratio of 1000:15:340 of fatty acid/fatty acid derivative:immune modulating nucleoside/nucleoside precursor:immune modulating fibrous carbohydrates/fibers. In preferred embodiments, the composition may include components combined at a w/w/w ratio of 1000:15:340 of monolaurin:inosine:β-glucan. Ranges of w/w/w ratios range from 1:1:1 monolaurin:inosine:β-glucan (equal amounts of each) to 100:5:5, to 100:10:50, and any range empirically determined to be effective in killing cells associated with the progression of cancer may be present within the invention compositions.

In yet another embodiment of the inventive composition, the composition includes one or more fatty acids and/or fatty acid derivatives as a pharmaceutically acceptable isomeric mixture. The isomeric mixture may be a mixture of 1-, 3-, and the 2-isomers of monolaurin. The isomeric mixture of monolaurin may be in crystalline, liquid, or liquid crystal forms. The isomeric mixture may be an equal mixture of the 1-, 3- and the 2-isomers of monolaurin. The clinically or therapeutically effective concentration or amount of one or more fatty acids and fatty acid derivatives may include both monolaurin and additional glycerides, fatty acids, and/or fatty acid derivatives.

In an embodiment, a concentration of monolaurin may be used in combination with modulators of immune responsiveness, chemotherapeutics, cancer metabolism disruptors, or inhibitors of cancer immune system avoidance. In yet another embodiment, the composition includes one or more substituted forms of monolaurin (e.g., 2-monolaurin), and one or more modulators of immune response in the form of carbohydrates.

Differences in blood and tumor levels of adenosine deaminase can effect local tumor adenosine levels and protect against a tumor localized immune response. This can occur even when plasma levels of enzyme are paradoxically elevated. Adenosine is toxic to immune cells that would recognize and invade a tumor. Londoño-R, Luz Marina, et al. "Abstract 1755: PEGylated Adenosine Deaminase (ADA2) Prevents Adenosine-Mediated Increase in Tumor Growth and Improves Antitumor Immune Responses," Cancer Research, American Association for Cancer Research, 1 Jul. 2018, cancerres.aacrjournals.org/content/78/13_Supplement/1755. Thus, other embodiments of the inventive composition herein may include, as an example of an agent intended to diminish inhibition of immune response by cancer and associated cells, adenosine deaminase or PEGylated adenosine deaminase for reduction of adenosine blood levels.

Without further intent to limit, ratios of isomers and components within embodiments of the composition can be adjusted to meet therapeutic need. "Therapeutic need" is determined with respect to the greatest likelihood of patient benefit, and can be defined as the amount necessary to result in broadest scope of cancer cell-type kill, in disruption of cancer-causing clusters, and in immune protection to maximize progression-free survival ("PFS") and overall survival.

Compositions according to certain embodiments herein may be formulated as solid or liquid dosage forms. Dosage forms may be configured for parenteral and/or non-parenteral administration. Fatty acids and/or fatty acid derivatives may be co-compounded or otherwise formulated for use in combination protocols with suitable modulators of immune responsiveness, chemotherapeutics, other cancer metabolism disruptors, or inhibitors of cancer immune system avoidance for co-dosing administration/delivery in an acceptable dosage form. Fatty acids and/or fatty acid derivatives may be co-formulated for use in combination protocols with suitable modulators of immune responsiveness, chemotherapeutics, other cancer metabolism disruptors, or inhibitors of cancer immune system avoidance for oral administration/delivery. Dosage forms may be formulated for oral delivery. Oral delivery methods for compositions according to certain embodiments of the invention herein may include tablets, capsules, liquids, chewables, soft gels, sachets, powders, syrups, liquid suspensions, emulsions, or other solutions.

Embodiments of the compositions herein are suitable for treatment, prevention, or amelioration of cancer in cancer patients as single therapeutic agents or in combination with other therapeutic intervention modalities such as chemotherapy, surgery, targeted therapies, and radiation.

Embodiments of the composition are formulated for the treatment of metastatic cancers and cancer causing cells circulating in the blood of mammalian patients.

II. Methods

In yet another embodiment, a method for treating metastatic cancer by killing cells associated with metastatic cancer progression in a cancer patient is provided. The method comprises administering to the cancer patient in need thereof a concentration of one or more fatty acids and fatty acid derivatives. The fatty acid derivatives include glycerides, pharmaceutically acceptable fatty acid salts, hydroxy fatty acids, and fatty acid amides of amino acids. The administered concentration is sufficient to treat the metastatic cancer in the cancer patient.

In a further embodiment, the method includes administering any composition set forth above according to any pharmaceutically acceptable dosing regimens and in any pharmaceutically suitable formulation. Particular embodiments of the method include administering glycerides, and more particularly, monoglycerides (e.g., monolaurin). In yet other embodiments, the method comprises administering one or more cancer metabolism disruptors, chemotherapeutics, and modulators of immune response.

The compositions may be administered, by any suitable administration method, to a patient in need thereof at a total daily dose of from about 1 g to about 20 g. In certain embodiments, the total daily dose administered is from about 2.5 g to about 15 g, from about 5 g to about 10 g, from about 2.5 g to about 7.5 g, or from about 3 g to about 6 g. The total daily dose administered may be about 1 g, about 2 g, about 3 g about 4 g about 5 g, about 6 g about 7 g about 8 g about 9 g about 10 g, about 1 g about 12 g about 13 g about 14 g about 15 g about 16 g about 17 g about 18 g about 19 g, or about 20 g. The total daily dose may be administered in a single dose, or may comprises multiple doses throughout the day. The compositions may include any pharmaceutically acceptable excipient or carrier.

In preferred embodiments of the inventions set forth herein, a total daily dose of about 3 g to about 6 g is administered orally to a patient in need thereof, wherein the bioactive components of the composition are monolaurin, inosine, and β-glucan, and wherein these components are combined at a w/w/w ratio of 1000:15:340, respectively. However, the bioactive components of the inventive composition may be combined at any suitable w/w/w ratio as set forth previously. The total daily dose may be administered in a single dose, or may comprises multiple doses throughout the day. In preferred embodiments, the total daily dose is comprised of multiple administrations per day.

A "therapeutically/clinically effective amount," or an amount sufficient to kill cells associated with progression of metastatic cancer, of compositions according to embodiments herein may include a total daily dose of from about 1 g to about 20 g. In certain embodiments, the "therapeutically effective amount" of an inventive composition herein is a total daily dose from about 2.5 g to about 15 g from about 5 g to about 10 g, from about 2.5 g to about 7.5 g or from about 3 g to about 6 g. The "therapeutically effective amount" may be a total daily dose of about 1 g, about 2 g about 3 g about 4 g, about 5 g, about 6 g about 7 g, about 8 g, about 9 g, about 10 g about 11 g, about 12 g, about 13 g about 14 g about 15 g, about 16 g, about 17 g, about 18 g, about 19 g, or about 20 g. The "therapeutically effective amount" may be administered in a single dose, or may comprises multiple doses throughout the day to reach a total daily dose. These "therapeutically effective" amounts have a therapeutic effectiveness or significance defined as at least 20%, at least 25%, at least 30%, at least 35%, at least 40%, at least 45%, at least 50%, at least 55%, at least 60%, at least 65%, or at least 70% reduction in total cells associated with metastatic progression of cancer. The compositions may include any pharmaceutically acceptable excipient or carrier.

In preferred embodiments of the inventions set forth herein, a "therapeutically/clinically effective amount," or an amount sufficient to kill cells associated with progression of metastatic cancer, comprising a total daily dose of about 3 g to about 6 g is administered orally to a patient in need thereof, wherein the bioactive components of the composition are monolaurin, inosine, and β-glucan, and wherein these components are combined at a w/w/w ratio of 1000: 15:340, respectively. However, the bioactive components of the inventive composition may be combined at any suitable w/w/w ratio as set forth previously. The total daily dose may be administered in a single dose, or may comprises multiple doses throughout the day. In preferred embodiments, the total daily dose is comprised of multiple administrations per day.

In some embodiments of the method for treating metastatic cancer in a cancer patient set forth herein, solid or liquid dosage forms of suitable compositions are administered. Dosage forms may be configured for parenteral and/or non-parenteral administration. Administered fatty acids and/or fatty acid derivatives may be co-compounded or otherwise formulated for use in combination protocols with suitable modulators of immune responsiveness, chemotherapeutics, other cancer metabolism disruptors, or inhibitors of cancer immune system avoidance for co-dosing administration/delivery in an acceptable dosage form. Fatty acids and/or fatty acid derivatives may be co-formulated for use in combination protocols with suitable modulators of immune responsiveness, chemotherapeutics, other cancer metabolism disruptors, or inhibitors of cancer immune system avoidance for oral administration/delivery. Methods may include acute and/or chronic dosing regimens, and in particular embodiments, daily dosing/administration. Methods of treating metastatic cancer may be configured to achieve, extend, or improve upon responses to standard of care treatment.

In one embodiment there is a method for preventing relapse of a cancer in a cancer patient by killing cells associated with metastatic cancer progression. The method comprises administering to the cancer patient in need thereof a concentration of one or more fatty acids and fatty acid derivatives. The fatty acid derivatives include glycerides, pharmaceutically acceptable fatty acid salts, hydroxy fatty acids, and fatty acid amides of amino acids. The administered concentration is sufficient to treat the metastatic cancer in the cancer patient. The fatty acid derivative may be monolaurin (a glycerol mono-ester of the 12-chain saturated fatty acid C12:0 lauric acid).

In one embodiment, the cancer for which relapse is prevented is metastatic cancer.

In a further embodiment, the method includes administering any composition set forth above according to any pharmaceutically acceptable dosing regimens and in any pharmaceutically suitable formulation. Particular embodiments of the method include administering glycerides, and more particularly, monoglycerides (e.g., monolaurin). In yet other embodiments, the method comprises administering one or more cancer metabolism disruptors, chemotherapeutics, and modulators of immune response.

In some embodiments of the method for preventing relapse of a cancer in a cancer patient set forth herein, solid or liquid dosage forms of suitable compositions are administered. Dosage forms may be configured for parenteral and/or non-parenteral administration. Administered fatty acids and/or fatty acid derivatives may be co-compounded or otherwise formulated for use in combination protocols with suitable modulators of immune responsiveness, chemotherapeutics, other cancer metabolism disruptors, or inhibitors of cancer immune system avoidance for co-dosing administration/delivery in an acceptable dosage form. Fatty acids and/or fatty acid derivatives may be co-formulated for use in combination protocols with suitable modulators of immune responsiveness, chemotherapeutics, other cancer metabolism disruptors, or inhibitors of cancer immune system avoidance for oral administration/delivery. In a preferred embodiment of the inventive method, fatty acid derivative monolaurin, nucleoside precursor inosine, and soluble fiber yeast β-glucan are combined and administered. The components may be administered at a w/w/w ratio of 1000:15:340 of monolaurin:inosine:β-glucan. The combination may be administered as a suspension of monolaurin, inosine, and β-glucan.

Methods may include acute and/or chronic dosing regimens, and in particular embodiments, daily dosing/administration. Methods of treating metastatic cancer by killing cells associated with cancer progression may be configured to achieve, extend, or improve upon responses to standard of care treatment. Administration during methods according to certain embodiments of the invention herein may be formulated for oral delivery. Oral delivery methods for compositions according to certain embodiments of the invention herein may include tablets, capsules, liquids, chewables, soft gels, sachets, powders, syrups, liquid suspensions, emulsions, or other solutions.

In a preferred embodiment, a method for treating, preventing proliferation of, or killing cells associated with metastatic progression of cancer in a cancer patient is provided, wherein the method comprises administering to the cancer patient in need thereof an amount of one or more fatty acids and fatty acid derivatives, wherein the fatty acid derivatives comprise glycerides, pharmaceutically acceptable fatty acid salts, hydroxy fatty acids, and fatty acid amides of amino acids. The amount of the one or more fatty acids and fatty acid derivatives is effective to treat, prevent proliferation of, and/or kill cells associated with metastatic cancer progression. The method also comprises administering to the cancer patient an amount of one or more cancer metabolism disruptors, chemotherapeutics, and modulators of immune response, the modulators of immune response including stimulatory signal transduction modulators and activators of immune response, wherein the amount of one or more cancer metabolism disruptors, chemotherapeutics, and modulators of immune response is effective to treat, prevent proliferation of, and/or kill cells associated with metastatic cancer progression.

Choice of specific fatty acid/derivatives and other components, ratios thereof, and therapeutic target concentrations are selected on the basis of ability (potency) to kill a sufficiently broad scope of patient derived diseased, or disease causing cells, as determined in a suitable solid or liquid biopsy assay such as circulating tumor cells and primary-metastatic lesion cells, so as to promote an optimum response. Such response is to be evaluated in cell culture conditions using patient derived CTC for the ability to provide sufficient kill capability using a selected panel of control cell lines. Characterization of cell types and differences to test article responses are contemplated for specific compositions and dosing matching laboratory test results with patient treatment. Confirmation of activity in patients against circulating tumor cells to be confirmed by additional blood collection, characterization of circulating tumor cell populations and any changes in sensitivity to the test articles or their combinations being considered during the course of treatment. Further assays of bioavailability, by route of administration, pharmacokinetics, dose relationship of kinetics of cell kill and other factors related to ADME evaluated in animal models according to the art are anticipated to further inform regarding selection of composition and dosing protocol design for development of treatments for the desired indication. That test articles are taken up into the target cells and delivered at appropriate levels to the desired targets as well as identification and confirmation of targets, receptors and transporters being available throughout the course of disease will require additional evaluation.

III. Examples

1. Monolaurin Anti-iCTC Activity Measured in Pancreatic Cancer Blood Samples Using the Vitatex Inc. Methods for Single iCTC and Clusters of iCTCs Project 1 Study-Pancreatic Cancer

TABLE 1

Record of The Project 1 Study-Pancreatic Cancer

| Purpose | CTC-Tx ®: iCTC drug response testing ex vivo (CDR) using therapeutic agents. Prepare/store up to 16-mL plasma. |
|---|---|
| Record Equipment | BD caliber 4-channel flow cytometer |
| Data Analysis | FlowJo V10 |
| Document name | The Project_1 final report-Pancreatic cancer_R1 |

TABLE 2

Extracted samples for Project 1 Study-Pancreatic Cancer

| Lab ID | Patient ID | Sample ID | Primary Diagnosis | Blood Volume (mL) | Plasma Volume (mL) | Plasma Tubes Stored |
|---|---|---|---|---|---|---|
| RP01 | 120651224 | BBW1000-SCI206512240 81417NH | Pancreatic Cancer | 34 | 14 | 4 |
| RP03 | 120813946 | BBW1000-O11208139460 82117NH | Pancreatic Cancer | 37 | 15 | 4 |
| RP04 | 120814116 | BBW1000-O11208141160 82217NH | Pancreatic Cancer | 35 | 8 | 2 |
| RP10 | 120827627 | BBW1000-C81208276270 91417NH | Pancreatic Cancer | 35 | 12 | 4 |
| RP11 | 120785056 | BBW1000-SC1207850560 91817NH | Pancreatic Cancer | 28 | 12 | 4 |
| RP12 | 120810746 | BBW1000-A11208107460 91817NH | Pancreatic Cancer | 36 | 16 | 4 |
| RP14 | 120813160 | BBW1000-SC1208131600 92117NH | Pancreatic Cancer | 26 | 16 | 4 |
| RP16 | 120810746 | BBW1000-A11208107460 92517N11 | Pancreatic Cancer | 36 | 16 | 4 |
| RP17 | 120703543 | BBW1000-A11207035430 92617NH | Pancreatic Cancer | 36 | 16 | 4 |
| RP18 | 120812486 | BBW1000-A11208124860 92717NH | Pancreatic Cancer | 36 | 14 | 4 |
| RP22 | 120851527 | BBW1000-A61208515271 01217NH | Pancreatic Cancer | 36 | 16 | 4 |

Materials for Project 1 Study-Pancreatic Cancer
Blood collection tubes: BD Vacutainer® 10 mL sodium heparin tube (BD catalog #367874)).
Vita-Assay™ AN6W plate.
Blood: pancreatic cancer, up to 40-mL blood collected from patients and provided by Conversant Bio.
Stock solution and dilutions
  Monolaurin 4.78 mM with 0.75% PS-80 (Stock Solution C), 13.1 mg monolaurin in 0.25 mL PS-80 and 0.75 mL water and 0.1 mL of this solution was diluted with 0.9 mL of RPMI. Stocks are stable for 2 weeks at 4 degrees C. Monolaurin used is an equal mixture of 1-, 2-, and 3-isomers of monolaurin.
  Monolaurin dilution: add 209.2 uL, 627.6 uL, and 1.2552 mL of monolaurin in 0.75% PS-80 (Stock solution C), and dilute to 10 mL of media to achieve final concentrations of 100 uM, 200 uM, 300 uM as indicated.

With respect to FIG. 1, a depiction of a generalized experimental scheme for testing efficacy of a composition in accordance with an exemplary embodiment of the present invention against iCTC from the blood of pancreatic cancer patients is shown. Invasive circulating tumor cells (iCTCs) were obtained from venous blood of the individual with advanced pancreatic cancer, cultured and exposed to a specific drug or battery of drugs at 1×, 2×, and 3× concentrations in vitro for 3 days. Drug responsiveness was measured by automatic flow cytometry using the reduction of live iCTCs in the treated samples from the number of live iCTCs in the untreated controls. The greater the reduction of iCTCs of a given drug at a given dose indicates greater responsiveness to that dose of the drug. Four AN6W plates were used for each sample. Control and drug at each dose in triplicate were incubated for 72 hours. The iCTCs were measured by flow cytometry and viewed by microscopy as described. The complete culture medium contains 10% fetal bovine serum.

Figure 2:
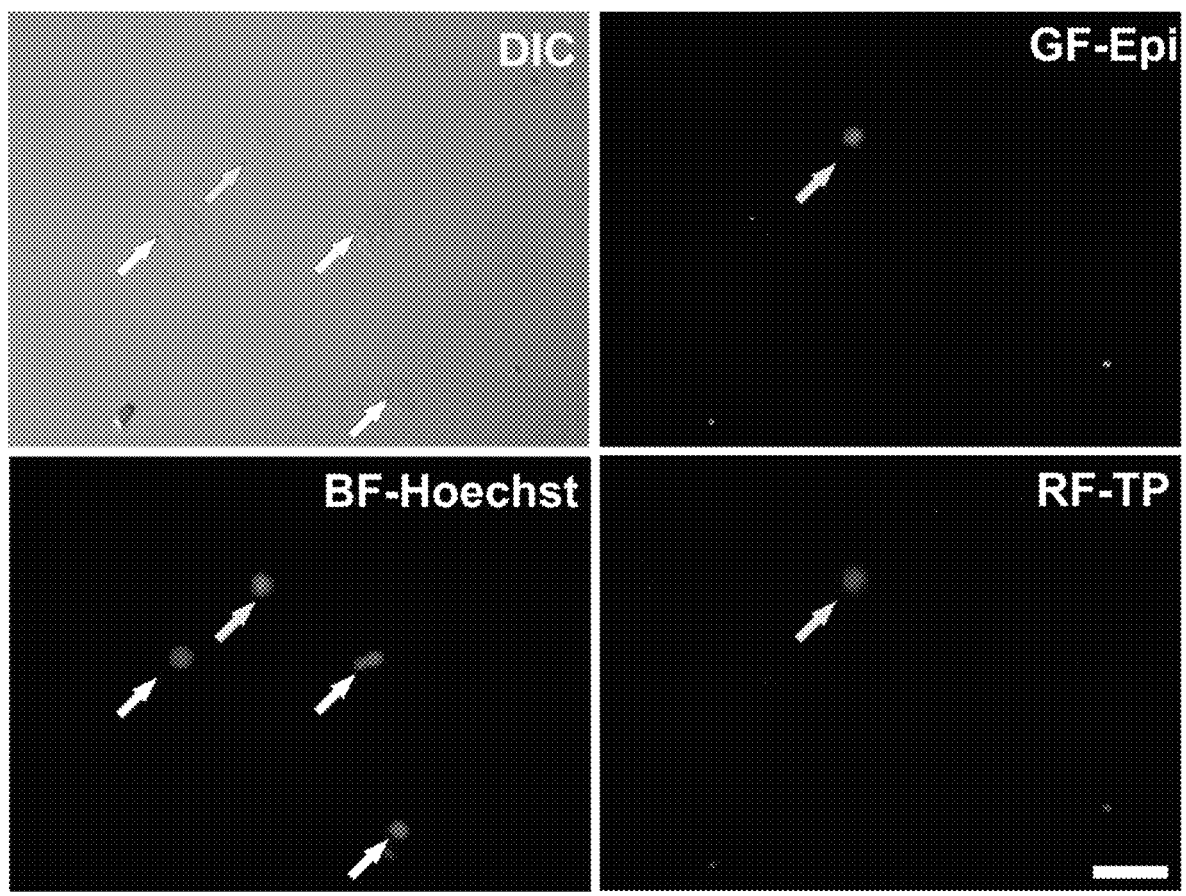
FIG. 2 is a depiction of phenotypic features of solitary iCTCs cultured for 7 days after isolation from a blood sample obtained from a pancreatic cancer patient. Specific markers in four optics of the same field are shown.
Figure 3:
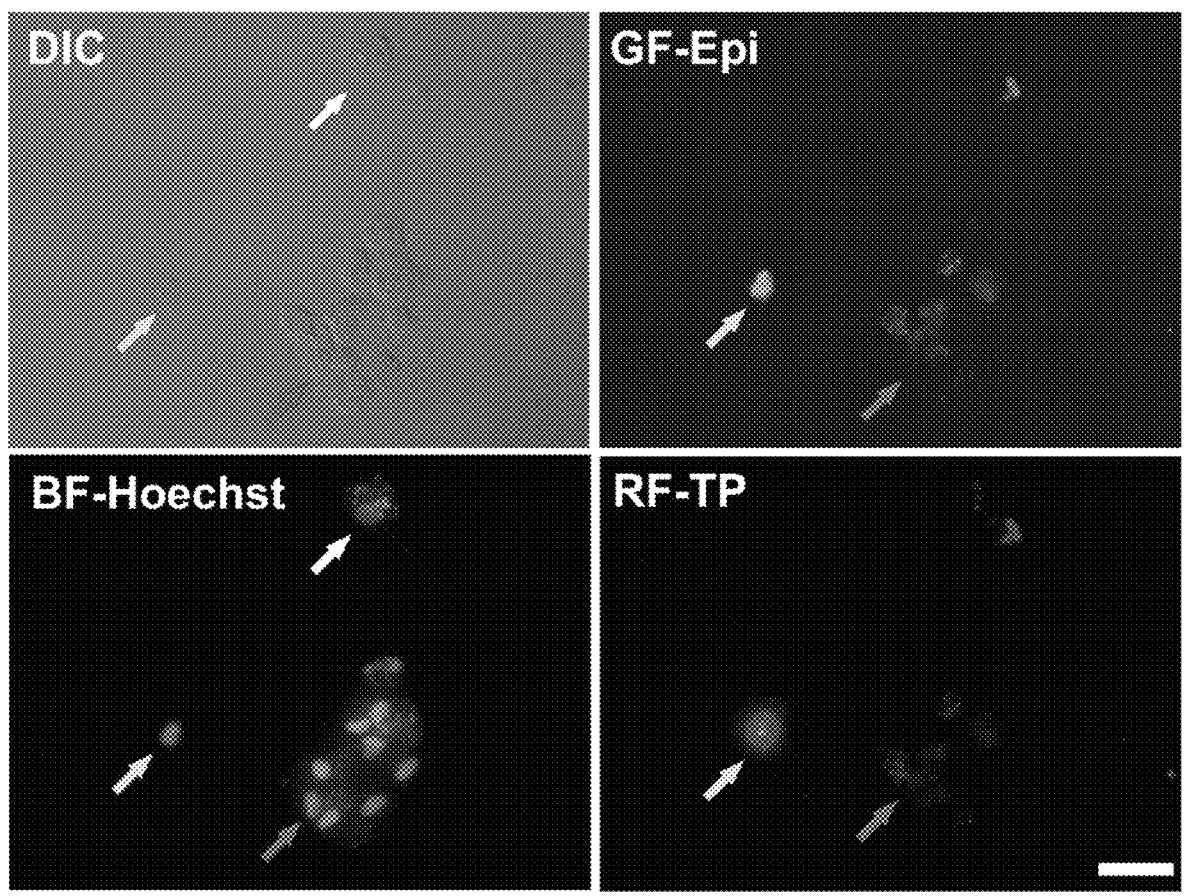
FIG. 3 is a depiction of phenotypic features of solitary and clustered iCTCs cultured for 7 days from the pancreatic cancer sample described with reference to FIG. 2, with specific markers in four optics of the same field.
Figure 4:
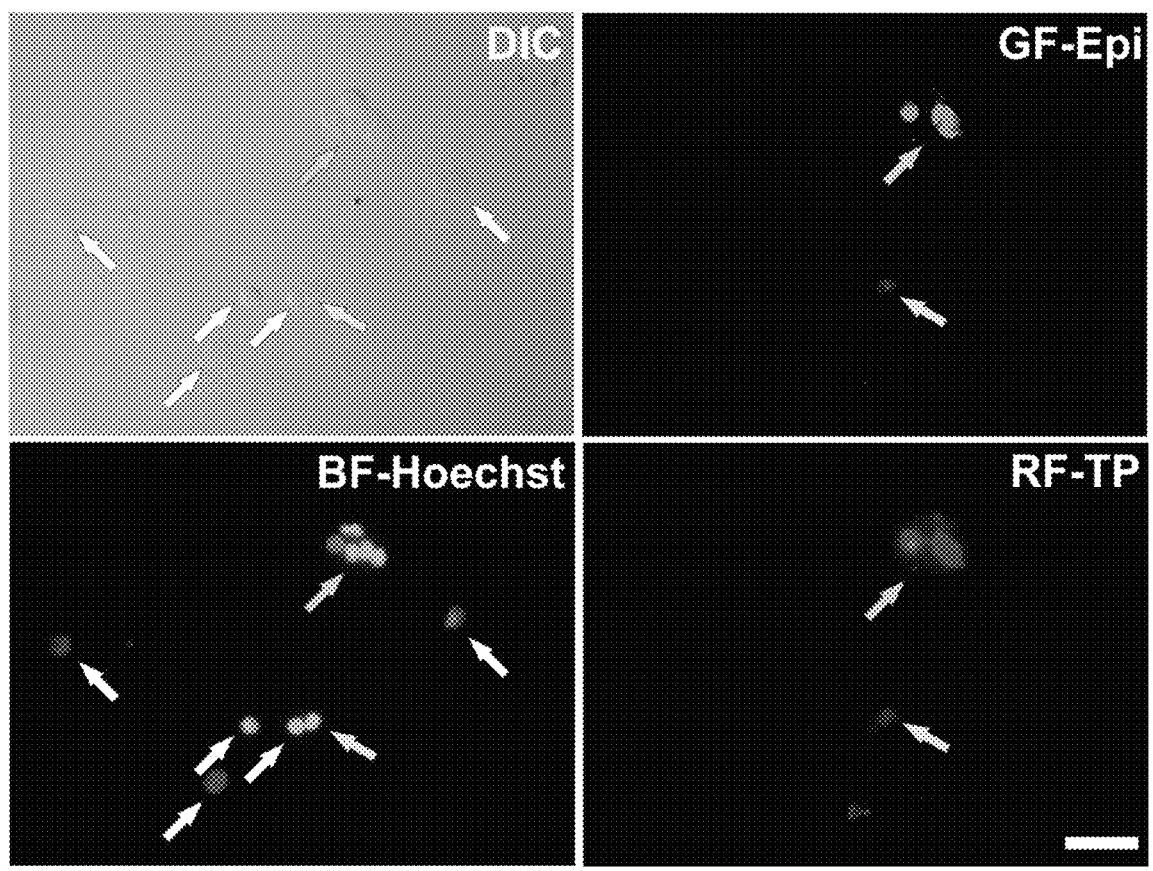
FIG. 4 is a depiction of phenotypic features of solitary and clustered iCTCs cultured for 3 days from an additional pancreatic cancer patient (i.e., a different patient from that patient described with reference to FIGS. 2 and 3) with specific markers in four optics of the same field.

The complete experimental procedure for Project 1 Study-Pancreatic Cancer, with reference to FIG. 1, is as follows:
1. Blood collection: up to 40-mL of blood was collected in several sodium heparin tubes from each patient.
2. Plasma collection: The patient sample tubes were pooled into a clean 50-mL conical tube and spun at 1,500 rpm for 8 mins at room temperature to separate plasma from blood cells. 3-4 mL of plasma were then collected into a clean 4.5-mL cell-frozen vial (up to 4 vials per patient), a labeled attached and the plasma stored at −80° C. freezer for use.
3. Calculated 50-mL tubes required for lysis of red blood cells: original blood volume. i.e., 36-mL,/2-mL=18.
4. Aliquotted 1/18 the remaining cell fraction into 18 new 50-mL tubes.
5. Red cell lysis: Added 48-mL of 1× red cell lysis buffer into each 50-mL tube to lyse red cells. Tubes placed on a roller mixer at 20-25° C. for 5 min. Cells spun down using low speed centrifugation (1,000 rpm).
6. iCTCs were captured using AN6W plate with or without drug treatment.
7. Drug treatment: Add 1-mL of CTC Capture Medium (standard culture medium containing 10% serum) with or without drugs (3× strength) to each 2-mL of the cell suspension in one well of the AN6W plate.
8. Cell culture: Culture cells in a 5% $CO_2$ incubator at 37° C. for overnight, 72 hours, and 7 days.
9. CAM-enzyme elution of CAM-captured cells: Wells will be washed twice using 2-mL of 1×PBS. Add 0.8-mL of the activated CAM enzyme working solution into the well, and place at 37° C. for 15 min. Transfer cell suspension into a 15-mL conical centrifuge tube. Wash well by pipetting 2-mL of 1×PBS into the well and collect/transfer wash solution into the pool cell suspension. CAM-captured tumor cells will be collected using low speed centrifugation (1,000 rpm) of the conical tube.
10. Preparation of the cells for flow cytometry: Fix the cells by using 1×BD cell fixing buffer and keep at room temperature for 5 min. Add 3-mL of 1×PBS (containing 0.2% BSA buffer), spin down cells and remove the supernatant.
11. Staining cells for flow cytometry: 20-μL of Vitatex mAb cocktail (CD45-APC, TP-PE, EPI-FITC, 7-AAD) is added into fixed cells with 1:5 dilution (20-μL to 100-μL) using 1×PBS with 0.2% BSA. Staining mix is kept in dark at 20-25° C. for 30 min. After staining, add 3-mL PBS with 0.2% BSA and pellet cells by centrifugation at 1,000 rpm for 5 minutes. Remove supernatant and retain ~500 μL of the stained cells. If desired break potential cellular clusters by pipetting 5 times using 200-uL pipette tips. Filter cells using cell-strainer tube (BD Falcon).
12. With reference to FIGS. 2, 3, and 4: Flow cytometry evaluation: Count tumor cells and immune cells by using a 4-channel (FITC, PE, APC, and 7AAD) flow cytometer. iCTC is defined as: $EPI^+TP^+CD45^-7AAD^+$ FIG. 2 depicts images of solitary iCTCs with specific markers in a cytospin preparation of the RP-17 sample. Yellow arrows indicate a single iCTC cell recovered by Vita-Assay™ that exhibits phenotypic features for visualized cells in four optics of the same field. A tumor cell is positively stained with green fluorescence-epithelial marker (GF-Epi), blue fluorescence nucleic acid dye (BF-Hoechst) and red fluorescence tumor progenitor (TP) marker (RF-TP). White arrows indicate WBCs that were not stained by Epi and TP tumor markers. Bar=40 μm. Note that cells from RP-17 were cultured for 7 days before staining.

FIG. 3 depicts images of solitary and clustered iCTCs with specific markers in a cytospin preparation of the RP-17 sample. Solitary iCTCs (yellow and white arrows) and clusters of iCTCs (red arrows) recovered by Vita-Assay™ that exhibit their phenotypic features in four optics of the same field. iCTCs are positively stained with green fluorescence-epithelial marker (GF-Epi), blue fluorescence nucleic acid dye (BF-Hoechst) and red fluorescence tumor progenitor (TP) marker (RF-TP). Bar=40 μm. Note that cells from RP-17 were cultured for 7 days before staining.

FIG. 4 depicts images of solitary and clustered iCTCs with specific markers in a cytospin preparation of the RP-22 sample. Yellow arrows indicate a single iCTC cell recovered by Vita-Assay™ that exhibits their phenotypic features in four optics of the same field. Pink arrows indicated iCTC clusters. A tumor cell is positively stained with green fluorescence-epithelial marker (GF-Epi), blue fluorescence nucleic acid dye (BF-Hoechst) and red fluorescence tumor progenitor (TP) marker (RF-TP). White arrows indicate WBCs that were not stained by Epi and TP tumor markers. Bar=40 μm. Note that cells from RP-22 were cultured for 3 days before staining.

13. Analyze data: Flowjo V10 software.

Summary of Project 1 Study-Pancreatic Cancer: With reference to Table 3 below, the in vitro iCTC drug response (CDR) assays, designed to assist with the selection of potential low toxicity drugs for the treatment of cancer in individuals based on the response of individual patient-derived iCTCs to specific therapeutic agents in preclinical studies, demonstrated high kill rates of iCTCs from pancreatic cancer patients using the formulation of monolaurin comprising an equal mixture of 1-, 2-, and 3-isomers of monolaurin.

TABLE 3

Results for Project 1 Study-Pancreatic Cancer
Metastatic Pancreatic stage III-IV

| Patient ID | Treatment | iCTC control | [Monolaurin] | iCTC remaining < 10-20 = 0 |
|---|---|---|---|---|
| RP01 | Folfirinox | 550 | 100 uM | 50 |
| | | | 200 uM | 0 |
| | | | 300 uM | 0 |

TABLE 3-continued

Results for Project 1 Study-Pancreatic Cancer Metastatic Pancreatic stage III-IV

| Patient ID | Treatment | iCTC control | [Monolaurin] | iCTC remaining < 10-20 = 0 |
|---|---|---|---|---|
| RP03 | Folfirinox | 23 | 100 uM | 10 |
|  |  |  | 200 uM | 0 |
|  |  |  | 300 uM | 0 |
| RP04 | Folfirinox | 30 | 100 uM | 0 |
|  |  |  | 200 uM | 0 |
|  |  |  | 300 uM | 0 |
| RP10 | Folfirinox | 100 | 100 uM | 10 |
|  |  |  | 200 uM | 0 |
|  |  |  | 300 uM | 0 |
| RP11 | Folfirinox | 40 | 100 uM | 10 |
|  |  |  | 200 uM | 10 |
|  |  |  | 300 uM | 10 |
| RP12 | Folfirinox | 30 | 100 uM | 20 |
|  |  |  | 200 uM | 0 |
|  |  |  | 300 uM | 0 |
| RP'14 | Folfirinox | 40 | 100 uM | 20 |
|  |  |  | 200 uM | 15 |
|  |  |  | 300 uM | 10 |
| RP16 | Folfirinox | 30 | 100 uM | 0 |
|  |  |  | 200 uM | 0 |
|  |  |  | 300 uM | 0 |
| RP17 | Gemzar | 50 | 100 uM | 0 |
|  |  |  | 200 uM | 0 |
|  |  |  | 300 uM | 0 |
| RP18 | Gemzar/Abraxane | 175 | 100 uM | 0 |
|  |  |  | 200 uM | 0 |
|  |  |  | 300 uM | 0 |
| RP22 | Keytruda | 45 | 100 uM | 0 |
|  |  |  | 200 uM | 0 |
|  |  |  | 300 uM | 0 |

2: Monolaurin Anti-iCTC Activity Measured in Prostate Cancer Patient Blood Samples Using the Vitatex Inc. Methods for Single iCTC and Clusters (Project 1 Study-Prostate Cancer)

TABLE 4

Record of Project 1 Study-Prostate Cancer

| Purpose | CTC-Tx ®: iCTC drug response testing ex vivo (CDR) using therapeutic agents. Prepare/store up to 16-mL plasma. |
|---|---|
| Record Equipment | BD caliber 4-channel flow cytometer |
| Data Analysis | FlowJo V10 |
| Document name | Project_1 final report-Prostate cancer |

TABLE 5

Extracted samples for Project 1 Study-Prostate Cancer

| Lab ID | Patient ID | Sample ID | Primary Diagnosis | | | |
|---|---|---|---|---|---|---|
| RP02 | 120390868 | BBW1000-C81203908680 81617NH | Prostate Cancer | 34 | 14 | 4 |
| RP05 | 120814885 | BBW1000-E71208148850 82217NH | Prostate Cancer, | 38 | 18 | 4 |
| RP06 | 120744606 | BBW1000-SC1207446060 90517NH | Prostate Cancer, | 36 | 18 | 4 |
| RP07 | 120371763 | BBW1000-A11203717630 90617NH | Prostate Cancer | 34 | 12 | 4 |
| RP08 | 120749860 | BBW1000-SC1207498600 90717NH | Prostate Cancer | 36 | 16 | 4 |
| RP09 | 120638952 | BBW1000-C81206389520 91117NH | Prostate Cancer, | 33 | 14 | 4 |
| RP13 | 120558197 | BBW1000-A11205581970 92117NH | Prostate Cancer | 36 | 16 | 4 |
|  | 120688935 | BBW1000-A11206889350 92517NH | Prostate Cancer | 36 | 16 | 4 |
| RP19 | 120753971 | BBW1000-C81207539711 00217NH | Prostate Cancer | 36 | 16 | 4 |
| RP20 | 120390868 | BBW1000-C81203908681 00217NH | Prostate Cancer | 34.8 | 12.8 | 4 |

TABLE 6

Mean iCTC count and active treatments of patients studied in Project 1 Study-Prostate Cancer

| Patients | Patient ID | Sample ID | iCTCs (Mean ± SD) (in 1 mL blood) | Active Treatment |
|---|---|---|---|---|
| RP-02 | 120390868 | BBW1000-C8120390868081617NH | 442 ± 31 | Taxotere, Lupron |
| RP-05 | 120814885 | BBW1000-E7120814885082217NH | 21 ± 6 | Zytiga, Lupron |
| RP-06 | 120744606 | BBW1000-SC120744606090517NH | 41 ± 13 |  |
| RP-07 | 120371763 | BBW1000-A1120371763090617NH | 190 ± 1 | Zytiga, Xtandi |
| RP-08 | 120749860 | BBW1000-SC120749860090717NH | 66 ± 5 |  |
| RP-09 | 120638952 | BBW1000-C8120638952091117NH | 232 ± 1 | Xtandi, Lupron, Zytiga |

TABLE 6-continued

Mean iCTC count and active treatments of patients studied in Project 1 Study-Prostate Cancer

| Patients | Patient ID | Sample ID | iCTCs (Mean ± SD) (in 1 mL blood) | Active Treatment |
|---|---|---|---|---|
| RP-13 | 120558197 | BBW1000-A1120558197092117NH | 75 ± 2 | Taxotere, Xofigo, Zytiga |
| RP-15 | 120688935 | BBW1000-A1120688935092517NH | 39 ± 1 | Trelstar, Xtandi |
| RP-19 | 120753971 | BBW1000-C8120753971100217NH | 447 ± 131 | Taxotere |
| RP-20 | 120390868 | BBW1000-C8120390868100217NH | 45 ± 7 | Taxotere, Lupron |

Materials for Project 1 Study-Prostate Cancer
Blood collection tubes: BD Vacutainer® 10 mL sodium heparin tube (BD catalog #367874)).
Vita-Assay™ AN6W plate.
Blood: prostate cancer, up to 40-mL blood was collected from patients and provided by Conversant bio.
Stock Solution and Dilutions
Monolaurin, 4.78 mM with 0.75% PS-80 (Stock Solution C), 13.1 mg monolaurin in 0.25 mL PS-80 and 0.75 mL water and 0.1 mL of this solution was diluted with 0.9 mL of RPMI. Stock solutions were stable for 2 weeks at 4 degrees C. Monolaurin used is an equal mixture of 1-, 2-, and 3-isomers of monolaurin.
Dilution: Monolaurin: Add 209.2 uL, 627.6 uL, and 1.2552 mL of CPI-2400 in 0.75% PS-80 (Stock solution C) and dilute to 10 mL of media to achieve final concentrations of 100 uM, 200 uM, and 300 uM final concentrations of drug cell exposure respectively.

With respect to FIG. 1, a depiction of a generalized experimental scheme for testing efficacy of a composition in accordance with an exemplary embodiment of the present invention against iCTC from the blood of prostate cancer patients is shown. Invasive circulating tumor cells (iCTCs) were obtained from venous blood of the individual with advanced prostate cancer, cultured and exposed to a specific drug or battery of drugs at 1×, 2×, and 3× concentrations in vitro for 3 days. Drug responsiveness was measured by automatic flow cytometry using the reduction of live iCTCs in the treated samples from the number of live iCTCs in the untreated controls. The greater the reduction of iCTCs of a given drug at a given dose indicates greater responsiveness to that dose of the drug. Four AN6W plates were used for each sample. Control and drug at each dose in triplicate were incubated for 72 hours. The iCTCs were measured by flow cytometry and viewed by microscopy as described. The complete culture medium contains 10% fetal bovine serum.

Figure 5:
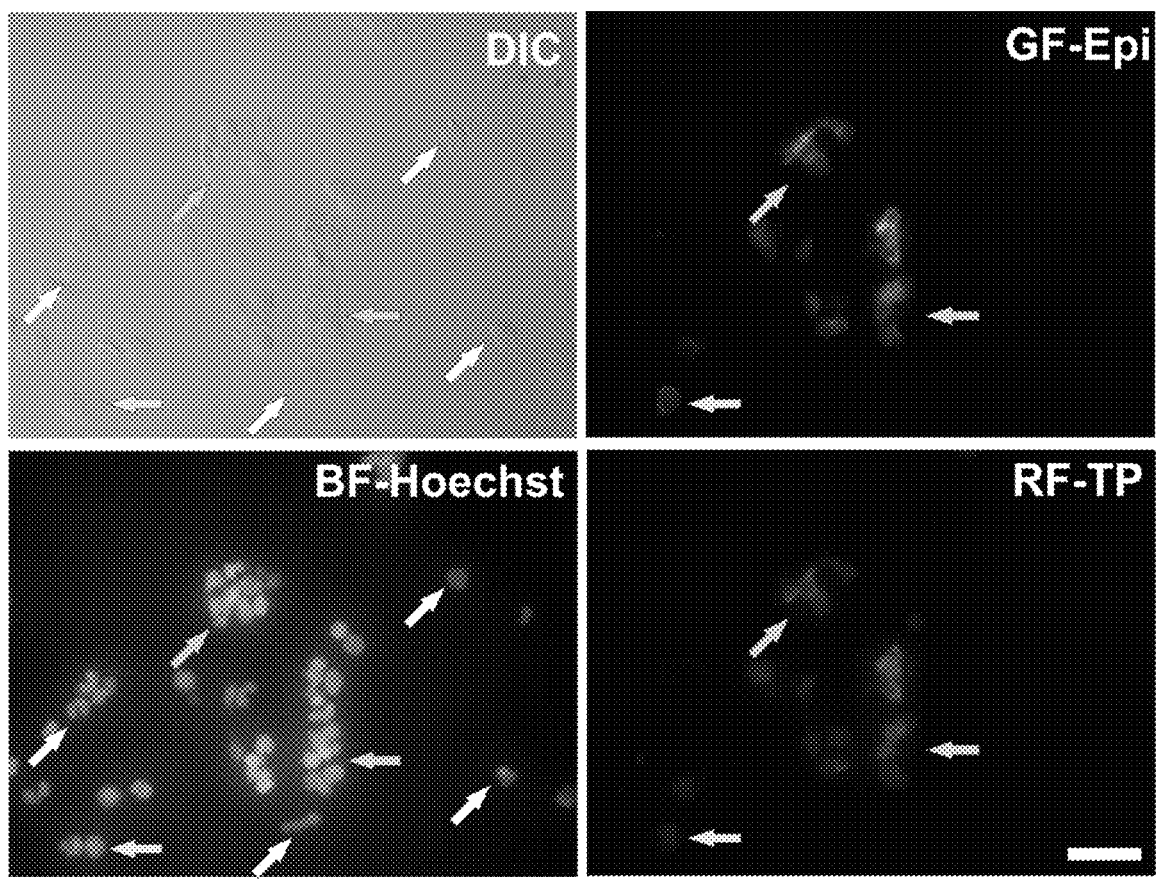
FIG. 5 is a depiction of phenotypic features of solitary and clustered iCTCs cultured for 3 days from a blood sample obtained from a prostate cancer patient with specific markers in four optics of the same field.
Figure 6:
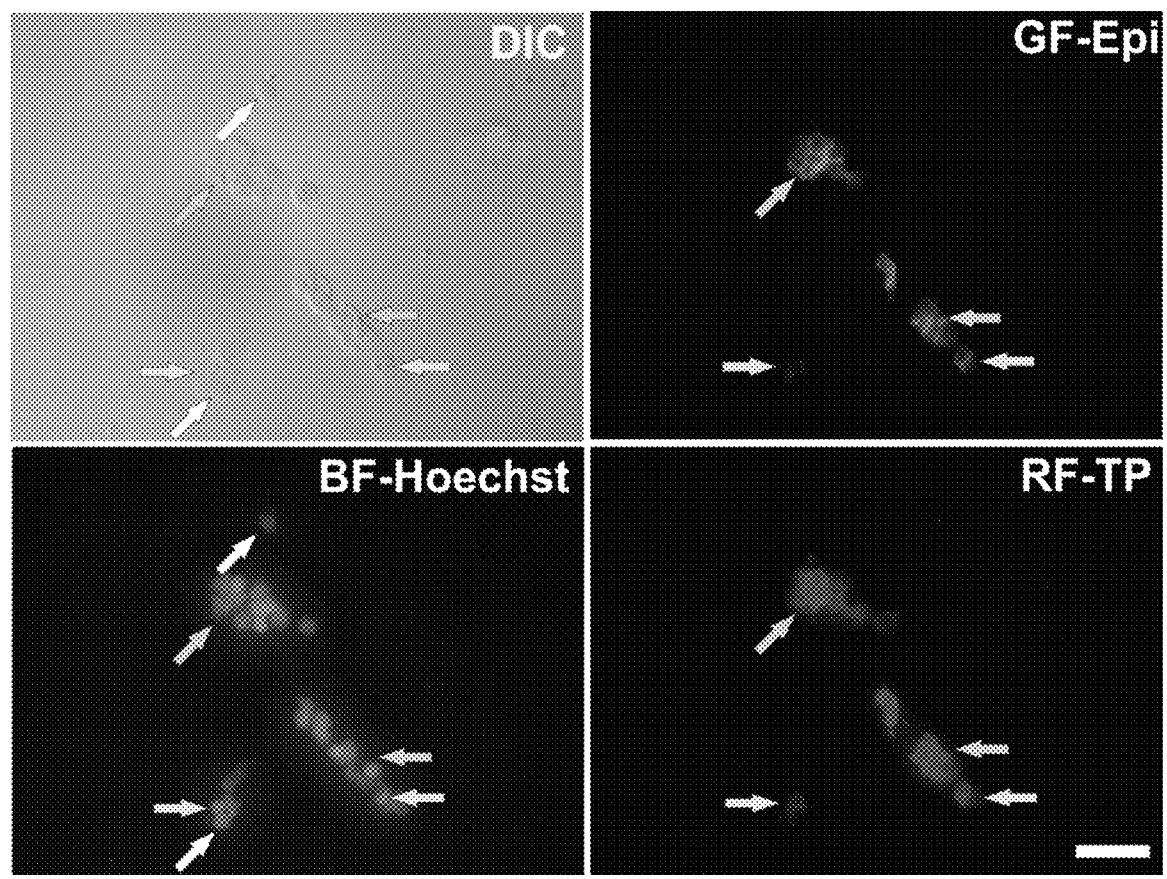
FIG. 6 is a depiction of phenotypic features of solitary and clustered iCTCs cultured for 3 days from an additional prostate cancer patient (i.e., a different patient from that patient described with reference to FIG. 5) with specific markers in four optics of the same field.

The complete experimental procedure for The Project 1 Study-Prostate Cancer followed the same procedure as that used with respect to The Project 1 Study-Pancreatic Cancer. With reference to FIGS. 5 and 6, flow cytometry evaluation: Count tumor cells and immune cells by using a 4-channel (FITC, PE, APC, and 7AAD) flow cytometer. iCTC is defined as: EPI$^+$TP$^+$CD45$^-$7AAD$^+$ FIG. 5 depicts images of solitary and clustered iCTCs with specific markers in a cytospin preparation of the RP-19 sample. Yellow arrows indicate a single iCTC cell recovered by Vita-Assay™ that exhibits its phenotypic features in four optics of the same field. Pink arrows indicated iCTC clusters. A tumor cell was positively stained with green fluorescence-epithelial marker (GF-Epi), blue fluorescence nucleic acid dye (BF-Hoechst) and red fluorescence tumor progenitor (TP) marker (RF-TP). White arrows indicate WBCs that were not stained by Epi and TP tumor markers. Bar=40 μm. Cells from RP-19 were cultured for 3 days before staining.

FIG. 6 depicts images of solitary and clustered iCTCs with specific markers in a cytospin preparation of the RP-20 sample. Yellow arrows indicate a single iCTC cell recovered by Vita-Assay™ that exhibits its phenotypic features in four optics of the same field. Pink arrows indicated iCTC clusters. A tumor cell was positively stained with green fluorescence-epithelial marker (GF-Epi), blue fluorescence nucleic acid dye (BF-Hoechst) and red fluorescence tumor progenitor (TP) marker (RF-TP). White arrows indicate WBCs that were not stained by Epi and TP tumor markers. Bar=40 μm. Cells from RP-20 were cultured for 3 days before staining.

Summary of The Project 1 Study-Prostate Cancer: With reference to Table 7 below, the in vitro iCTC drug response (CDR) assays, designed to assist with the selection of potential low toxicity drugs for the treatment of cancer in individuals based on the response of individual patient-derived iCTCs to specific therapeutic agents in preclinical studies, demonstrated high kill rates of iCTCs from prostate cancer patients using the formulation of monolaurin comprising an equal mixture of 1-, 2-, and 3-isomers of monolaurin.

TABLE 7

Results for The Project 1 Study-Prostate Cancer Metastatic Prostate stage III-IV

| Patient ID | Treatment | iCTC control | [Monolaurin] | iCTC remaining <10-20 = 0 |
|---|---|---|---|---|
| RP02 | Taxotere | 450 | 100 uM | 0 |
|  |  |  | 200 uM | 0 |
|  |  |  | 300 uM | 0 |
| Rp05 | Taxotere | 20 | 100 uM | 15 |
|  |  |  | 200 uM | 0 |
|  |  |  | 300 uM | 0 |
| RP06 | Taxotere | 40 | 100 uM | 10 |
|  |  |  | 200 uM | 0 |
|  |  |  | 300 uM | 0 |
| RP07 | Taxotere | 200 | 100 uM | 0 |
|  |  |  | 200 uM | 0 |
|  |  |  | 300 uM | 0 |
| RP08 | Taxotere | 60 | 100 uM | 0 |
|  |  |  | 200 uM | 0 |
|  |  |  | 300 uM | 0 |

TABLE 7-continued

Results for The Project 1 Study-Prostate Cancer Metastatic Prostate stage III-IV

| Patient ID | Treatment | iCTC control | [Monolaurin] | iCTC remaining <10-20 = 0 |
|---|---|---|---|---|
| RP09 | Taxotere | 225 | 100 uM | 0 |
| | | | 200 uM | 0 |
| | | | 300 uM | 0 |
| RP13 | Taxotere | 75 | 100 uM | 0 |
| | | | 200 uM | 0 |
| | | | 300 uM | 0 |
| RP15 | Taxotere | 50 | 100 uM | 20 |
| | | | 200 uM | 10 |
| | | | 300 uM | 0 |
| RP19 | Taxotere | 425 | 100 uM | 50 |
| | | | 200 uM | 50 |
| | | | 300 uM | 0 |
| RP20 | Taxotere | 50 | 100 uM | 20 |
| | | | 200 uM | 10 |
| | | | 300 uM | 5 |
| RP212 | Taxotere | 55 | 100 uM | 30 |
| | | | 200 uM | 10 |
| | | | 300 uM | 10 |

3. Effects of Novel Composition Combination Monolaurin, Inosine, and β-Glucan on Proliferation and Viability of iCTCs Obtained from Human Cancer Cell Lines HCT-116 (Colon Carcinoma). A549 (Alveolar Lung Adenocarcinoma). HL-60 (Acute Myeloid Leukemia. AML). RS4:11 (B Acute Lymphoblastic Leukemia, B-Cell ALL). U-251 (Astrocytoma). BxPC-3 (Pancreatic Ductal Adenocarcinoma) and PSN-1 (Pancreatic Adenocarcinoma).

Cell Lines:

A number of human tumor cell lines were used in this study: HCT-116 (colon carcinoma), A549 (alveolar lung adenocarcinoma), HL-60 (acute myeloid leukemia, AML), RS4;11 (acute lymphocytic leukemia, ALL), U-251 (glioblastoma), BxPC-3 (pancreatic ductal adenocarcinoma), and PSN-1 (pancreatic adenocarcinoma). All cell lines were sourced from the American Type Culture Collection (ATCC) except U-251 cells, which were obtained from the National Cancer Institute (NCI) and from Molecular Imaging Research (MIR). Cell lines were grown according to supplier recommendations.

Optimizing Density of Cells:

Each cell line (except U-251) was plated at four densities: 10,000, 5,000, 2,500 and 1,250 cells/well in 200 μL of cell-line specific media, in 96-well tissue culture plates (Corning Costar®, Cat. No. 3997) in quadruplicate wells. Because of its rapid growth rate, the U-251 cell line was plated at 1,000, 500, 250, and 125 cells/well. NucLight Rapid Red (Sartorius, Cat. No. 4717) was included in each well at a dilution of 1:1,000 to visualize cell nuclei. After 24 hours in a humidified incubator at 37° C. with 5% CO2 and 95% air, plates were placed in the IncuCyte S3 Live-Cell Imaging microscope and images were acquired at 10× magnification every six hours for a total of 72 hours. Images were then analyzed for % Cell Confluence and Nuclei Count using IncuCyte S3 software algorithms.

The NucLight Rapid Red reagent effectively stained the nuclei of all selected cell lines. Therefore, both data endpoints of "% Cell Confluence" and "Nuclei Count" were used to determine the optimal number of cells/well in each cell line for testing the effects of an exemplary composition.

To optimize experimental conditions, the seeding density that maximized the percentage of log-phase growth over a 72-hour period was determined for each cell line. Data was graphed as a function of time, and an appropriate density was chosen for each tumor cell line that sustained log-phase growth over the largest portion of the 72-hour incubation (see Table 8 for optimum seeding densities selected for each of the cells lines). Six of the seven human tumor cell lines exhibited log-phase growth over the 72-hour incubation period for at least one tested density. Growth of the RS4;11 cell line was minimal; therefore, the highest density (10,000 cells/well) was used for this cell line in the compound treatment experiment. Table 8 summarizes the optimum cell density (cells/well) determined for each cell line.

TABLE 8

Optimum Seeding Density for Selected Tumor Cell Lines

| Human Tumor Cell Line | Tissue of Origin | Density (Cells/Well) |
|---|---|---|
| HCT-116 | colon | 2,500 |
| A549 | lung | 1,250 |
| HL-60 | myeloid | 10,000 |
| RS4; 11 | lymphoid | 10,000 |
| U-251 | brain astrocyte | 1,000 |
| BxPC-3 | pancreatic duct | 2,500 |
| PSN-1 | pancreas | 1,250 |

Composition Preparation:

An exemplary composition was prepared as a mixture of three ingredients in a specific weight ratio: 500 mg monolaurin (glycerol monolaurate), 7.5 mg inosine, and 170 mg beta glucan. All ingredients were sourced as follows: Glycerol Monolaurate (Hangzhou Fuchun Food Additive Co., Ltd. Cat. No. 27215-38-9); Inosine (Sigma-Aldrich, Cat. No. 14125); and Yeast Beta Glucan G70 (Angel Yeast Company, Ltd. Cat. No. 43890-11426).

Prior to treating the cell lines, the composition was prepared by combining 66.7 mg monolaurin, 1 mg inosine, and 23 mg beta glucan in 1.6 mL of 100% DMSO to form a suspension with a final concentration of 150 mM monolaurin. After warming, vortexing, and sonication, the solution remained opaque and appeared to have fatty or soap-like components that settled out of solution. Therefore, the composition suspension was vortexed immediately before adding to cell lines in the compound treatment experiment.

Composition Treatment of Cell Lines:

Cell lines were then treated with a suspension of monolaurin, inosine and beta glucan at 1000:15:340 (w/w/w) in DMSO, at final monolaurin concentrations between 25 and 300 μM. Cell proliferation was measured by visualizing cell nuclei with NucLight Rapid Red and cell viability was determined at a 48-hour endpoint by staining dead cells with Cytotox Green, both using an IncuCyte S3 Live-Cell imaging microscope and accompanying software to acquire and process images every four hours. Proliferation data was normalized to initial cell count at each composition concentration and graphed as a function of time. Viability was represented as % dead cells at 48 hours.

Each cell line was plated at the density specified in Table 8, in 180 μL of media, in 96-well tissue culture plates (Corning Costar®, Cat. #3997) in triplicate wells. NucLight Rapid Red (Sartorius, Cat. No. 4717) was included in each well at a dilution of 1:1,000 to visualize cell nuclei. After a 24 hour incubation in a humidified incubator at 37° C. with 5% CO2 and 95% air, 20 μL of 10× composition diluted in cell-line specific growth media was added to each well in duplicate. The doses of composition tested were equivalent to 25, 50, 100, 150, 200 and 300 μM monolaurin. Vehicle-control (DMSO) duplicate wells were included, and the DMSO concentration was kept constant at 0.1% for all treatments.

After the addition of the composition, plates were immediately placed in the IncuCyte S3 Live-Cell Imaging microscope and set to acquire images at 10× magnification every four hours up to 48 hours after treatment was initiated. Just before the final (48 hour) image scans were to be obtained, a fluorescently labeled toxicity detection reagent, Cytotox Green (Sartorius, Cat. No. 4633, 250 nM), was added to all wells to detect dead cells. Images were analyzed for % Cell Confluence, Nuclei Count, and Dead Cell Count using IncuCyte S3 software algorithms. Data was graphed as a function of time to measure the growth inhibitory effects of the composition on the selected human tumor cell lines.

Though response to the exemplary composition varied amongst the cell lines, treatment with the composition decreased cell proliferation in all seven cell lines based on a decrease in the number of nuclei and/or in cell confluence compared to vehicle control-treated cells. Nuclei counts were normalized to the count at time zero (the time at which the composition was added to cells) and the normalized values were graphed as a function of time. Growth inhibition from the composition was generally dose-dependent, with higher doses resulting in greater inhibition. Images at each concentration of the exemplary composition also show a decrease in both cell nuclei (red color) and cell confluence at higher doses of the composition.

In addition to a decrease in cell proliferation, there was also a dose-dependent increase in tumor cell death after treatment with the exemplary composition as measured by an increase in the number of cells stained green by the cell death detection reagent at higher doses of the composition. A "Percent Dead Cells" value was calculated by dividing the number of dead cells by the total number of cells. FIGS. 7-13 illustrate the effects of the composition on the proliferation and viability of the seven cancer cell lines and include representative images taken at endpoint (48 hours) for each composition concentration.

Figure 7A:
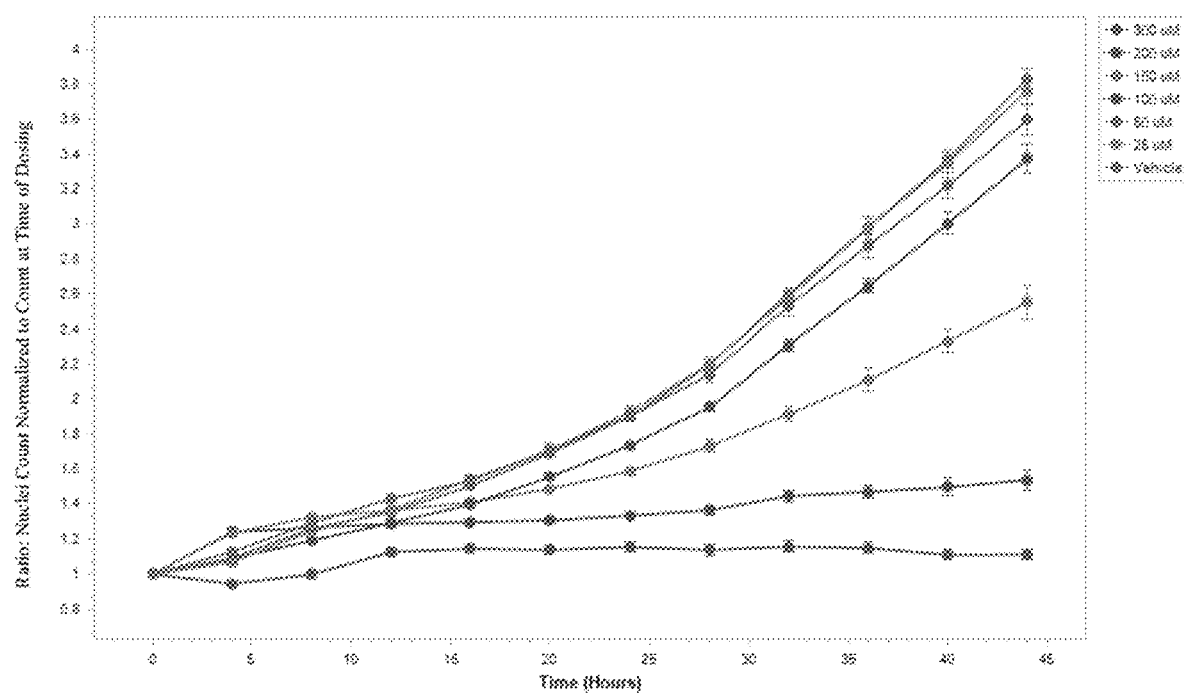
FIG. 7A is a graphical depiction of HCT-116 iCTC cell proliferation and viability over 48 hours under treatment with various concentrations of an exemplary monolaurin, inosine, and beta-glucan composition in accordance with embodiments of the present invention.
Figure 7B:
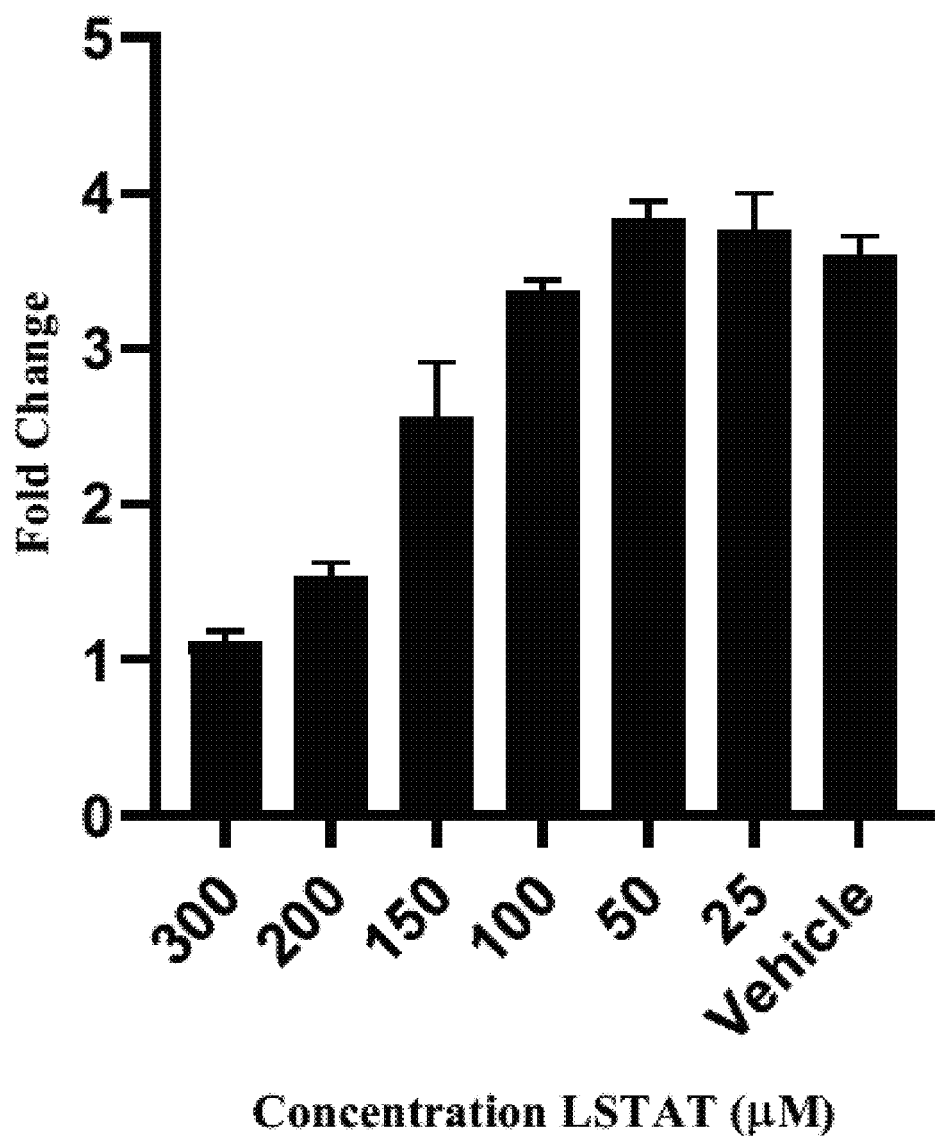
FIG. 7B is a graphical depiction of the normalized cell proliferation of HCT-116 iCTC cells at the 48-hour time point under various concentrations of an exemplary monolaurin, inosine, and beta-glucan composition in accordance with embodiments of the present invention.
Figure 7C:
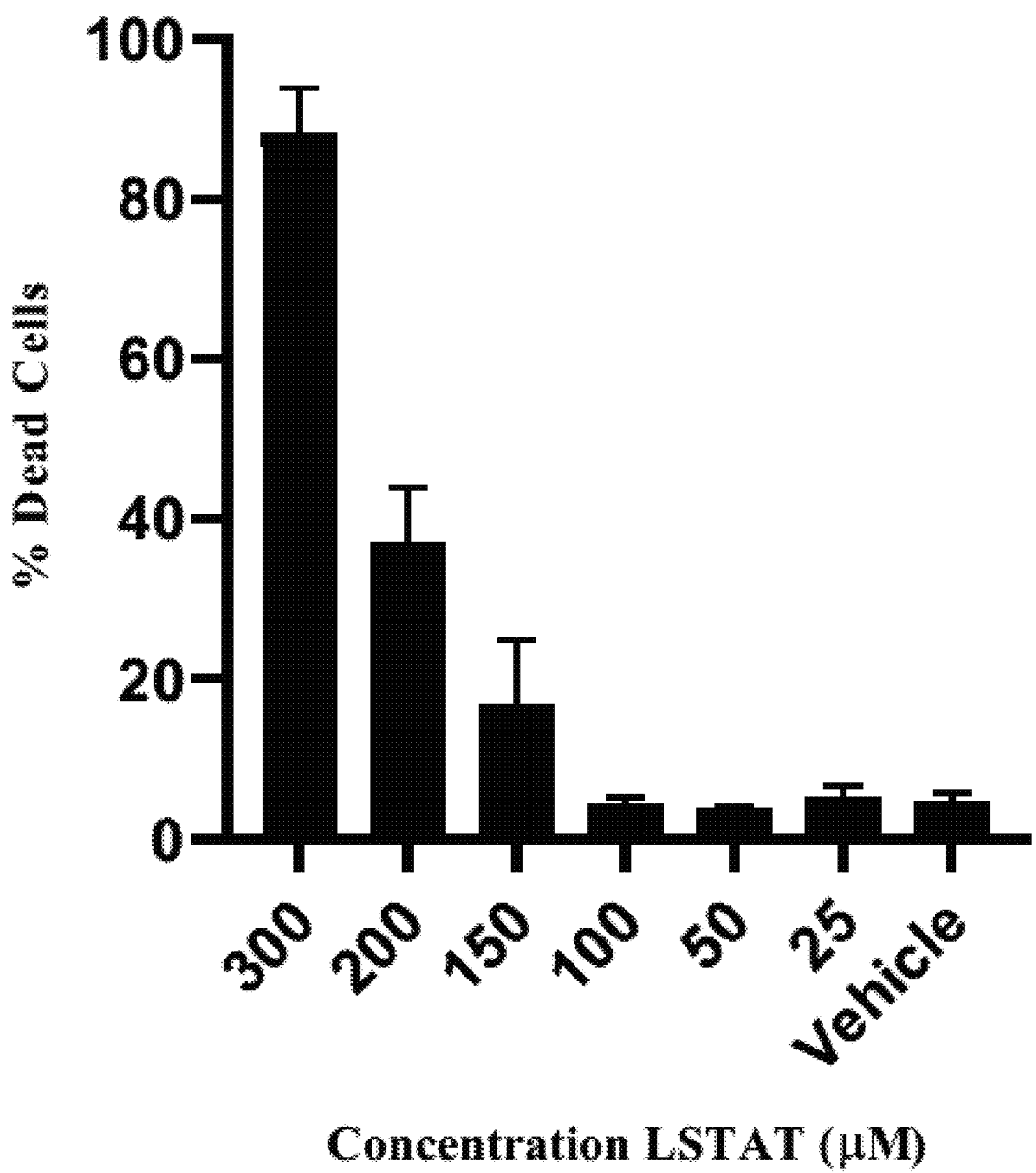
FIG. 7C is a graphical depiction of the cell viability of HCT-116 iCTC cells at the 48-hour time point under various concentrations of an exemplary monolaurin, inosine, and beta-glucan composition in accordance with embodiments of the present invention.

Results:
The effects of the exemplary composition on each cell line are detailed as follows:

HCT-116
HCT-116 human colon carcinoma cells responded to concentrations of the composition between 150 and 300 μM, where the percentage of dead cells at 48 hours ranged from 17±8% to 88±6%, respectively (FIGS. 7A-7C). The inhibition of HCT-116 proliferation and viability by the composition were both dose-dependent (FIGS. 7B and 7C), and the composition's effects on HCT-116 were observed between 16 and 20 hours after treatment was initiated (FIG. 7A).

Figure 8A:
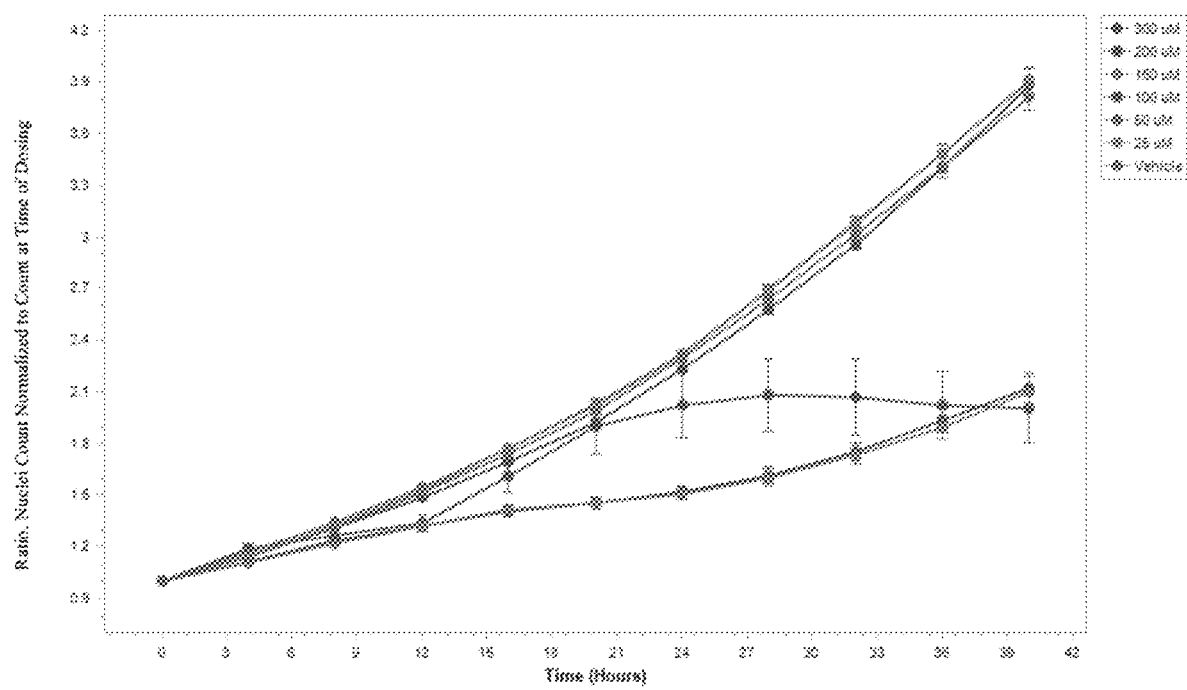
FIG. 8A is a graphical depiction of A549 iCTC cell proliferation and viability over 48 hours under treatment with various concentrations of an exemplary monolaurin, inosine, and beta-glucan composition in accordance with embodiments of the present invention.
Figure 8B:
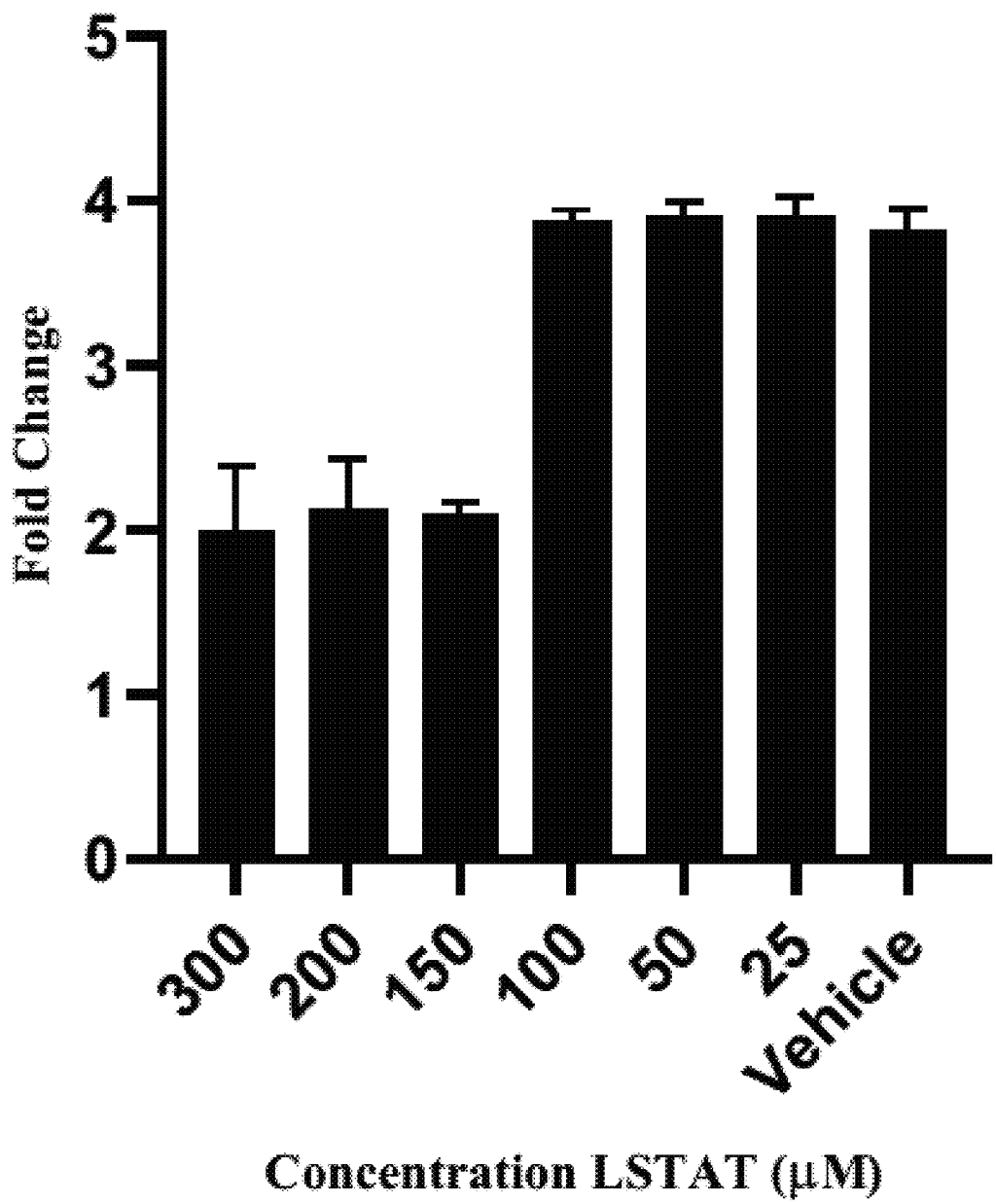
FIG. 8B is a graphical depiction of the normalized cell proliferation of A549 iCTC cells at the 48-hour time point under various concentrations of an exemplary monolaurin, inosine, and beta-glucan composition in accordance with embodiments of the present invention.
Figure 8C:
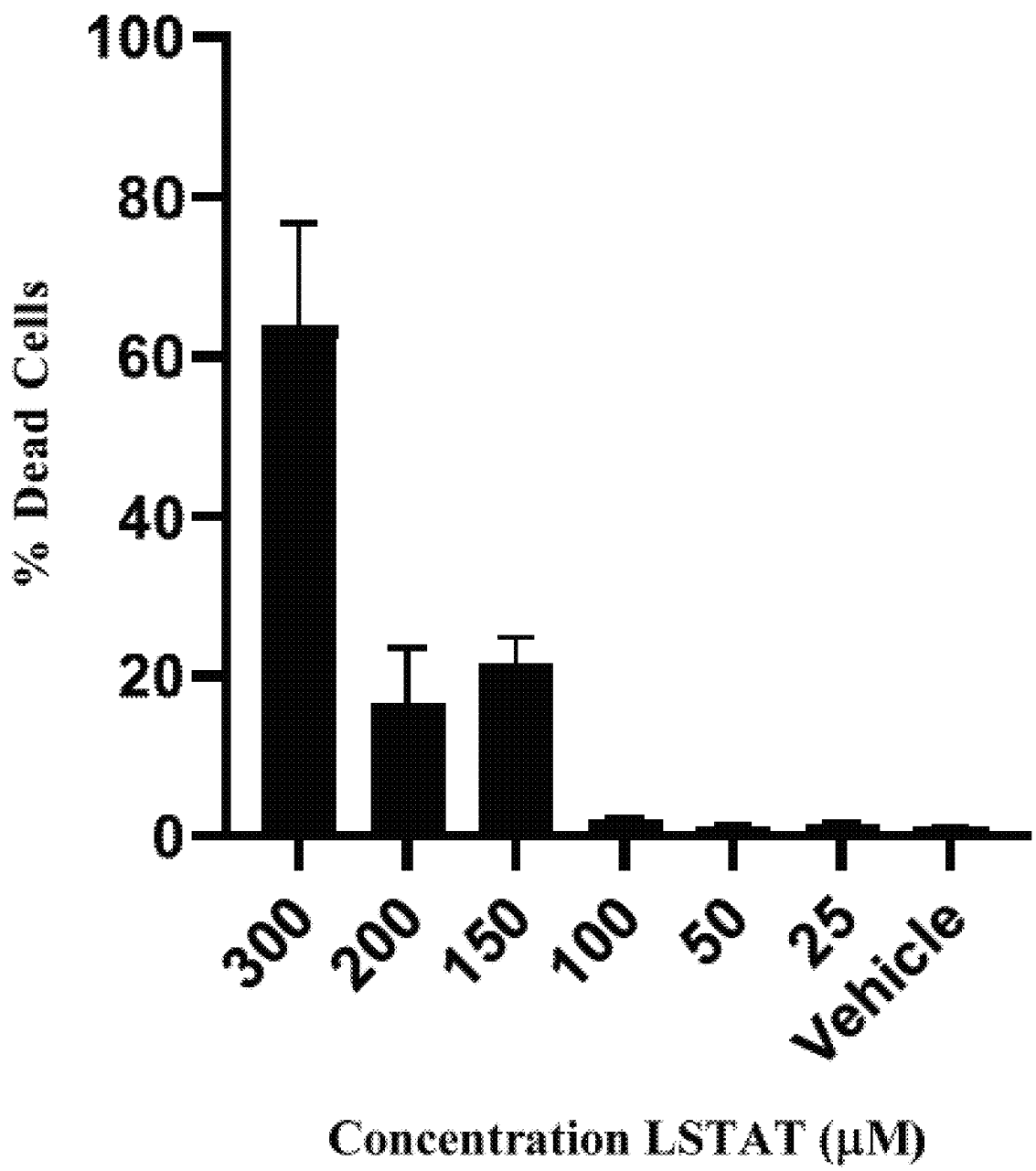
FIG. 8C is a graphical depiction of the cell viability of A549 iCTC cells at the 48-hour time point under various concentrations of an exemplary monolaurin, inosine, and beta-glucan composition in accordance with embodiments of the present invention.

A549
A549 human lung adenocarcinoma cells responded to concentrations of the composition inhibition at concentrations between 150 and 300 μM, where the percentage of dead cells ranged from 21±3% to 64±13%, respectively (FIG. 8A-8C), a relatively mild response compared to the other cell lines. Notably, A549 proliferation (growth) was unaffected at composition concentrations up to 100 μM but inhibited at 150 μM composition and above. Inhibition of A549 proliferation and viability by the composition were observed at 12 hours after treatment was initiated (FIG. 8A).

Figure 9A:
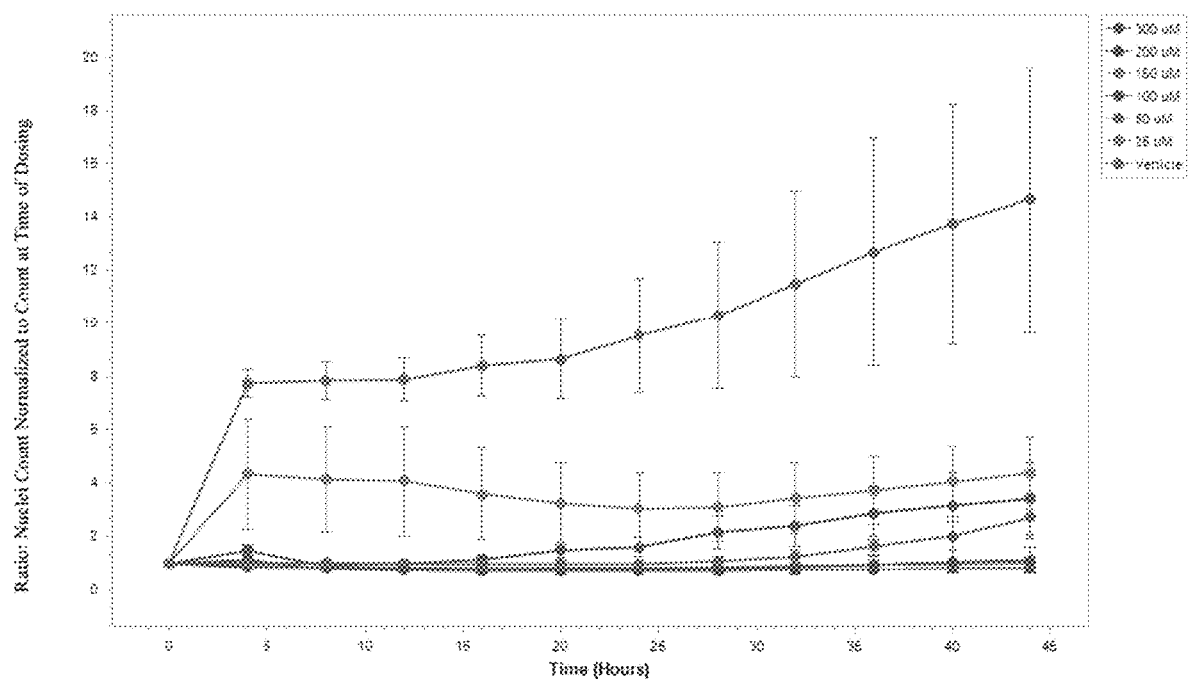
FIG. 9A is a graphical depiction of HL-60 iCTC cell proliferation and viability over 48 hours under treatment with various concentrations of an exemplary monolaurin, inosine, and beta-glucan composition in accordance with embodiments of the present invention.
Figure 9B:
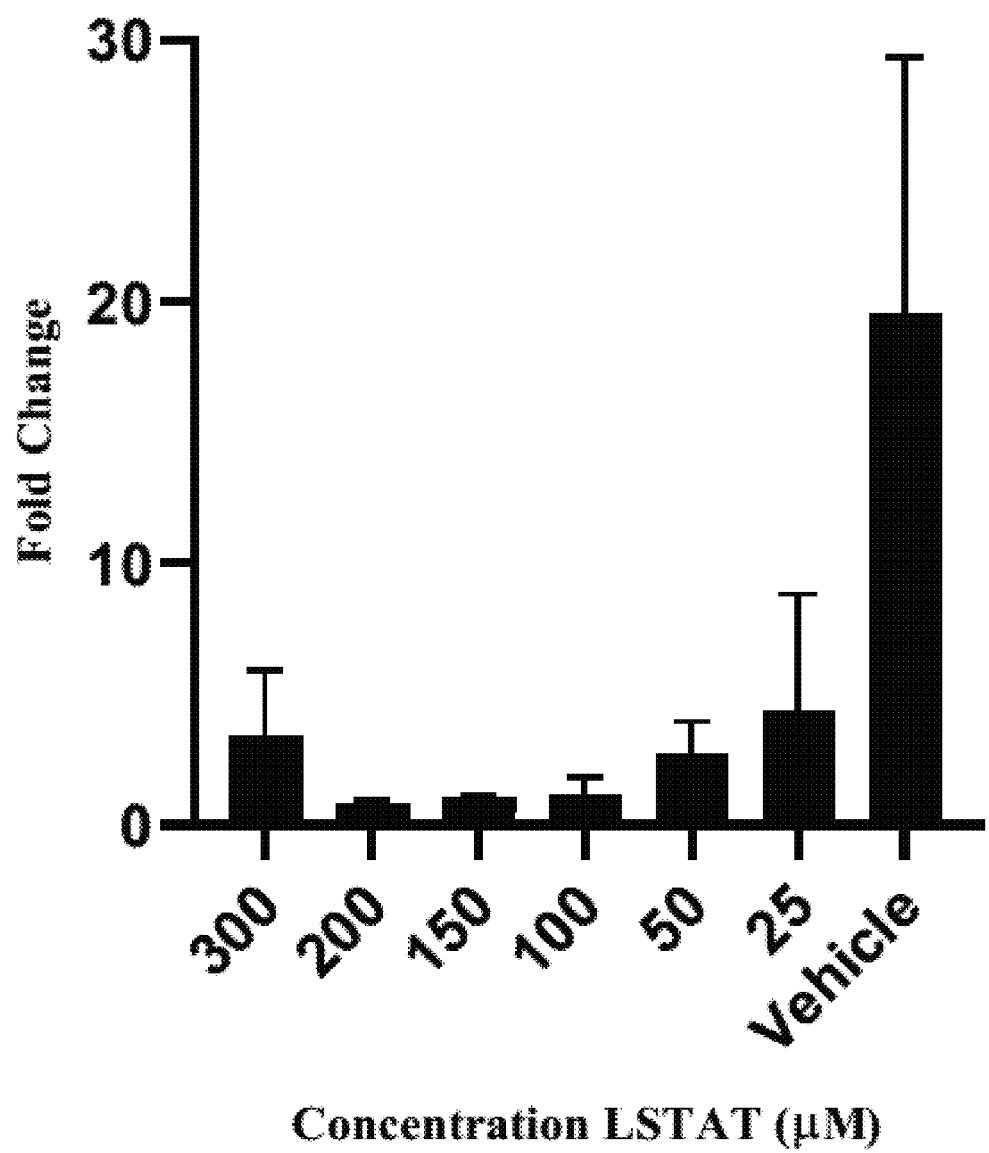
FIG. 9B is a graphical depiction of the normalized cell proliferation of HL-60 iCTC cells at the 48-hour time point under various concentrations of an exemplary monolaurin, inosine, and beta-glucan composition in accordance with embodiments of the present invention.
Figure 9C:
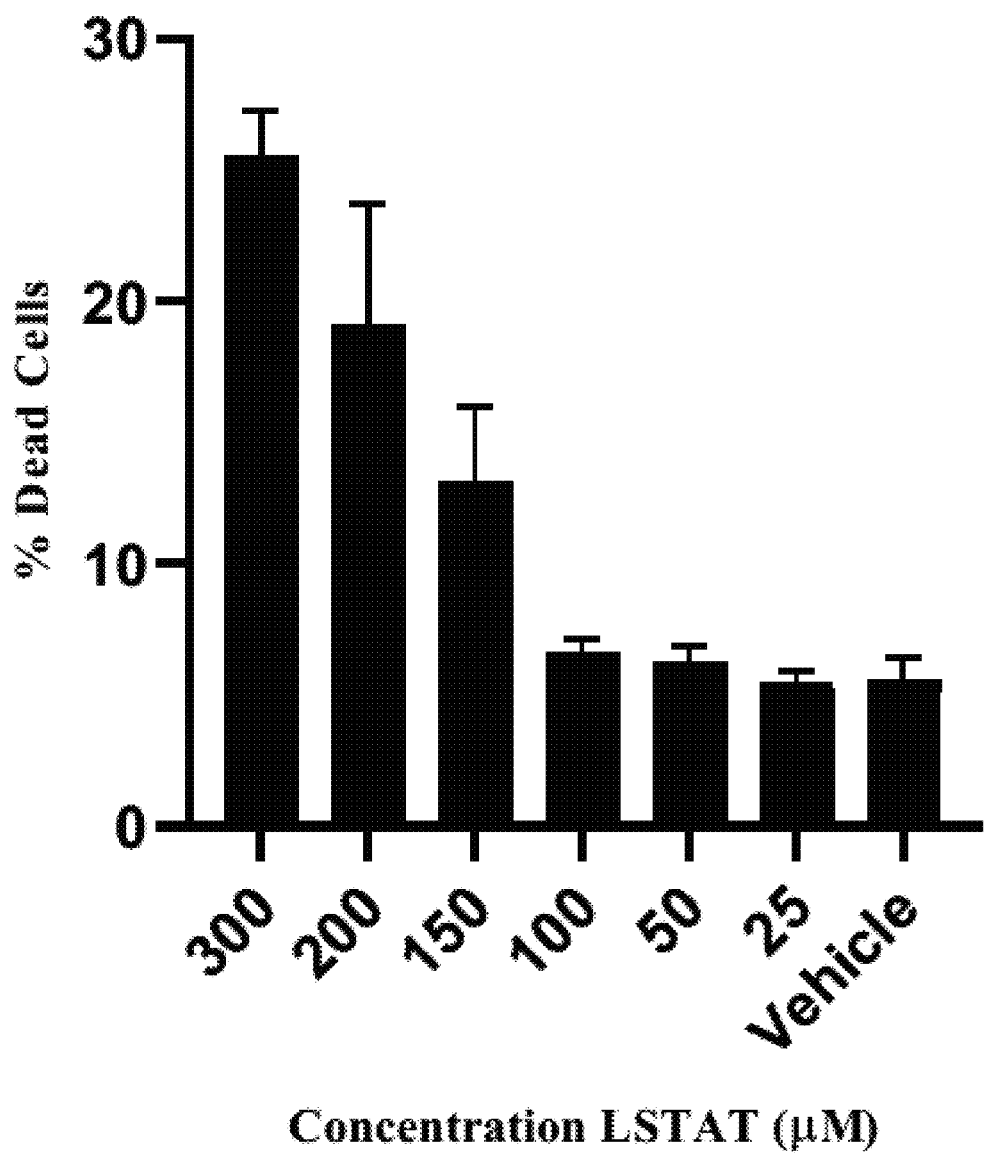
FIG. 9C is a graphical depiction of the cell viability of HL-60 iCTC cells at the 48-hour time point under various concentrations of an exemplary monolaurin, inosine, and beta-glucan composition in accordance with embodiments of the present invention.

HL-60
Control HL-60 human acute myeloid leukemia cells demonstrated biphasic proliferation, with an initial (linear) rapid phase during the first four hours (achieving an 8-fold increase in cell number) and a more gradual (somewhat logarithmic) phase up to 48 hours (ultimately achieving a 20-fold increase in cell number) (FIG. 9A). Also of note, while 90-95% of cultured HL-60 cells display more immature promyelocytic morphology, the remaining cells resemble more mature myeloid cells; the ratio of mature to immature cells and the identity of the mature myeloid cells (granulocyte-like v. monocyte/macrophage-like) can be manipulated by changing cell culture conditions (12). It was found that even at the lowest concentration of the exemplary composition (25 μM), inhibition of HL-60 growth was observed within the first four hours (FIG. 9A). The highest concentration of the exemplary composition appeared to have less impact on cell proliferation than expected (FIGS. 9A-9C). Composition-induced cell death was observed starting at concentrations of 100-150 μM and up, but only achieved a maximum of 26±2% at 300 μM composition.

Figure 10A:
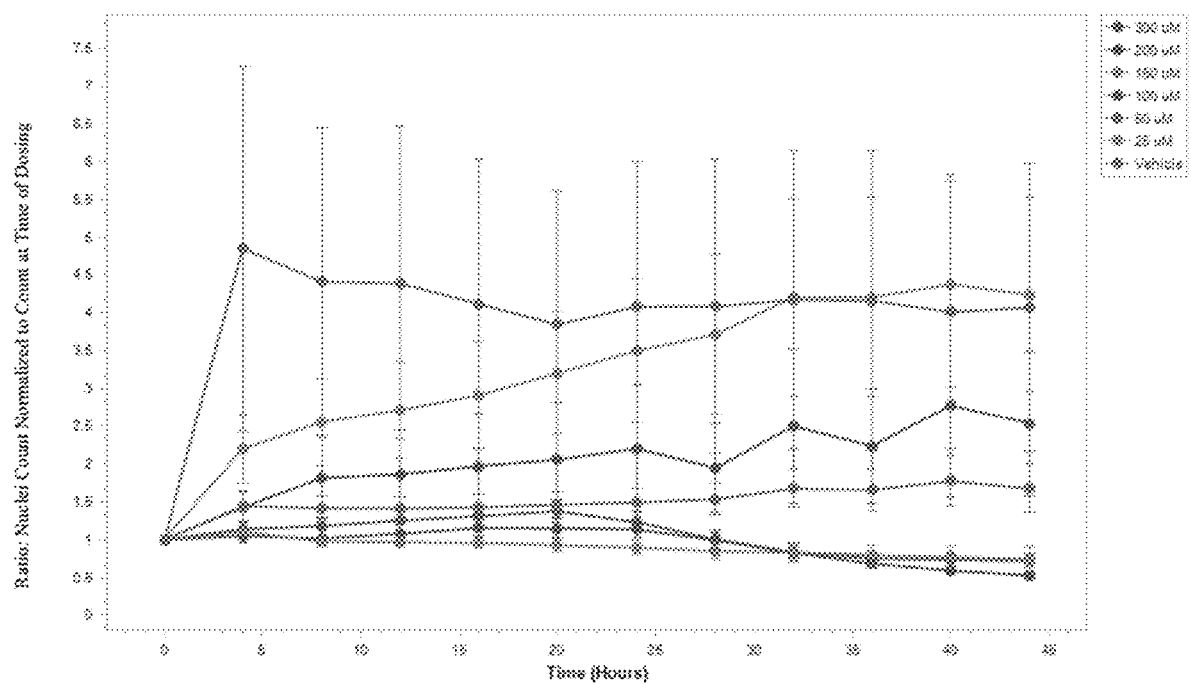
FIG. 10A is a graphical depiction of RS4;11 iCTC cell proliferation and viability over 48 hours under treatment with various concentrations of an exemplary monolaurin, inosine, and beta-glucan composition in accordance with embodiments of the present invention.
Figure 10B:
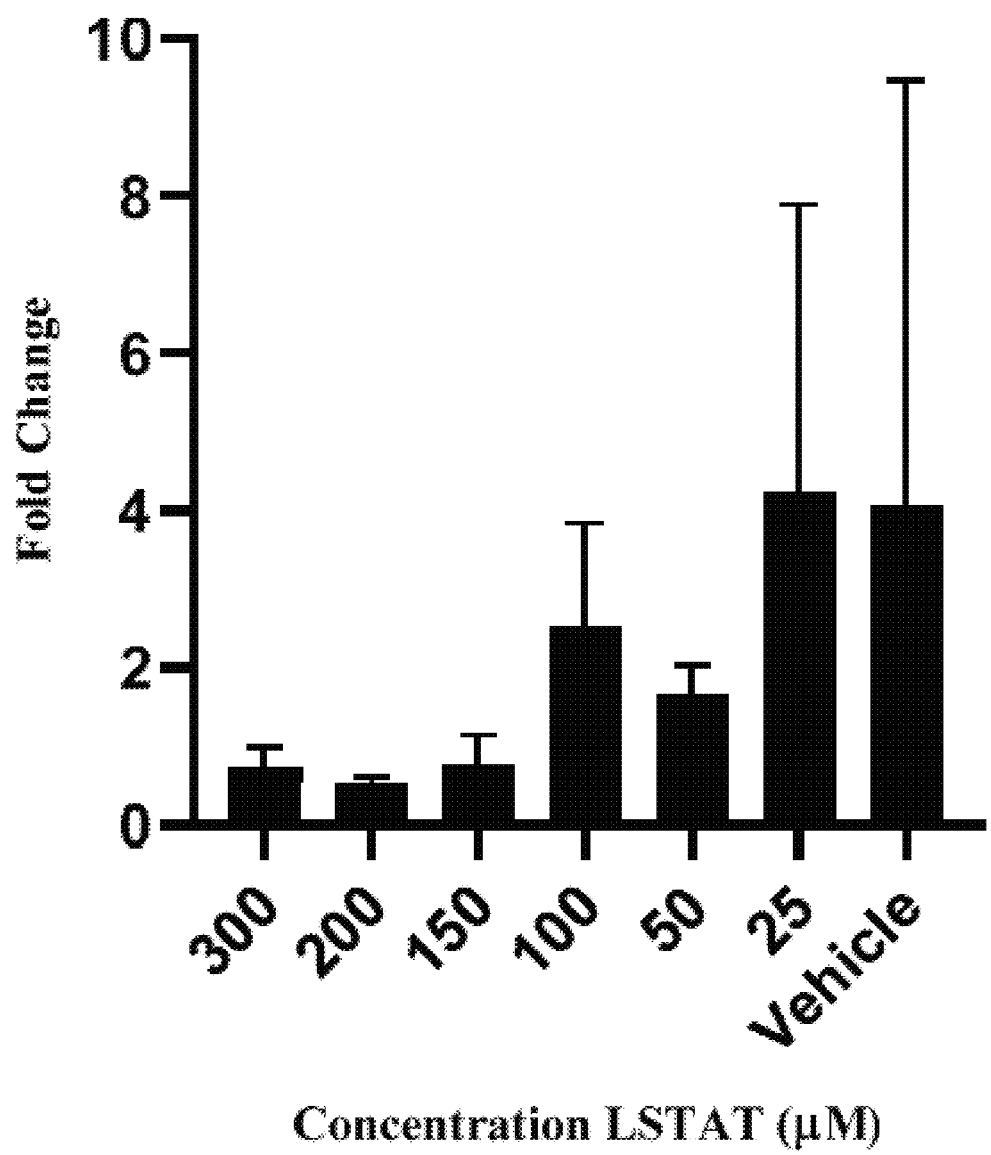
FIG. 10B is a graphical depiction of the normalized cell proliferation of RS4;11 iCTC cells at the 48-hour time point under various concentrations of an exemplary monolaurin, inosine, and beta-glucan composition in accordance with embodiments of the present invention.
Figure 10C:
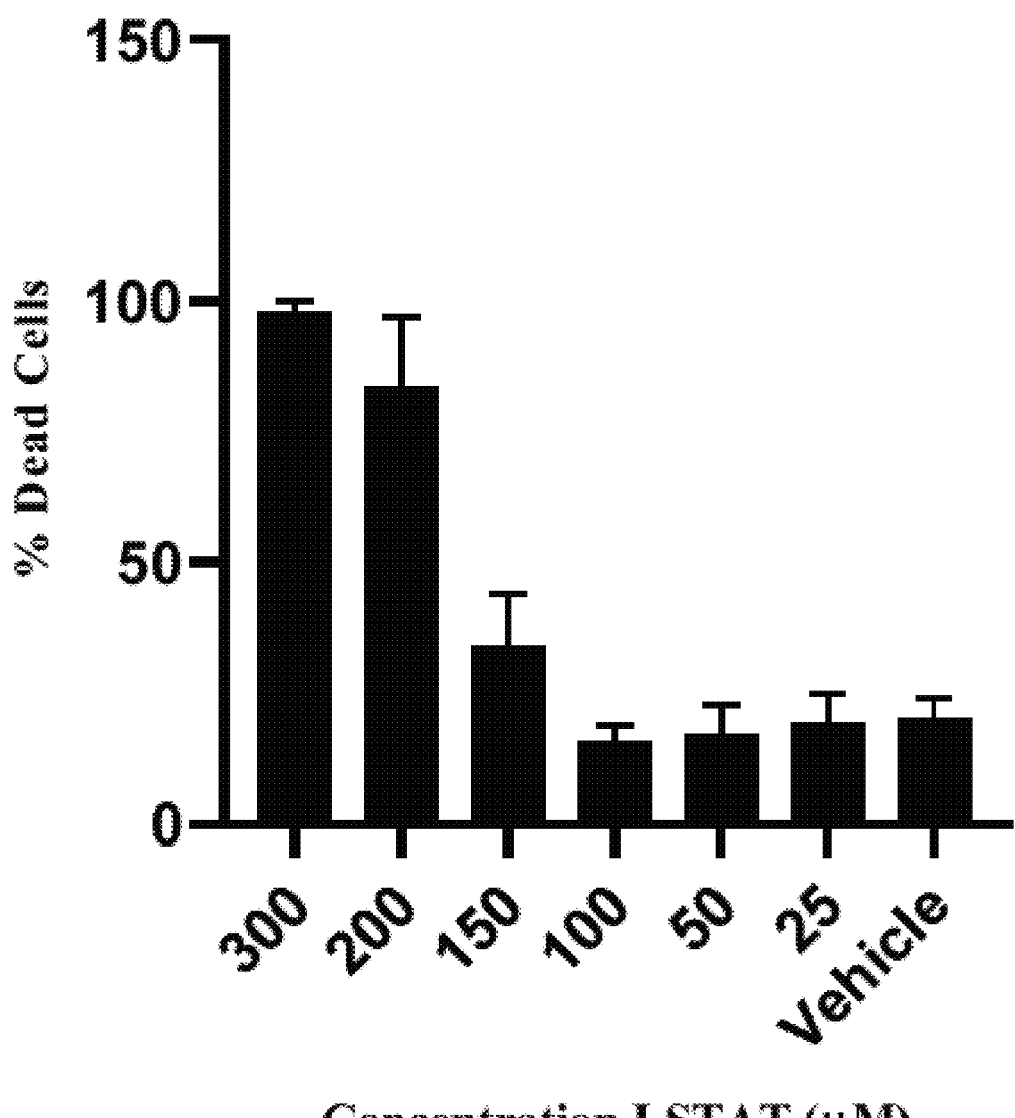
FIG. 10C is a graphical depiction of the cell viability of RS4;11 iCTC cells at the 48-hour time point under various concentrations of an exemplary monolaurin, inosine, and beta-glucan composition in accordance with embodiments of the present invention.

RS4;11
As with HL-60 cells, control RS4;11 human B cell acute lymphoblastic leukemia cells demonstrated biphasic proliferation, although the four hour rapid phase was followed by no apparent growth (FIG. 10A). Also like HL-60 cells, there was a high degree of variability between samples; the standard deviation in live cell counts of the vehicle control fluctuated 132% of the actual value at 48 hours, and among treatment groups standard deviations ranged from 15% (200 μM composition) to 86% (25 μM composition) of the 48-hour live cell values (FIGS. 10A-10C).

Figure 11A:
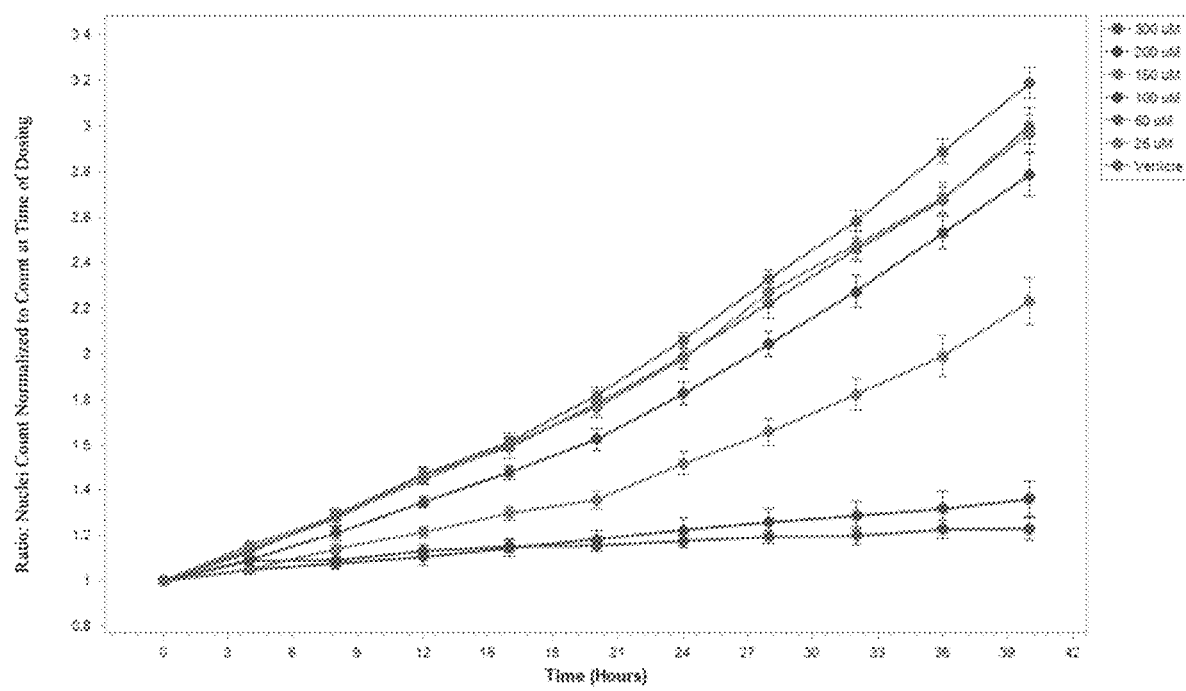
FIG. 11A is a graphical depiction of U-251 iCTC cell proliferation and viability over 48 hours under treatment with various concentrations of an exemplary monolaurin, inosine, and beta-glucan composition in accordance with embodiments of the present invention.
Figure 11B:
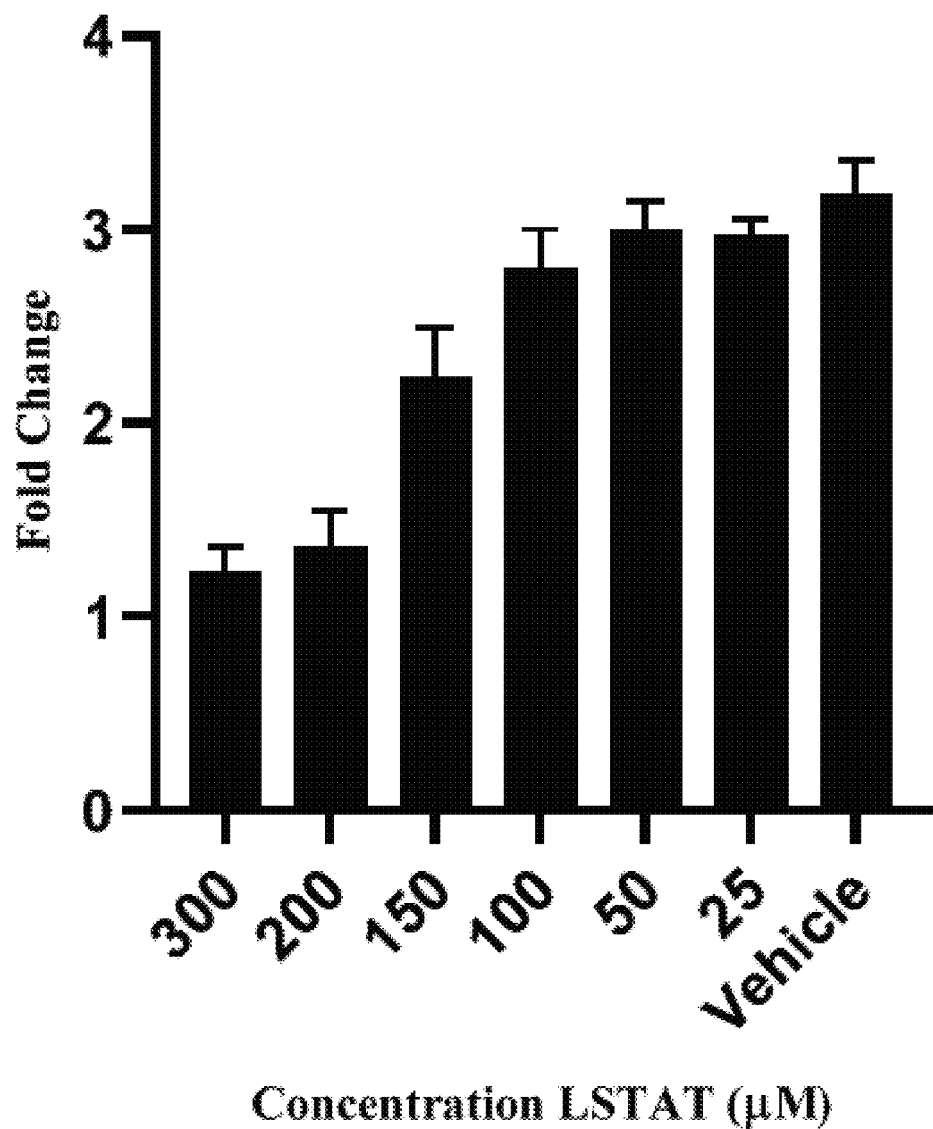
FIG. 11B is a graphical depiction of the normalized cell proliferation of U-251 iCTC cells at the 48-hour time point under various concentrations of an exemplary monolaurin, inosine, and beta-glucan composition in accordance with embodiments of the present invention.
Figure 11C:
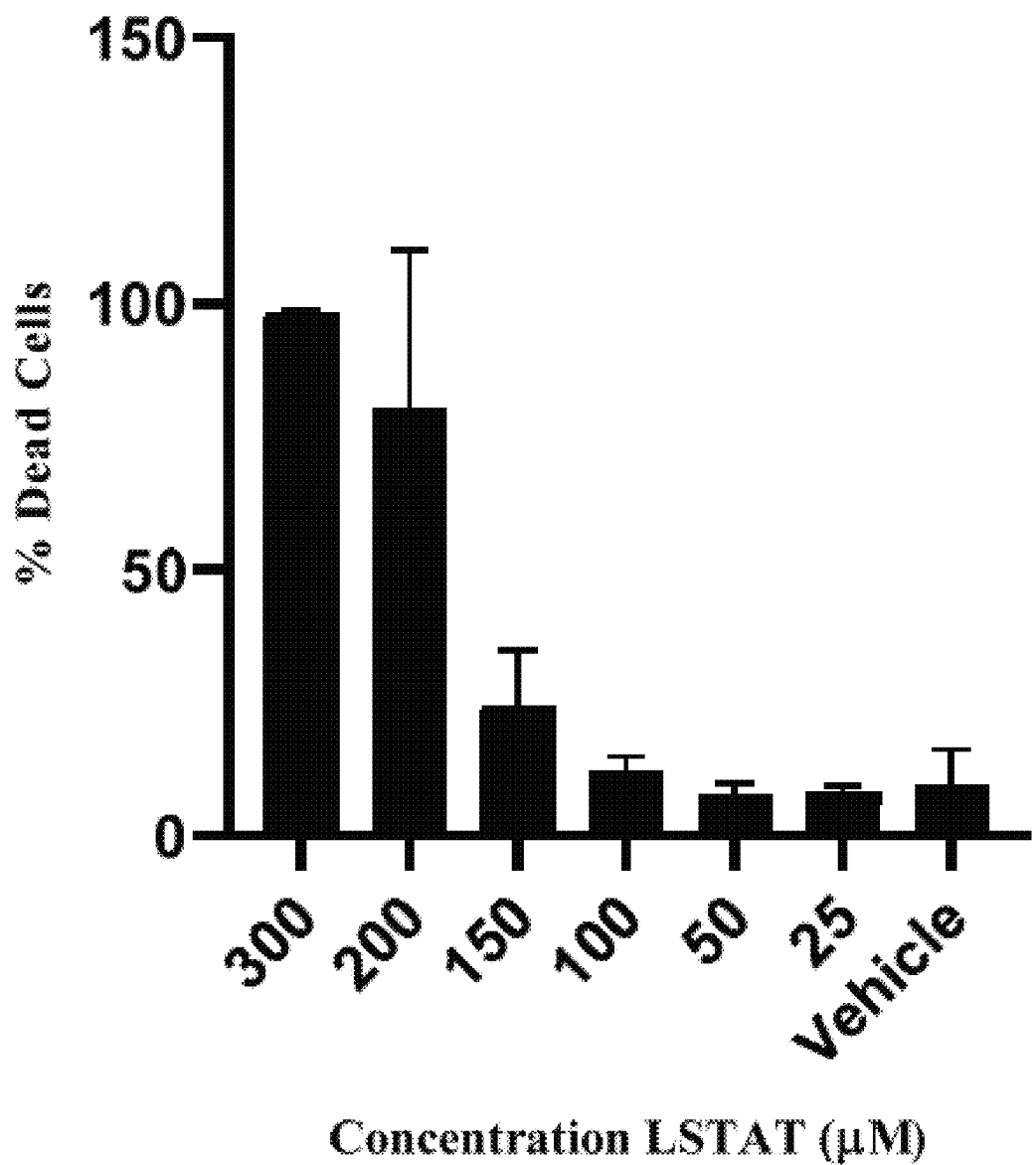
FIG. 11C is a graphical depiction of the cell viability of U-251 iCTC cells at the 48-hour time point under various concentrations of an exemplary monolaurin, inosine, and beta-glucan composition in accordance with embodiments of the present invention.

U-251
U-251 human glioblastoma cells responded to concentrations of the exemplary composition between 100 and 300 μM, where the percentage of dead cells at 48 hours ranged from 12±3% to 98±1%, respectively (FIGS. 11A-11C). Inhibition of U-251 proliferation and viability by the composition were both dose-dependent (FIGS. 11B and 11C), and the effects of the composition on U-251 proliferation were observed at 8 hours after treatment was initiated (FIG. 11A).

Figure 12A:
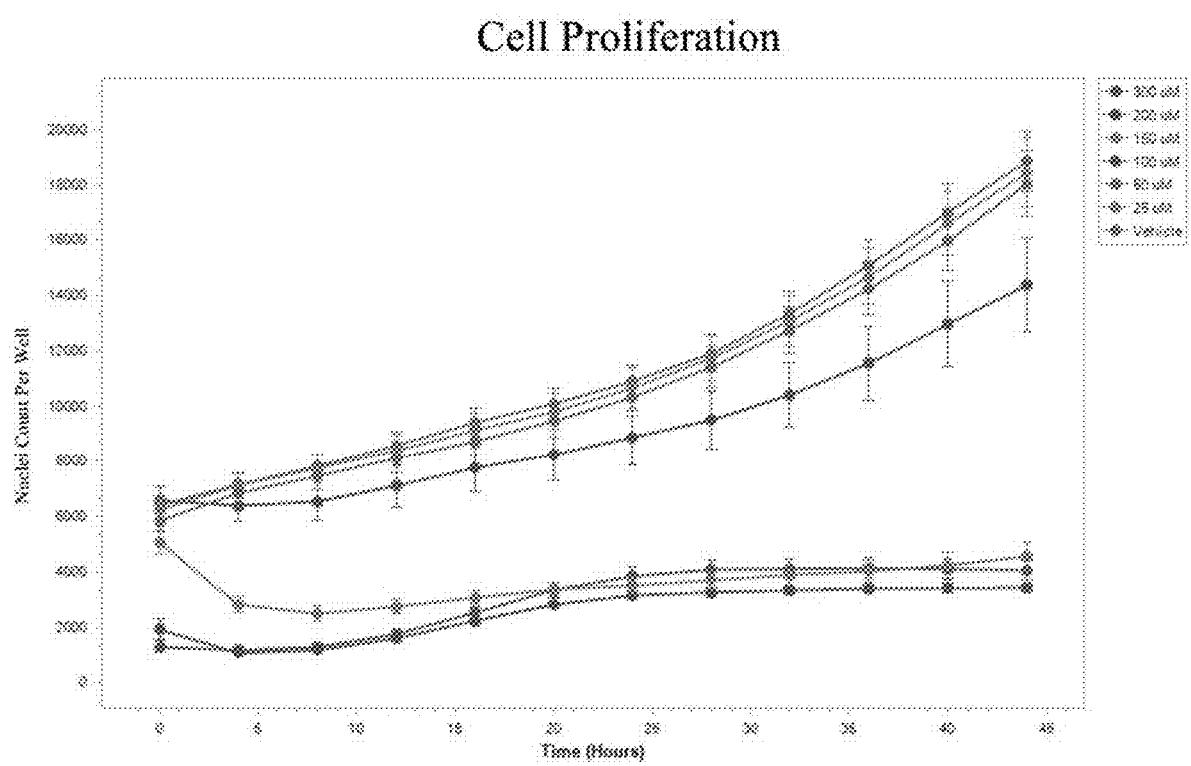
FIG. 12A is a graphical depiction of BxPC-3 iCTC cell proliferation and viability over 48 hours under treatment with various concentrations of an exemplary monolaurin, inosine, and beta-glucan composition in accordance with embodiments of the present invention.
Figure 12B:
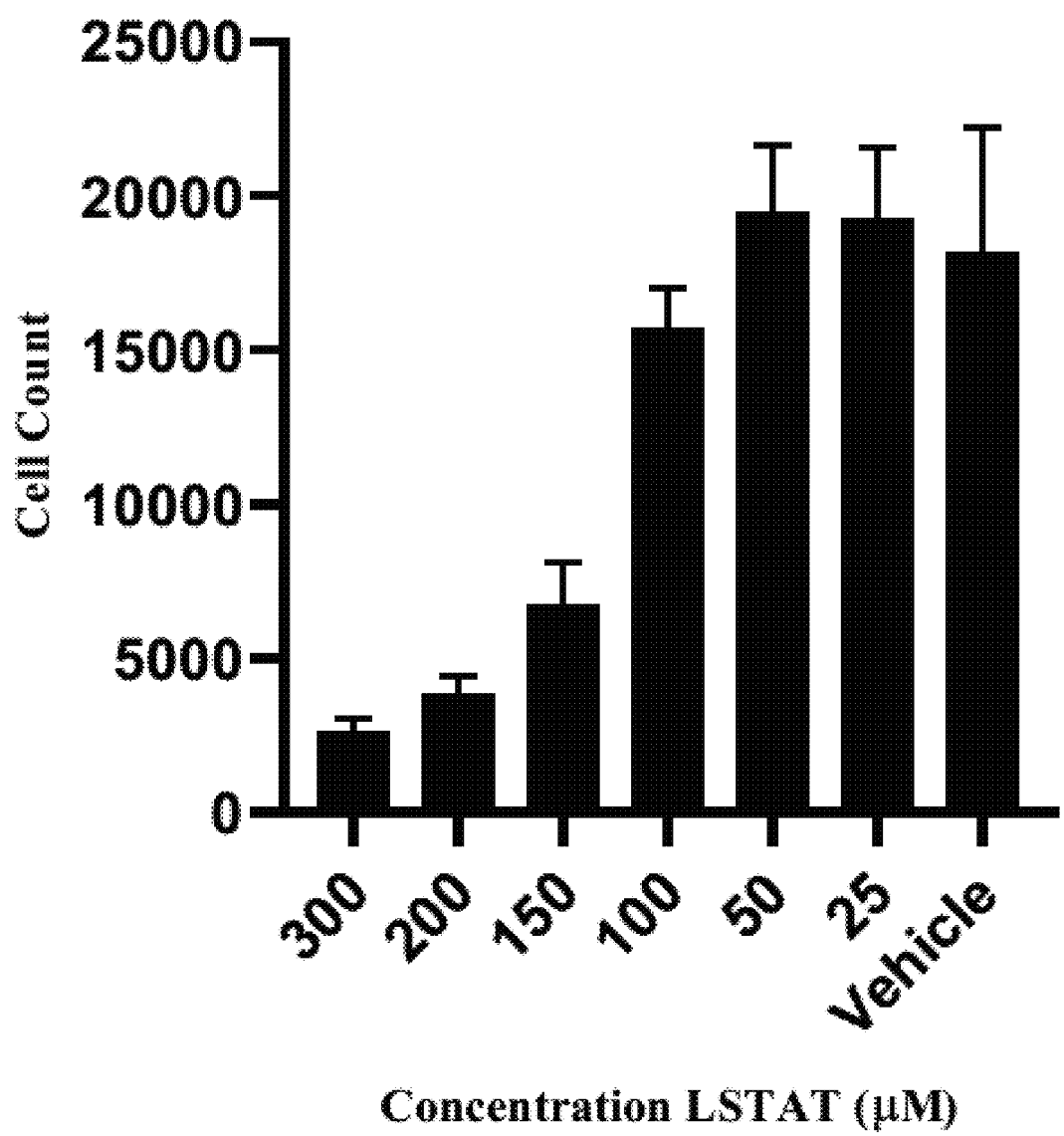
FIG. 12B is a graphical depiction of the normalized cell proliferation of BxPC-3 iCTC cells at the 48-hour time point under various concentrations of an exemplary monolaurin, inosine, and beta-glucan composition in accordance with embodiments of the present invention.
Figure 12C:
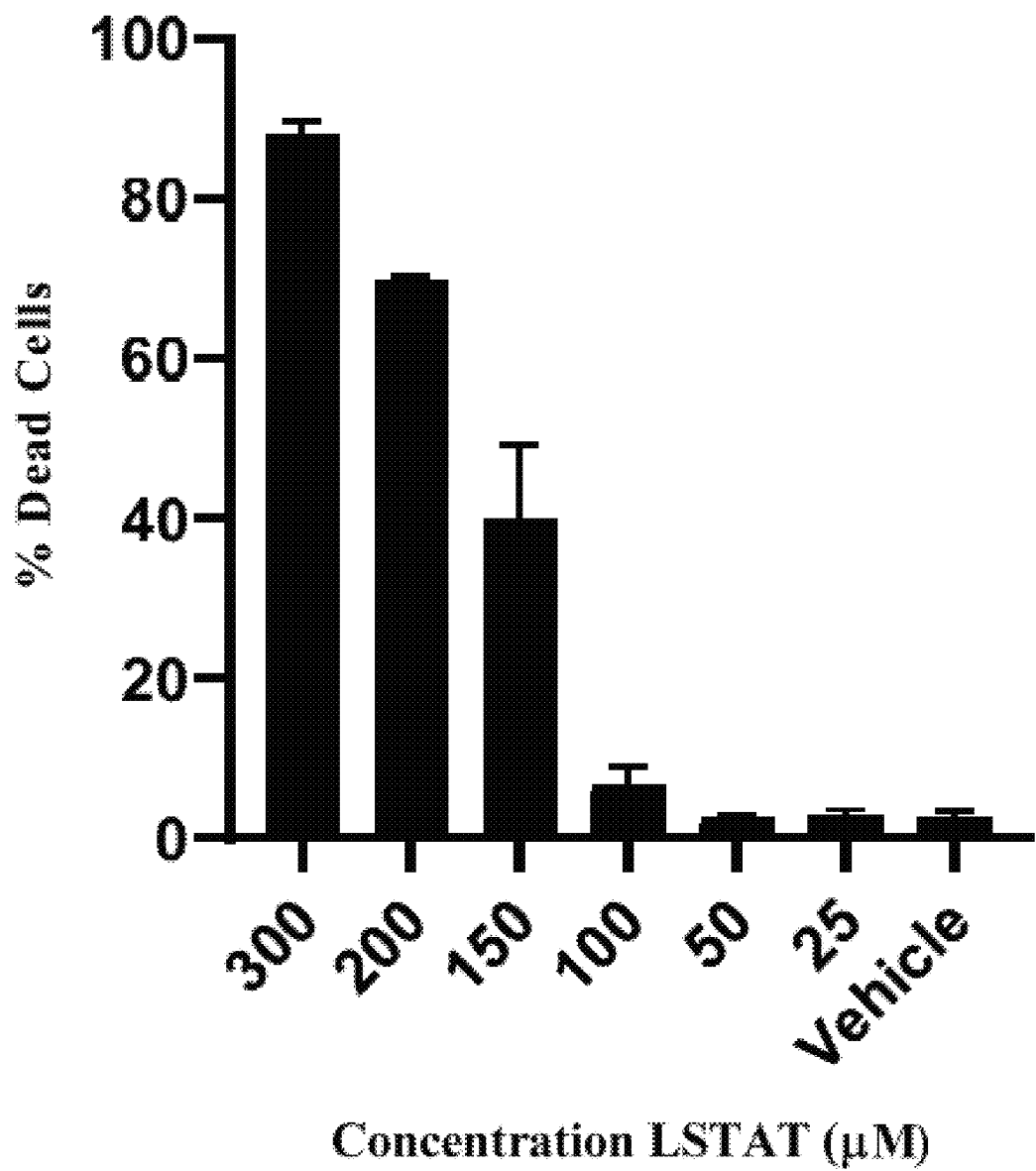
FIG. 12C is a graphical depiction of the cell viability of BxPC-3 iCTC cells at the 48-hour time point under various concentrations of an exemplary monolaurin, inosine, and beta-glucan composition in accordance with embodiments of the present invention.

BxPC-3
BxPC-3 human pancreatic ductal adenocarcinoma responded to concentrations of the composition between 100 and 300 μM in a dose-dependent manner (FIGS. 12A-12C), and the percentage of dead cells on Day 48 ranged from 7±2% to 88±2%, respectively. Throughout the 48-hour time course, the pattern of BxPC-3 proliferation varied among the study groups receiving the higher concentrations (≥100 μM) of the composition, and cell numbers were reduced below initial values at both 4- and 8-hour time points (FIG. 12A).

Figure 13A:
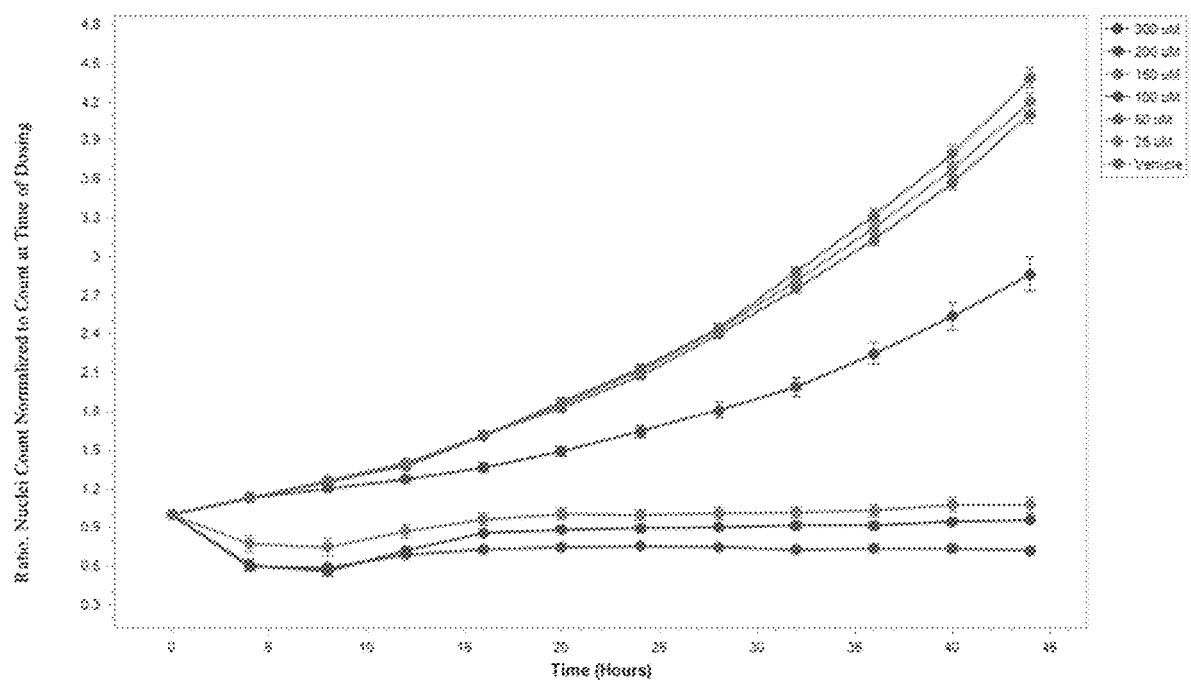
FIG. 13A is a graphical depiction of PSN-1 iCTC cell proliferation and viability over 48 hours under treatment with various concentrations of an exemplary monolaurin, inosine, and beta-glucan composition in accordance with embodiments of the present invention.
Figure 13B:
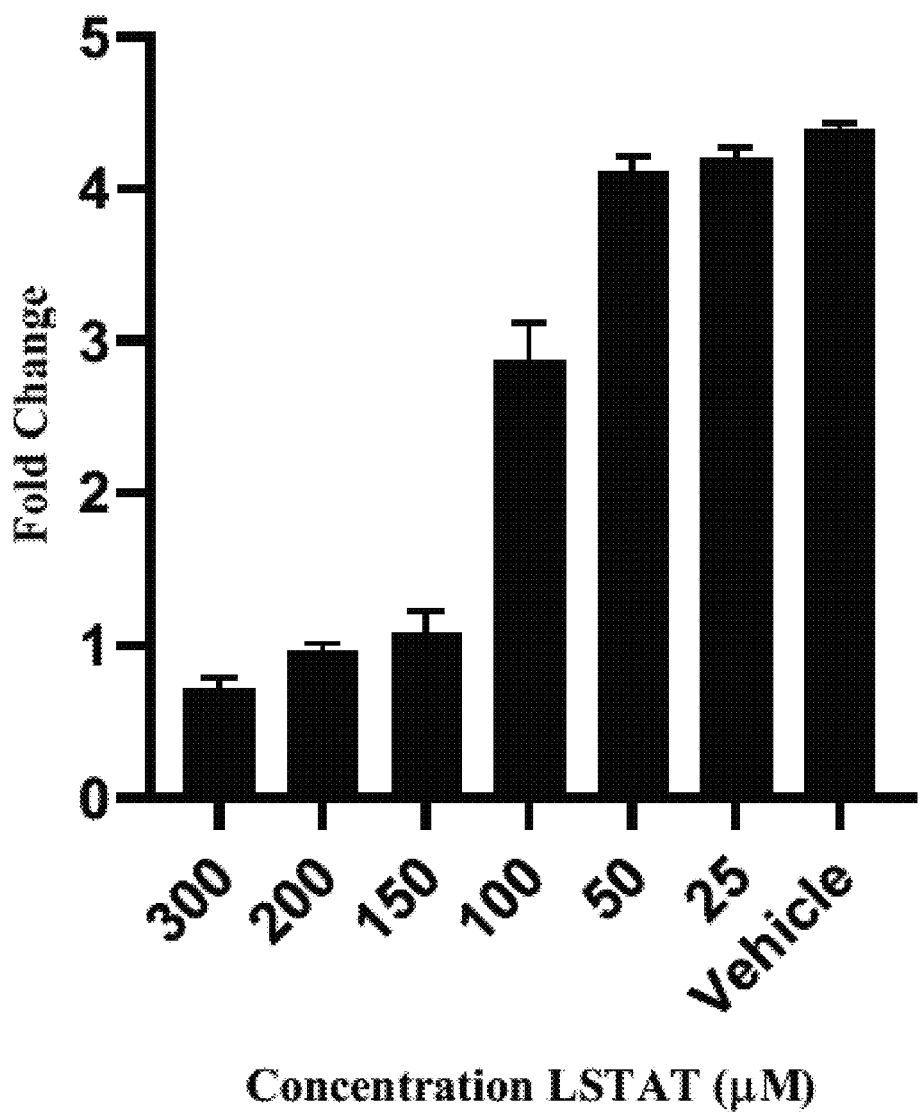
FIG. 13B is a graphical depiction of the normalized cell proliferation of PSN-1 iCTC cells at the 48-hour time point under various concentrations of an exemplary monolaurin, inosine, and beta-glucan composition in accordance with embodiments of the present invention.
Figure 13C:
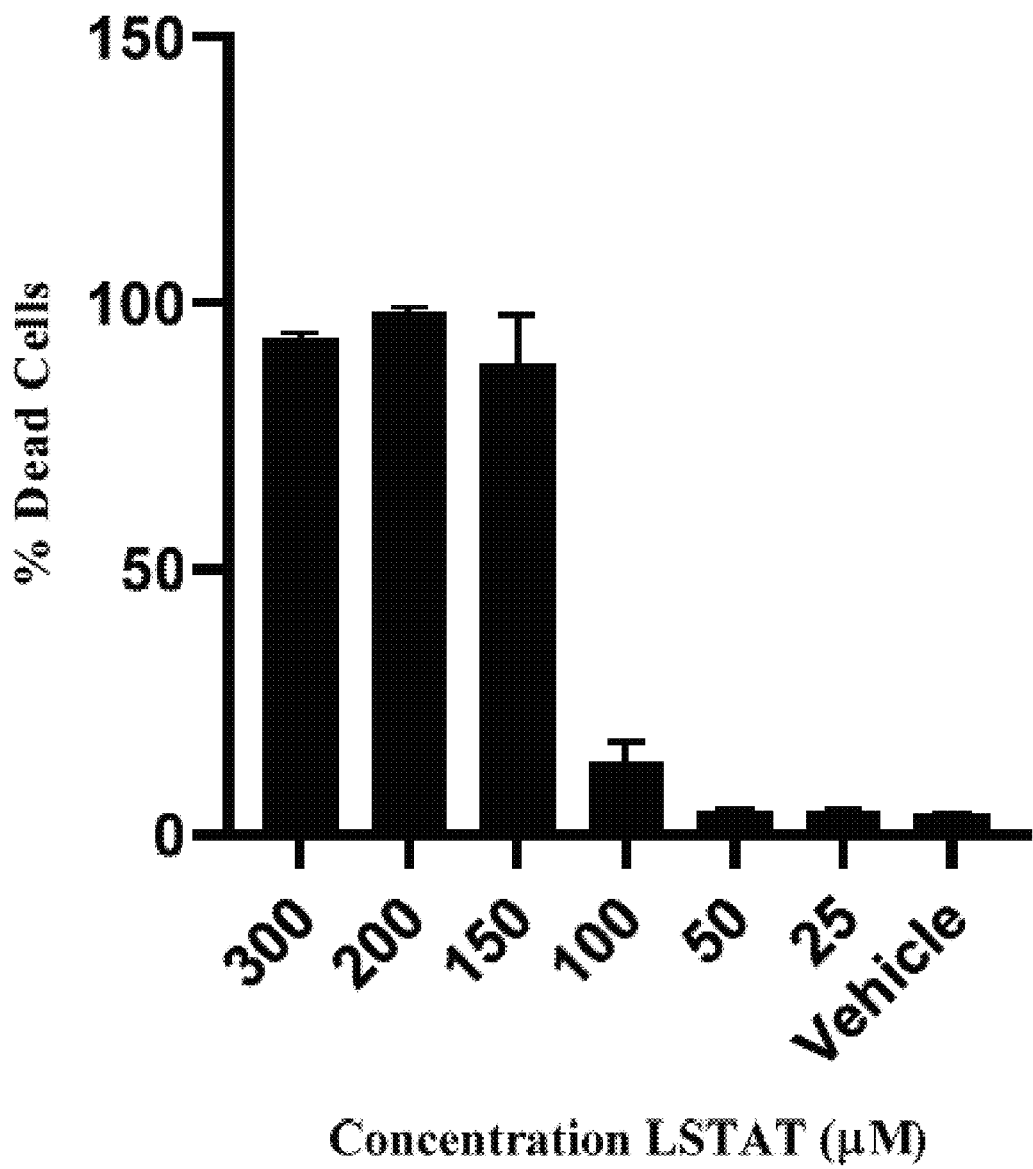
FIG. 13C is a graphical depiction of the cell viability of PSN-1 iCTC cells at the 48-hour time point under various concentrations of an exemplary monolaurin, inosine, and beta-glucan composition in accordance with embodiments of the present invention.

PSN-1
PSN-1 human pancreatic adenocarcinoma responded to concentrations of the exemplary composition between 100 and 300 μM in a dose-dependent manner, where the largest differences were seen in the range between 50 and 150 μM composition (FIGS. 13A-13C). At 48 hours, the percentage of dead cells ranged from 4-5% at 0-50 μM composition to 88±9%, 98±1%, and 93±1% in groups treated with 150, 200 and 300 μM, respectively (FIGS. 13B and 13C). Similar to the other BxPC-3 pancreatic cancer cell line, the pattern of PSN-1 proliferation varied among the study groups receiving the higher concentrations (≥150 μM) of the composition; as with BxPC-3 cells, PSN-1 cell numbers remained at or below initial values up to 48 hours (FIG. 13A).

Summary of Effects of Novel Combination Monolaurin, Inosine, and β-Glucan on Proliferation and Viability of iCTCs Obtained from Human Cancer Cell Lines HCT-116, A549, HL-60, RS4;11, U-251, BxPC-3, and PSN-1:

Cell lines varied in their response to the composition. Without being bound by theory, it is suspected that certain cell lines may be more responsive to treatment with the composition because they are characterized as comprising solid tumors (as opposed to hematological cancers). The cell lines generally showed dose-dependent sensitivity to the composition, with the more responsive cell lines displaying sensitivity starting at composition concentrations between 50 μM (U-251, BxPC-3 and PSN-1) and 100 μM (HCT-116). PSN-1 cells were the most sensitive to the composition, where 150 μM composition was sufficient to kill 88±9% of the cells by 48 hours (as compared with a maximum 98±1% dead PSN-1 cells when treated with 200 μM composition). BxPC-3 cells displayed the widest cell death response range, with dose-dependent increases in cell death and decreases in cell proliferation from 50 to 300 μM composition.

Table 9 summarizes the effects the exemplary composition has on cell viability at 48 hours and compare the effects the composition has on the proliferation and viability of the cancer cell lines tested in this study.

Monolaurin, a component of the exemplary composition, enhances the expression of miR-378 (reviewed in 10), a regulatory microRNA which has been found at low levels in colorectal cancer (10,13) but high levels in lung cancer (14) and myeloid leukemia (15). Consistent with this, treatment with the composition had a relatively mild impact on RS4;11 B cell acute lymphoblastic leukemia (which displayed the lowest proliferation rate, a 0.53-fold increase in cell number) and A549 lung adenocarcinoma and HL-60 acute myeloid leukemia (which were relatively resistant to composition-induced cell killing at 64% and 26%, respectively). Further, A549 cells possess a phenotype characteristic of type II alveolar epithelia, including constitutive secretion of surfactant (16), a lipoprotein complex that possesses both innate immune and physical qualities that may interfere with a lipid-based agent such as the exemplary composition.

When formulated in 95% ethanol and administered at 10-20 μg/mL (equivalent to 36-73 μM) monolaurin interfered with in vitro activated T cell adhesion (as measured by surface expression of CD3) and actin organization (17). Similarly, cultured MCF7 breast cancer cells treated with lauric acid-coated nanoparticles showed tumoricidal biological activity (reduced viability, increased generation of reactive oxygen species (ROS), increased apoptosis, and disruption of actin networks) when the lauric acid content corresponded to 1-4 μg/mL (equivalent to 5-20 μM lauric acid) (18). By comparison, the lowest effective concentration of the composition to achieve ~90% tumor cell killing in this study was 150 μM monolaurin (which killed 88% of cultured PSN-1 cells), a value that is two- to ten-fold higher than the amounts needed for biological activity in these published studies. Future studies may allow us to test the in vitro efficacy of the composition formulated in other vehicles and tested against additional cell lines, including hepatocellular carcinomas such as HepG2, which routinely metabolize monolaurin (19), and non-transformed cell lines as controls. In vivo studies would allow us to test the effects of the composition, formulated for oral administration or incorporated into mouse chow (7), for efficacy in tumor-bearing animals.

With reference to Table 9, the second column depicts the minimum proliferation of the viable cells (minimum fold-increase standard deviation) upon dose with the exemplary composition. The third column references the maximum percentage of dead cells achieved from the viable tumor cells treated with the composition (percentage error). The fourth column depicts the μM doses of the composition that were used to achieve the a) minimum fold-increase and the b) maximum percentage of dead cells.

TABLE 9

Proliferation and Viability of Tumor Cells Treated with the Exemplary Composition of Monolaurin, Inosine, and Beta-Glucan

| cell line | minimum fold-increase | maximum % dead cells | dose[1] (μM) |
| --- | --- | --- | --- |
| HCT-116 | 1.11 ± 0.08 | 88 ± 6 | a, b) 300 |
| A549 | 2.01 ± 0.39 | 64 ± 15 | a, b) 300 |
| HL-60 | 0.82 ± 0.16 | 26 ± 2 | a) 200, b) 300 |
| RS4; 11 | 0.53 ± 0.08 | 98 ± 2 | a) 200, b) 300 |
| U-251 | 1.23 ± 0.13 | 98 ± 1 | a, b) 300 |
| BxPC-3 | ~1.67 ± 0.19 | 88 ± 2 | a, b) 300 |
| PSN-1 | 0.72 ± 0.07 | 98 ± 1 | a) 300, b) 200 |

[1] a) Dose used obtain the minimum fold-increase to cell number, and b) Dose used to obtain maximum % dead cells.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A composition for treating, inhibiting proliferation of, and/or killing cells associated with metastatic cancer progression in a cancer patient in need thereof, the composition comprising monolaurin, inosine, and β-glucan, wherein the composition comprises monolaurin, inosine and β-glucan in a ratio of 1000:15:340 (w/w/w).

2. The composition of claim 1, wherein the composition further comprises one or more cancer metabolism disruptors, chemotherapeutics, and modulators of immune response at a concentration from about 1 μM to about 200 μM.

3. The composition of claim 1, wherein the composition comprises the monolaurin in a concentration between 25 μM and 300 μM.

4. The composition of claim 1, wherein the composition further comprises one or more cancer metabolism disruptors, chemotherapeutics, and modulators of immune response comprise one or more naturally occurring or modified carbohydrates, amino acids, peptides, and lipopolysaccharides.

5. The composition of claim 1, wherein the monolaurin is present in an amount or concentration capable of killing cells associated with progression of metastatic cancer by at least 20% within the cancer patient.

6. The composition of claim 5, wherein the concentration of monolaurin is submicromolar to about 300 μM.

* * * * *